United States Patent
Kowol et al.

(10) Patent No.: US 11,572,379 B2
(45) Date of Patent: Feb. 7, 2023

(54) MONOMALEIMIDE-FUNCTIONALIZED PLATINUM COMPOUNDS FOR CANCER THERAPY

(71) Applicants: Medizinische Universität Wien, Vienna (AT); Universität Wien, Vienna (AT)

(72) Inventors: Christian Kowol, Vienna (AT); Petra Heffeter, Vienna (AT); Walter Berger, Vienna (AT); Bernhard K. Keppler, Gaweinstal (AT); Josef Mayr, Vienna (AT); Verena Pichler, Vienna (AT)

(73) Assignees: MEDIZINISCHE UNIVERSITÄT WIEN, Vienna (AT); UNIVERSITÄT WIEN, Vienna (AT)

(*) Notice: Subject to any disclaimer, the term of this patent is extended or adjusted under 35 U.S.C. 154(b) by 15 days.

(21) Appl. No.: 16/904,528

(22) Filed: Jun. 17, 2020

(65) Prior Publication Data

US 2021/0002313 A1 Jan. 7, 2021

Related U.S. Application Data

(62) Division of application No. 16/060,559, filed as application No. PCT/EP2016/080453 on Dec. 9, 2016, now Pat. No. 10,723,748.

(30) Foreign Application Priority Data

Dec. 9, 2015 (EP) .................................... 15198739

(51) Int. Cl.
*A61K 31/555* (2006.01)
*C07F 15/00* (2006.01)
(Continued)

(52) U.S. Cl.
CPC ........ *C07F 15/0093* (2013.01); *A61K 31/555* (2013.01); *A61P 35/00* (2018.01); *A61P 35/02* (2018.01)

(58) Field of Classification Search
CPC ...... C07F 15/0093; A61P 35/00; A61P 35/02; A61K 31/555
(Continued)

(56) References Cited

U.S. PATENT DOCUMENTS

| 4,140,707 A | 2/1979 | Cleare |
| 9,403,858 B2 | 8/2016 | Bilodeau et al. |

(Continued)

FOREIGN PATENT DOCUMENTS

| CN | 108164512 | 6/2018 |
| CN | 108187063 | 6/2018 |

(Continued)

OTHER PUBLICATIONS

Amable, "Cisplatin resistance and opportunities for precision medicine," *Pharmacological Research*, 106:27-36, 2016.
(Continued)

*Primary Examiner* — Taylor V Oh
(74) *Attorney, Agent, or Firm* — Parker Highlander PLLC

(57) ABSTRACT

The present invention relates to novel monomaleimide-functionalized platinum compounds of formula (I), including in particular novel monomaleimide-functionalized oxaliplatin and carboplatin derivatives, as well as their use as medicaments, particularly for the treatment or prevention of cancer.

(Continued)

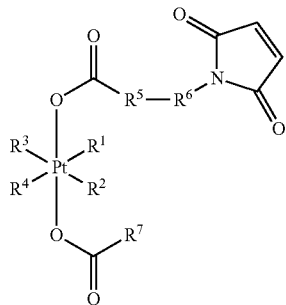

27 Claims, 9 Drawing Sheets

Figure 1G:
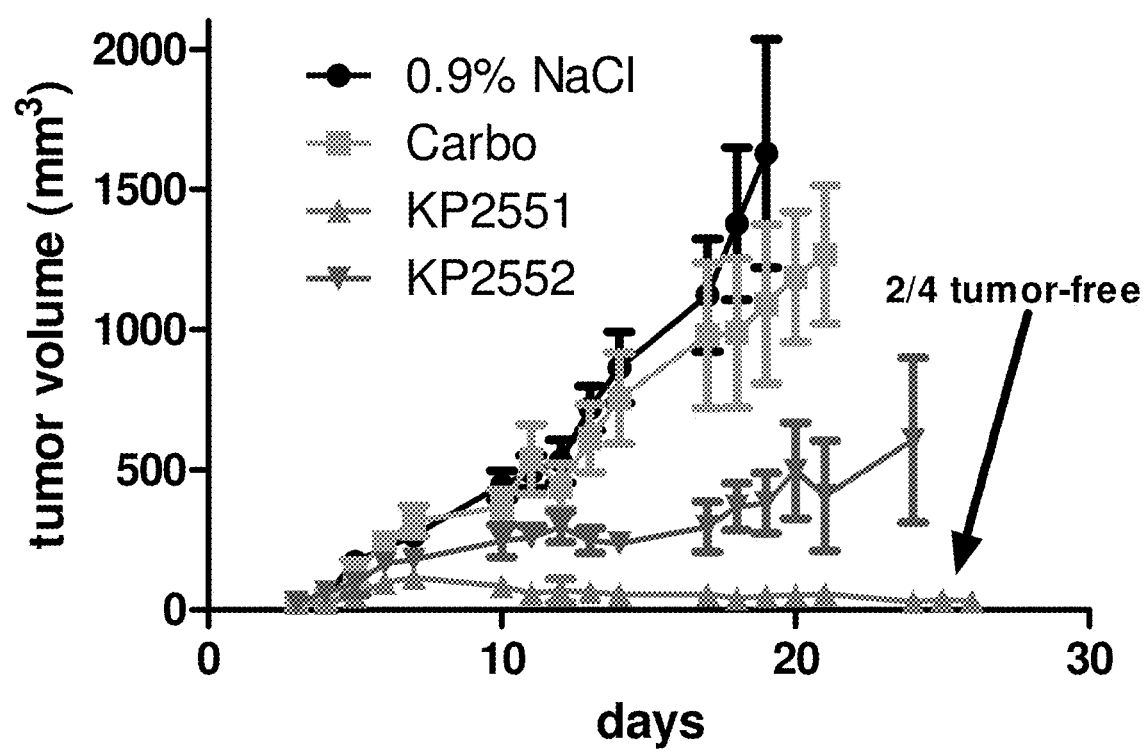

(51) Int. Cl.
    *A61P 35/02*     (2006.01)
    *A61P 35/00*     (2006.01)

(58) Field of Classification Search
    USPC .......................................................... 514/184
    See application file for complete search history.

(56) References Cited

U.S. PATENT DOCUMENTS

| | | |
|---|---|---|
| 2003/0103896 A1 | 6/2003 | Smith |
| 2006/0063832 A1 | 3/2006 | Franc et al. |
| 2006/0089341 A1 | 4/2006 | Kratz et al. |
| 2006/0205810 A1 | 9/2006 | Zong et al. |
| 2007/0232819 A1 | 10/2007 | Franc et al. |
| 2008/0008740 A1 | 1/2008 | Franc et al. |
| 2009/0175947 A1 | 7/2009 | Franc et al. |
| 2009/0209641 A1 | 8/2009 | Franc et al. |
| 2010/0010083 A1 | 1/2010 | Franc et al. |
| 2013/0224228 A1 | 8/2013 | Jackson et al. |
| 2016/0068557 A1 | 3/2016 | Bilodeau et al. |
| 2016/0326201 A1 | 11/2016 | Bilodeau et al. |
| 2017/0348422 A1 | 12/2017 | Pillow et al. |
| 2018/0055944 A1 | 3/2018 | Lu et al. |
| 2018/0186823 A1 | 7/2018 | Kadiyala et al. |
| 2018/0243318 A1 | 8/2018 | Alargova et al. |
| 2019/0015525 A1 | 1/2019 | Steinmetz et al. |

FOREIGN PATENT DOCUMENTS

| | | |
|---|---|---|
| EP | 0275559 | 7/1988 |
| WO | WO 1998/010794 | 3/1998 |
| WO | WO 2000/076551 | 12/2000 |
| WO | WO 2015/102922 | 7/2015 |
| WO | WO 2015/151081 | 10/2015 |
| WO | WO 2015/200250 | 12/2015 |
| WO | WO 2018/009811 | 1/2018 |

OTHER PUBLICATIONS

Beck et al., "Direct observation of covalent adducts with Cys34 of human serum albumin using mass spectrometry," *Analytical Biochemistry*, 325:326-336, 2004.
European Extended Search Report on European Application No. 15198739.3-1451, dated May 17, 2016.
Garmann et al., "Cellular accumulation and cytotoxicity of macromolecular platinum complexes in cisplatin-resistant tumor cells," *Journal of Controlled Release*, 131:100-106, 2008.
Gibson, "Platinum(IV) anticancer prodrugs—hypotheses and facts," *Dalton Trans.*, 45:12983-12991, 2016.
Hall et al., "Basis for design and development of platinum(IV) anticancer complexes," *J Med Chem*, 50(15):3403-3411, 2007.
International Search Report and Written Opinion of International Application No. PCT/EP2016/080453, dated Apr. 4, 2017.
International Preliminary Report on Patentability of International Application No. PCT/EP2016/080453, dated Jun. 21, 2018.
Johnstone et al., "The Next Generation of Platinum Drugs: Targeted Pt(II) Agents, Nanoparticle Delivery, andPt(IV) Prodrugs," *Chem Rev.*, 116(5):3436-3486, 2016.
Jungwirth et al., "Anticancer activity of metal complexes: involvement of redox processes," *Antioxid Redox Signal*, 15(4):1085-1127, 2011.
Korst et al., "Influence of single and multiple doses of amifostine on the efficacy and the pharmacokinetics of carboplatin in mice," *British Journal of Cancer*, 75(10), 1439-1446, 1997.
Kratz, "Albumin as a drug carrier: design of prodrugs, drug conjugates and nanoparticles," *J Control Release*, 132:171-183, 2008.
Kratz, "A clinical update of using albumin as a drug vehicle—A commentary," *Journal of Controlled Release*, 190:331-336, 2014.
Kratz "DOXO EMCH INN0206: the first Alb binding prodrug of doxorubicin to enter clinical trials," *Expert Opin. Investig. Drugs*, 16(6):855-866, 2007.
Kratz and Beyer, "Semm Proteins as Drug Carriers of Anticancer Agents: A Review," *Drug Delivery*, 5:281-299, 1998.
Kratz et al., "A Novel Macromolecular Prodrug Concept Exploiting Endogenous Serum Albumin as a Drug Carrier for Cancer Chemotherapy," *J. Med. Chem.*, 43:1253-1256+Supplementary materials, 2000.
Kratz et al., "Acute and repeat-dose toxicity studies of the (6-maleimidocaproyl)hydrazone derivative of doxombicin (DOXO-EMCH), an albuminbinding prodrug of the anticancer agent doxombicin," *Human & Experimental Toxicology*, 26:19-35, 2007.
Kratz et al., "Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound," *J. Med. Chem.*, 45:5523-5533, 2002.
Larsen et al., "Albumin-based drug delivery: harnessing nature to cure disease," *Molecular and Cellular Therapies*, 4:3, 2016.
Neumann et al., "Native albumin for targeted drug delivery," *Expert Opin Drug Deliv*, 7(8):915-925, 2010.
Pichler et al., "Maleimide-fimctionalised platinum(IV) complexes as a synthetic platform for targeted drug delivery," *Chemical Communications* (Cambridge, United Kingdom), 49(22):2249-2251, 2013.
Schütte et al., "Development of Acid-Sensitive Platinum(II) Complexes With Protein-Binding Properties," *Metal-Based Drugs*, 7(2):89-100, 2000.
Schütte et al., "Synthesis of two maleimide derivatives of cis-configurated platinum(II) complexes for the preparation of chemoimmunoconjugates," *Inorganica Chimica Acta*, 267:133-136, 1998.
Sleep et al., "Albumin as a versatile platform for drug half-life extension," *Biochimica et Biophysica Acta*, 1830:5526-5534, 2013.
Trevaskis et al., "From sewer to saviour—targeting the lymphatic system to promote drug exposure and activity," *Nature Reviews Drug Discovery*, 14:781-803, 2015.
Wang et al., "Pretreatment with Dexamethasone Increases Antitumor Activity of Carboplatin and Gemcitabine in Mice Bearing Human Cancer Xenografts: In Vivo Activity, Pharmacokinetics, and Clinical Implications for Cancer Chemotherapy," *Clinical Cancer Research*, 10:1633-1644, 2004.
Warnecke et al., "Synthesis and Biological Activity of Water-Soluble Maleimide Derivatives of the Anticancer Drug Carboplatin Designed as Albumin-Binding Prodrugs," *Bioconjugate Chem.*, 15:1349-1359, 2004.
Zheng et al., "Pt(IV) Prodrugs Designed to Bind Non-Covalently to Human Serum Albumin for Drug Delivery," *J. Am. Chem. Soc.*, 136:8790-8798, 2014.
"Cervical cancer treatment regimens," Cancer Therapy Advisor, pp. 1-4, 2019.
"FDA-approved ovarian cancer treatments," located at www.empr.com/charts/fda-approved-ovarian-cancer-treatments/, 2022.

(56) References Cited

OTHER PUBLICATIONS

Caparica et al., "How I treat metastatic triple-negative breast cancer," *ESMO Open*, 4:e000504, 2019.

Chávarri-Guerra et al., "Systemic therapy for non-serous ovarian carcinoma," *Chin Clin Oncol.*, 9(4):52, 2020.

Devaraja, "Current prospects of molecular therapeutics in head and neck squamous cell carcinoma," *Pharmaceutical Medicine*, 33:269-289, 2019.

Farid et al., "Chemo-immunotherapy as first-line treatment for small-cell lung cancer," *Ther Adv Med Oncol*, 12:1-10, 2020.

Hanna et al., "Therapy for stage IV non-small-cell lung cancer without driver alterations: ASCO and OH (CCO) joint guideline update," *J Clin Oncol.*, 38(14):1608-1632, 2020.

Kitamura et al., "Current trends and future prospects of molecular targeted therapy in head and neck squamous cell carcinoma," *Int. J. Mol. Sci.*, 22:240, 2021.

Wang et al., "New insights into small-cell lung cancer development and therapy," *Cell Biol Int.*, 44:1564-1576, 2020.

FIGS. 1A-B
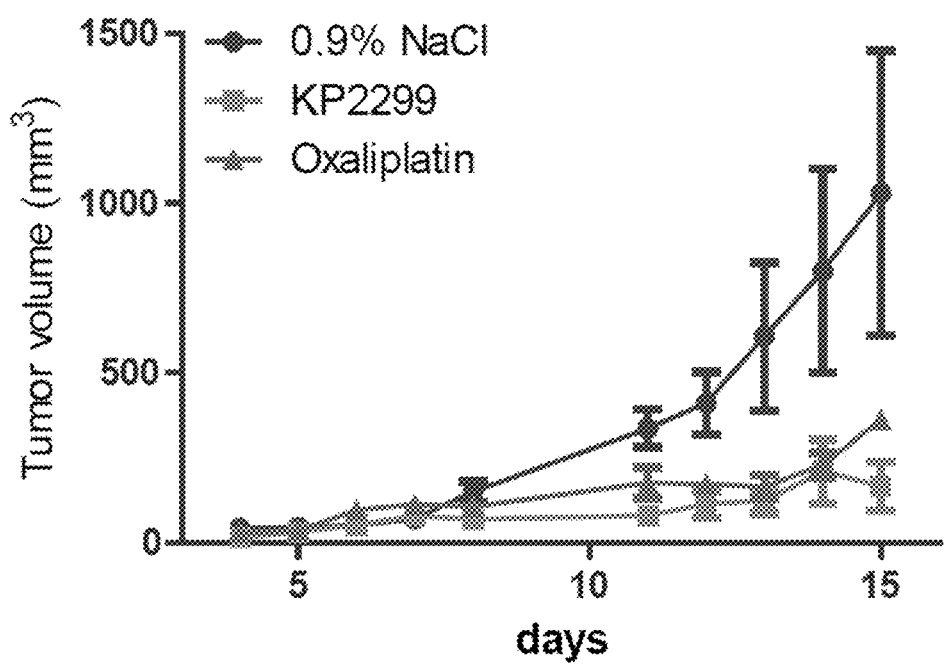
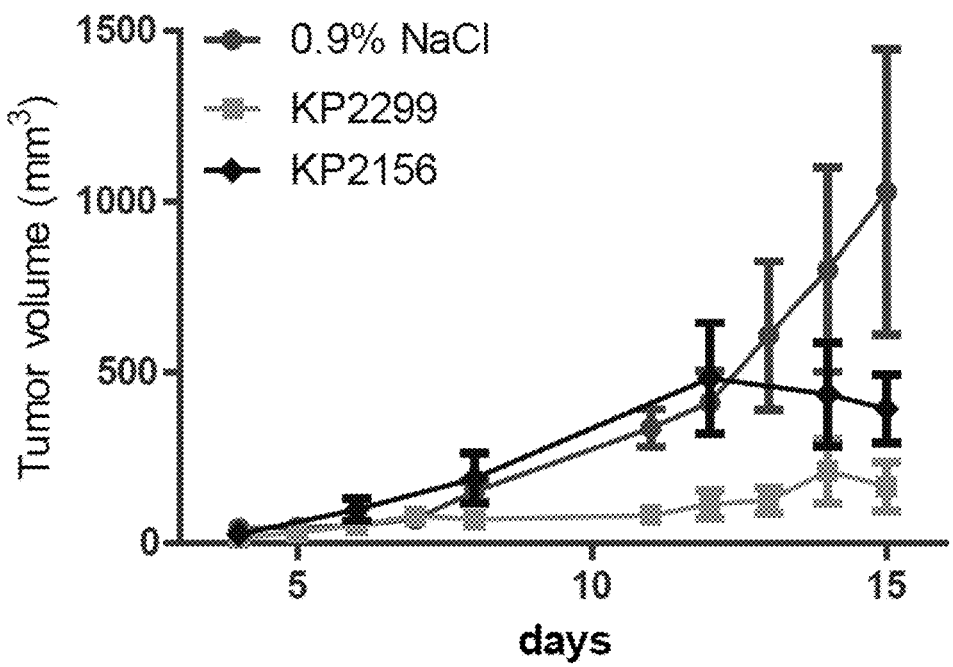

FIGS. 1C-D
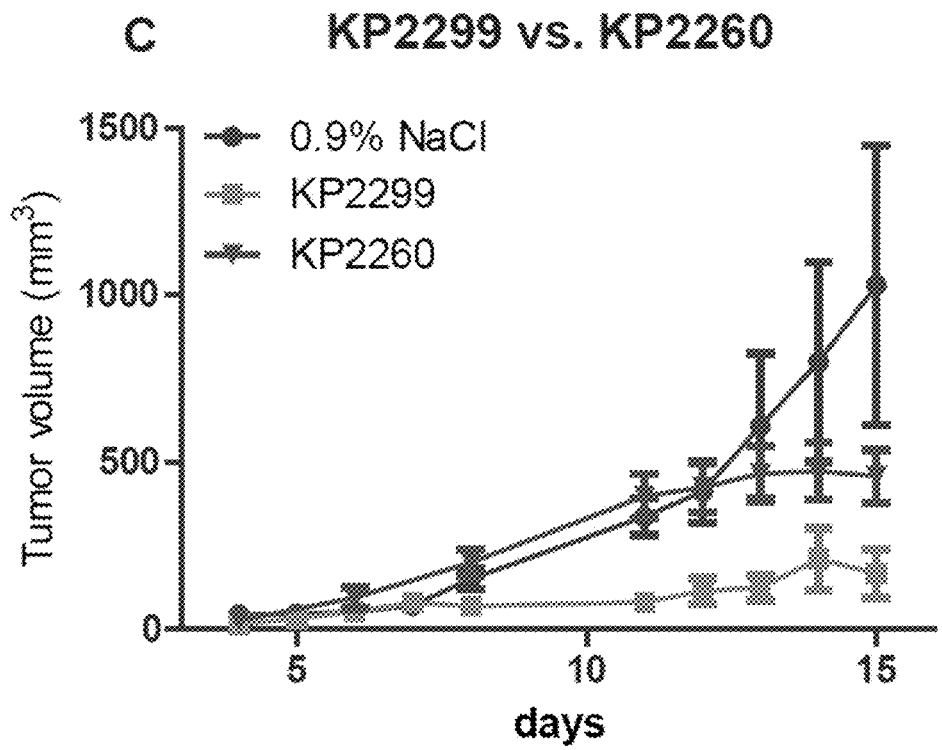
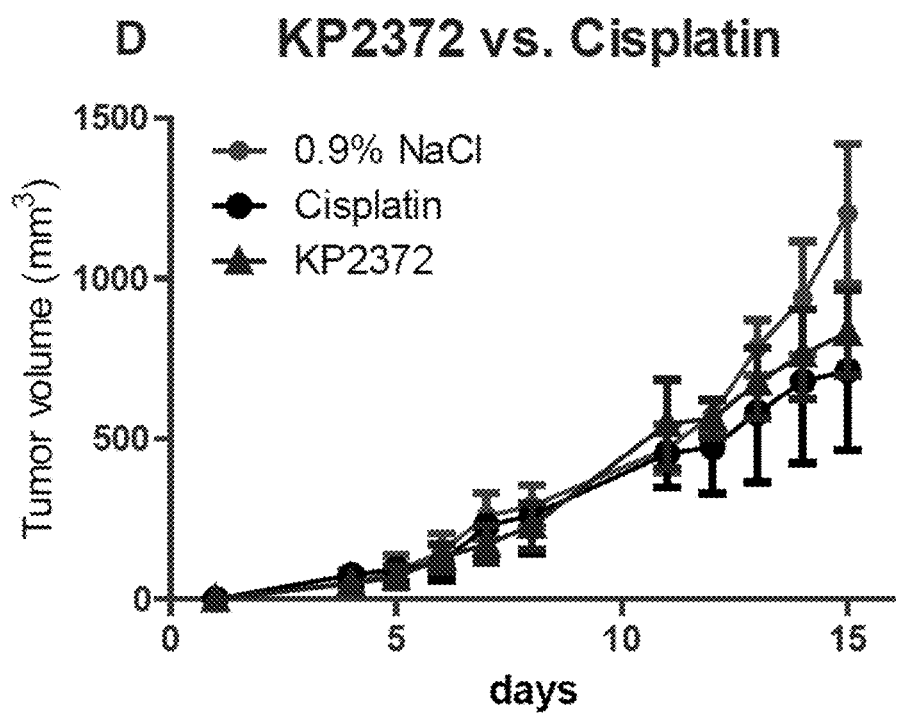

FIGS. 1E-F
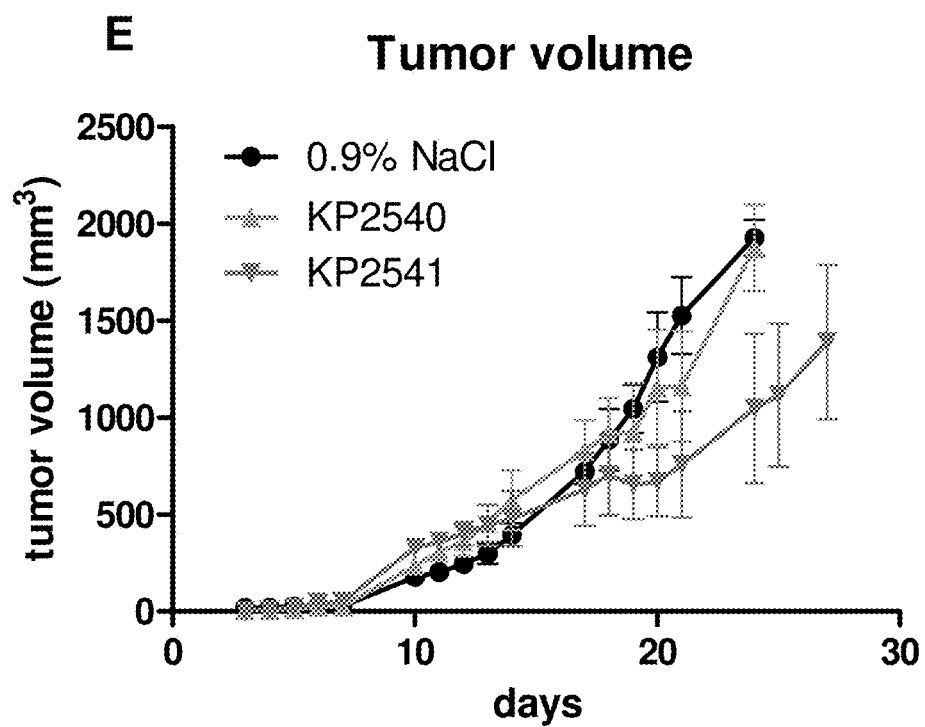
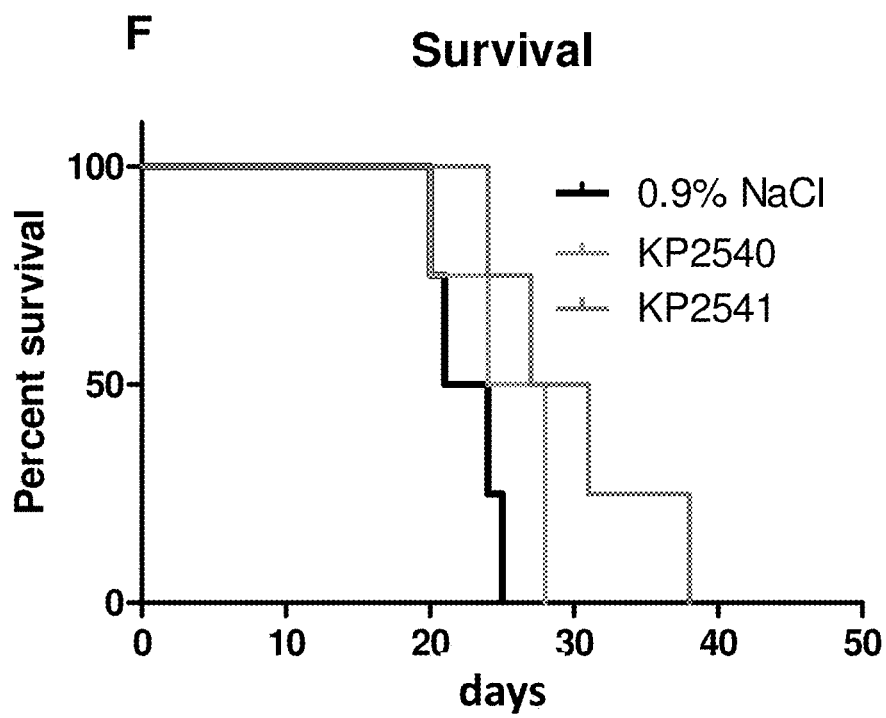

FIGS. 2A-B
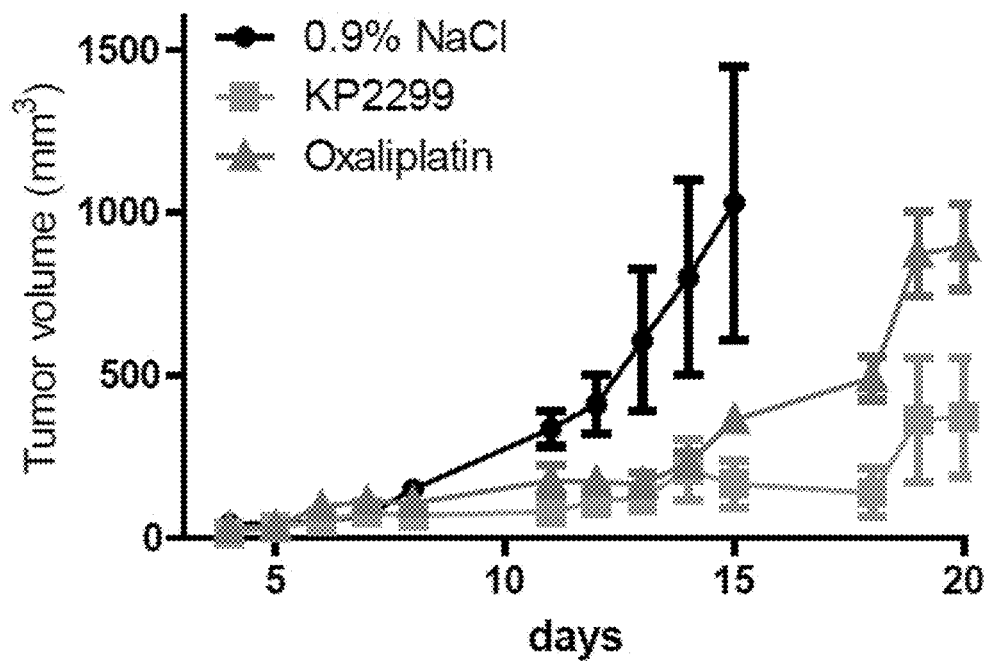
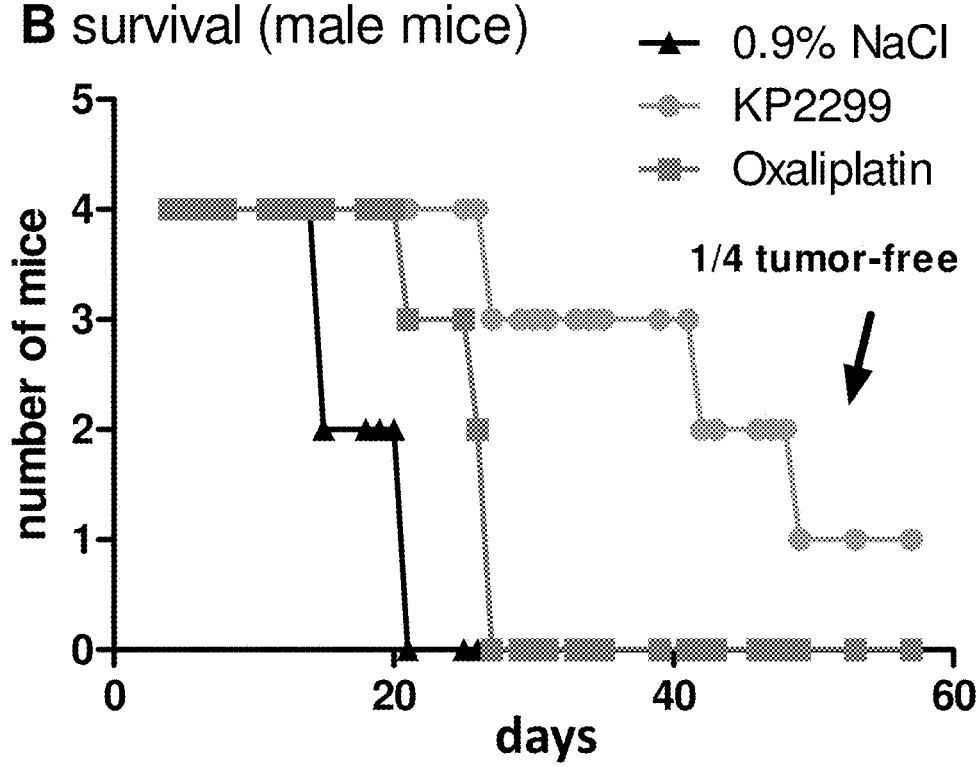

FIGS. 2C-D
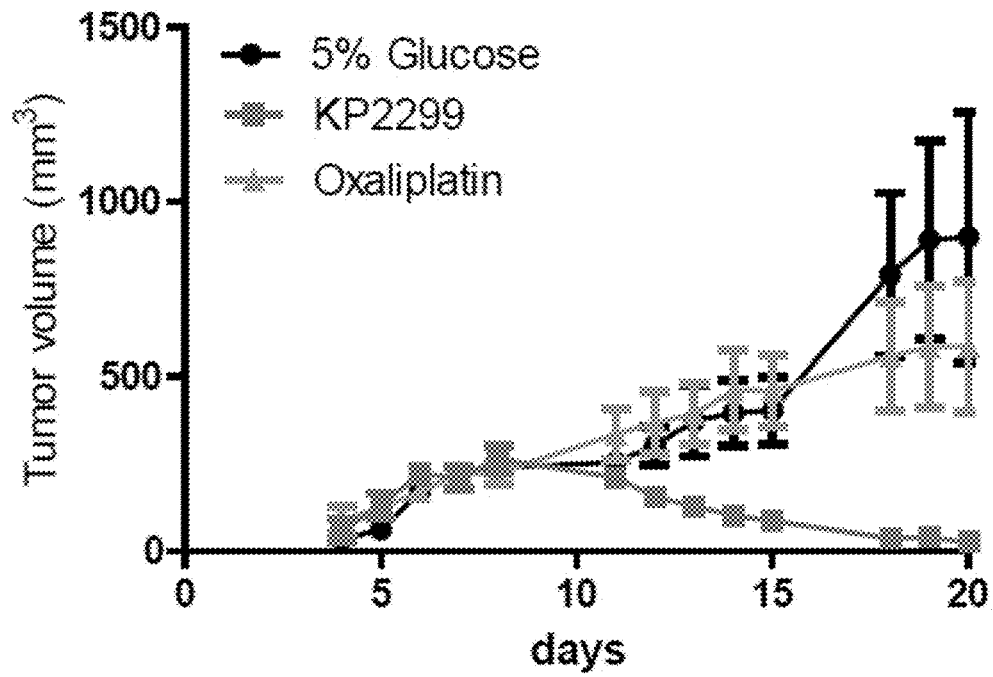
C female mice
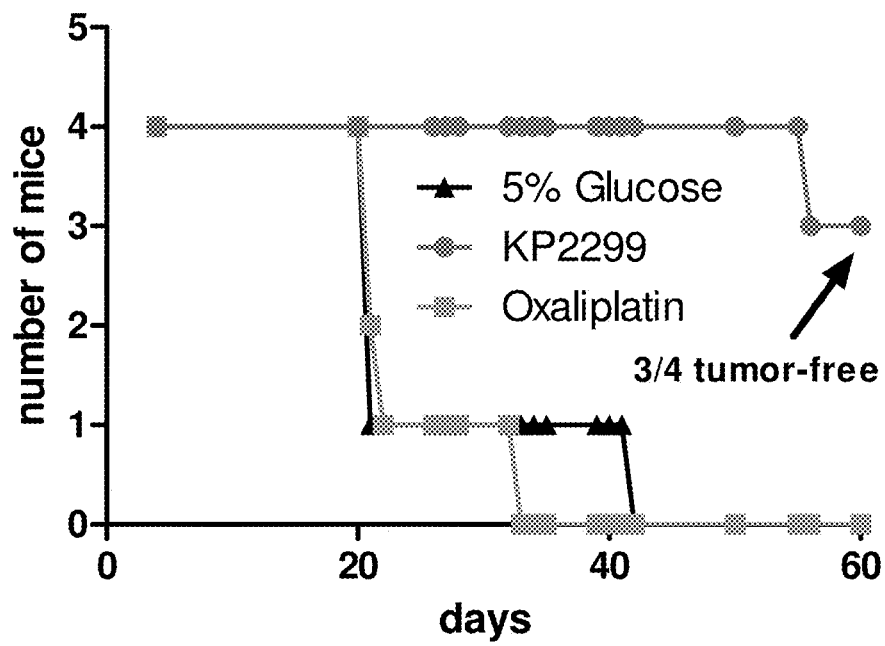
D survival (female mice)

FIG. 3
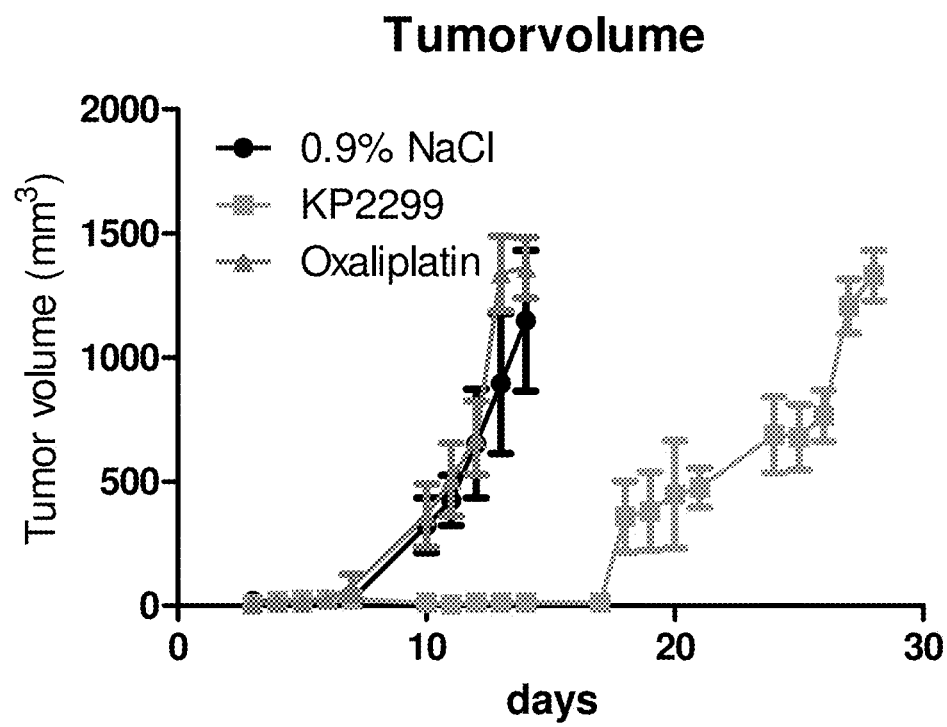
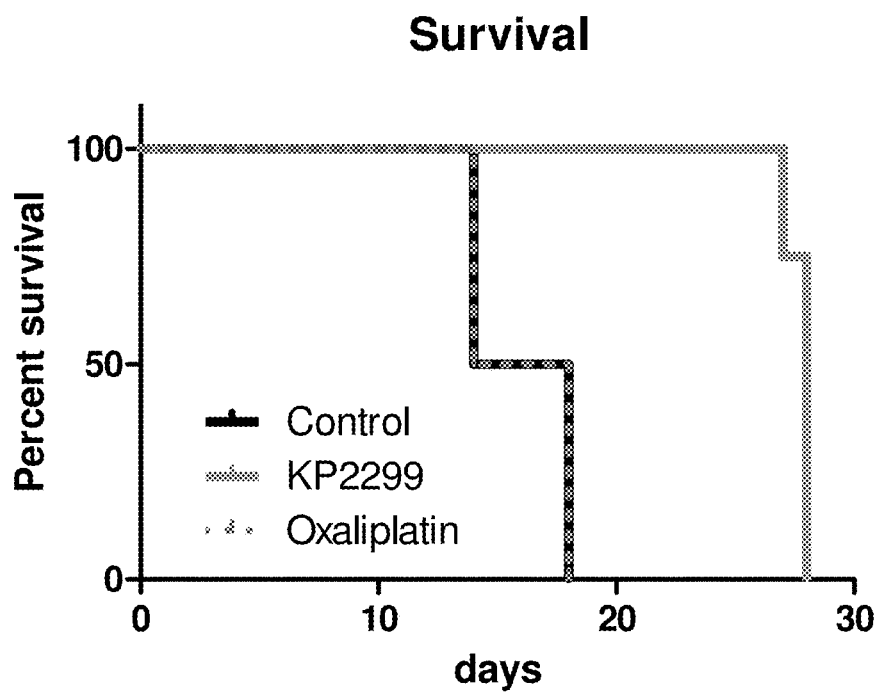

FIG. 4
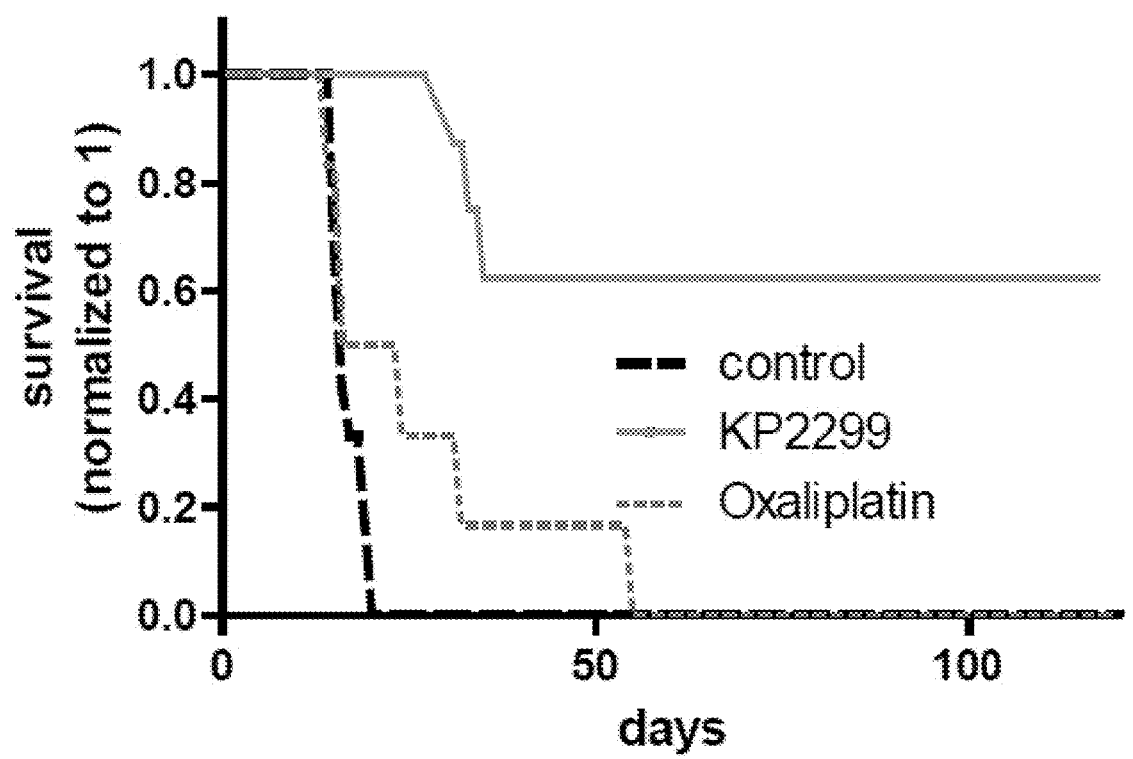
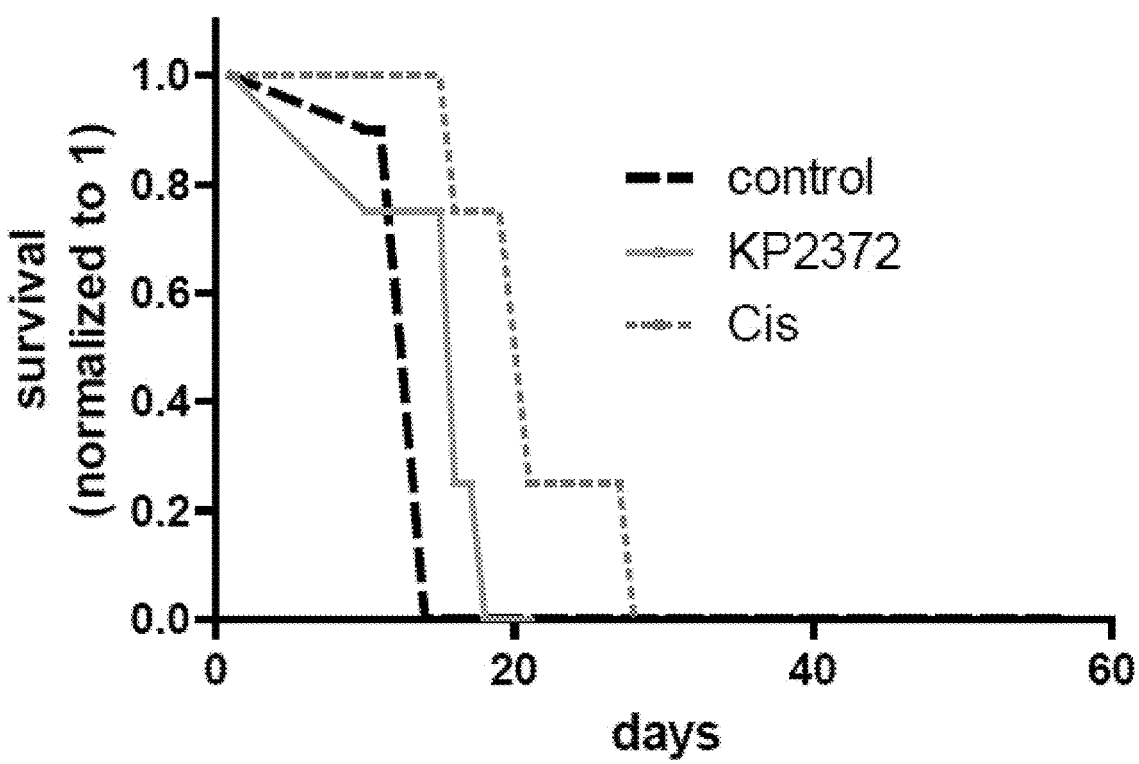

MONOMALEIMIDE-FUNCTIONALIZED PLATINUM COMPOUNDS FOR CANCER THERAPY

This application is a divisional of U.S. application Ser. No. 16/060,559, filed Jun. 8, 2018, which is a national phase application under 35 U.S.C. § 371 of International Application No. PCT/EP2016/080453, filed Dec. 9, 2016, which claims benefit of European Application No. 15198739.3, filed Dec. 9, 2015, the entire contents of each of which are hereby incorporated by reference.

The present invention relates to novel monomaleimide-functionalized platinum compounds of formula (I), as described and defined herein below, including in particular novel monomaleimide-functionalized oxaliplatin and carboplatin derivatives, as well as their use as medicaments, particularly for the treatment or prevention of cancer.

The application of platinum drugs in clinical cancer therapy roots in 1969, when Rosenberg et al. discovered the promising anticancer activity of the platinum(II) complex cisplatin. The anticancer activity of cisplatin is mainly based on the formation of platinum-DNA adducts, which leads to distortion of the helical DNA structure. This results in DNA strand breaks, inhibition of DNA replication and transcription, and as a final consequence cell cycle arrest and apoptosis. Based on its very strong anticancer activity, cisplatin or its successors carboplatin and oxaliplatin are nowadays an inherent part in nearly every chemotherapeutic scheme. Certain derivatives of such platinum drugs have also been proposed, e.g., in: Abramkin, S. A. et al. *J Med Chem.* 2010; 53(20):7356-64; Abramkin, S. et al. *Dalton Trans.* 2012; 41(10):3001-5; Abramkin, S., Dissertation 2012; and WO 2015/102922. However, treatment with platinum drugs is always accompanied (besides occurrence of intrinsic or acquired resistance) by (severe) side effects, which include besides nausea and vomiting, also nephrotoxicity or neurotoxicity. Consequently, there is significant interest in the development of new strategies to enhance tumor targeting (and consequently to reduce side effects) of platinum drugs.

The anticancer activity of platinum(IV) complexes was discovered together with cisplatin in the 1960s. So far, three platinum(IV) drugs have been tested in clinical trials: JM9 (iproplatin), tetraplatin (ormaplatin), and JM-216 (satraplatin). In general, platinum(IV) complexes are kinetically more inert than their platinum(II) counterparts and have consequently a lower reactivity with biomolecules. Probably due to their reduced cytotoxicity, platinum(IV) drugs have been less extensively studied and developed than platinum(II) compounds. Nowadays, platinum(IV) complexes are considered as prodrugs, which undergo reduction in the tumor tissue. During this process preferably the axial ligands are released and the corresponding more active square-planar platinum(II) analogues are formed. Especially these axial ligands are of paramount interest as they can be used for modulating a range of physicochemical and pharmacological properties such as lipophilicity, stability and reduction potential. Furthermore, the ligands can be designed to target specific tumor sites or to attach additional bioactive components.

Albumin is the most abundant plasma protein (35-50 g/L in human plasma) with a molecular weight of 66.5 kDa. Albumin has an average half-life of 19 days and is, like most plasma proteins, synthesized in the liver. The physiological functions of albumin are multiple and diverse. For example, it is the major protein responsible for the colloid osmotic pressure of the blood. Most importantly with respect to drug delivery, albumin, a physiological carrier for several molecules such as bilirubin or metal ions, has very potent binding properties and is known to bind several therapeutic drugs (e.g. penicillins). Moreover, it is known that, due to the combination of leaky blood capillary with the absence/defect of lymphatic drainage, albumin accumulates in malignant tissue (also called enhanced permeability and retention (EPR) effect). Consequently, strategies to enhance binding of drugs to serum albumin are an attractive and effective approach for targeted drug delivery into the tumor tissue. Currently, there are several attempts to use the specific tumor accumulation of albumin also for cytotoxic drugs especially paclitaxel and doxorubicin. Thus, Abraxane®, an albumin paclitaxel-containing nanoparticle, has been recently approved for non-small cell lung cancer (NSCLC) as well as non-responding or relapsed breast cancer and the maleimide-containing doxorubicin derivative (INNO-206, aldoxorubicin) is currently in phase III clinical trials. Consequently, the effectiveness and advantages of albumin as a tumor-targeting strategy has already been proven in the clinical situation.

In a recent study (Pichler V et al. *Chem Commun (Camb).* 2013; 49(22):2249-51), the first bismaleimide-containing, albumin-binding platinum(IV) drug KP2156 was synthesized together with the respective succinimide derivative KP2157, which was found to possess no reactivity towards albumin.

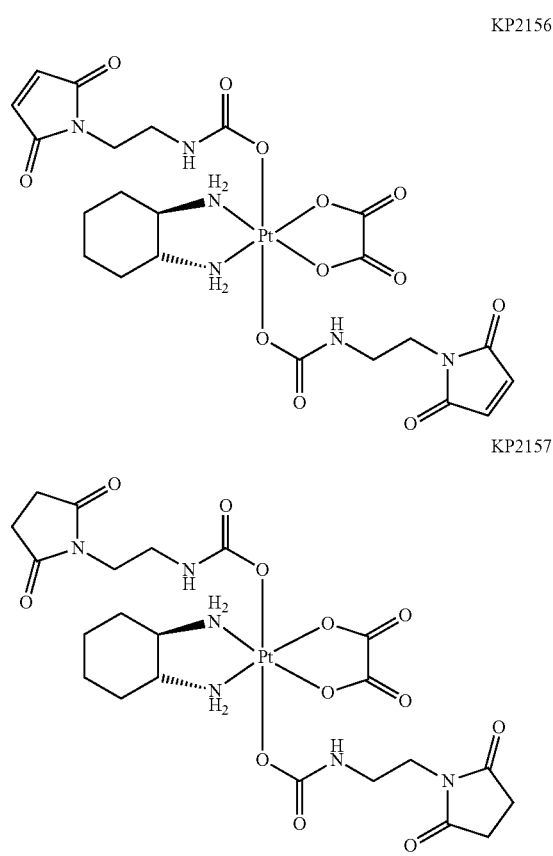

In particular, SEC-ICP-MS measurements using bovine blood serum proved specific binding of KP2156 to the albumin-containing protein fraction, while KP2157 was exclusively detected in the low molecular weight fraction.

To test the impact of albumin binding on the anticancer activity of the new compounds in vivo the murine CT-26 colon cancer model was used (the use of this syngeneic murine tumor model was necessary due to recently reported importance of the immune system for the anticancer activity of oxaliplatin; Kroemer G et. al. *Oncogene,* 2010, 29, 482-491; Jungwirth U et al. *Mol Pharmacol.* 2012; 81(5): 719-28). Both platinum complexes were well tolerated with no significant loss of body weight. However, in comparison to KP2157, the bismaleimide-functionalized derivative KP2156 displayed a significantly higher anticancer activity, resulting in a distinctly reduced mean tumor burden.

Interaction studies with albumin furthermore revealed that despite the presence of two maleimide moieties, KP2156 is able to bind only to one albumin molecule. The present inventors contemplated that the free second maleimide will result in unspecific reactions with other proteins or thiol-containing molecules, and that this could lead to an uncontrolled behavior due to the occurrence of multiple metabolites in vivo.

To address this issue, in the context of the present invention, the first mono-maleimide-functionalized oxaliplatin, cisplatin and carboplatin derivatives were developed and tested for their anticancer activity in vivo. This resulted in several completely unexpected discoveries:

1) Although the albumin binding kinetic for the bismaleimide derivatives is in all cases 2-fold faster than for the monomaleimides, one of the new oxaliplatin monomaleimide complexes as well as a carboplatin analogue provided herein, i.e. KP2299 and KP2551, were found to be distinctly more active than all other tested compounds (including oxaliplatin, cisplatin and carboplatin), as also shown in FIGS. 1 and 2.

2) The monomaleimide compound KP2299 showed distinctly higher anticancer activity than the structurally very similar monomaleimide compound KP2260 (which has a methoxido group instead of the acetato group of KP2299 at one axial position, as depicted below) and than KP2541 which lacks the NH group in its linker, as also shown in FIGS. 1C and 1E. In addition, KP2299 exhibited highly increased aqueous solubility compared to KP2260.

3) The cisplatin analogues of KP2299, namely KP2372 and KP2540, were only marginally active (see FIGS. 1D and E). This was highly surprising as cisplatin derivatives usually possess similar or even higher anticancer activity.

4) In contrast to KP2372, KP2299 also exerted distinct anti-leukemic activity (see FIG. 4). This was surprising as no EPR effect can be observed in hematologic diseases (the accumulation of albumin can only be rationally explained for solid tumors).

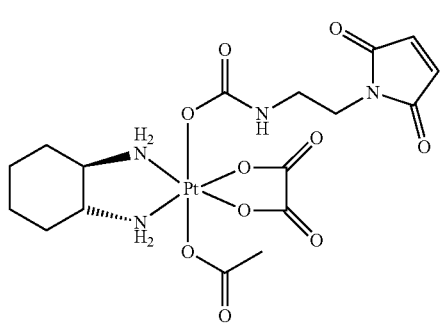

KP2299

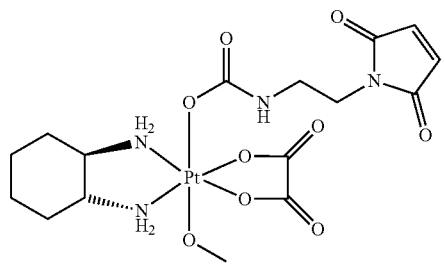

KP2260

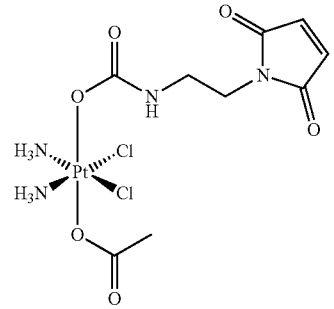

KP2372

The present invention thus solves the problem of providing novel and improved platinum drugs for the therapeutic intervention in cancer, which show a considerably increased therapeutic effectiveness and a favorable side effect profile, particularly due to an advantageously enhanced tumor targeting.

Accordingly, the present invention provides a compound of the following formula (I)

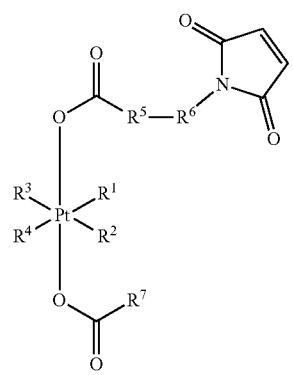

(I)

or a pharmaceutically acceptable salt or solvate thereof.

In formula (I), $R^1$ and $R^2$ are joined together to form a moiety (A1), (A2) or (A3):

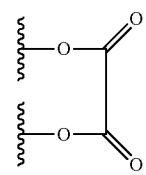

(A1)

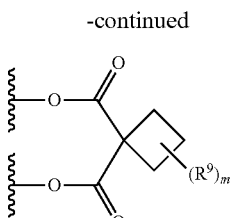
(A2)

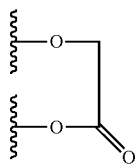
(A3)

$R^3$ and $R^4$ are joined together to form a moiety (1), or $R^3$ is a moiety (B2) and $R^4$ is —NH$_3$, or $R^3$ and $R^4$ are each —NH$_3$:

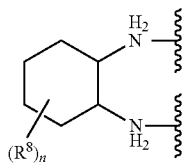
(B1)

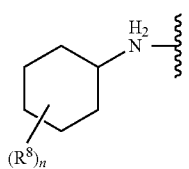
(B2)

$R^5$ is —N(R$^{51}$)— or —CH$_2$—.

$R^{51}$ is hydrogen or C$_{1-8}$ alkyl.

$R^6$ is C$_{1-8}$ alkylene, wherein one or two —CH$_2$— units comprised in said C$_{1-8}$ alkylene are each optionally replaced by a group independently selected from —O—, —CO—, —C(=O)O—, —O—C(=O)—, —N(R$^{61}$)—, —N(R$^{61}$)—CO—, —CO—N(R$^{61}$)—, arylene, and heteroarylene, wherein said arylene and said heteroarylene are each optionally substituted with one or more groups R$^{62}$.

Each R$^{61}$ is independently selected from hydrogen and C$_{1-8}$ alkyl.

Each R$^{62}$ is independently selected from C$_{1-8}$ alkyl, C$_{2-8}$ alkenyl, C$_{2-8}$ alkynyl, —(C$_{0-3}$ alkylene)-OH, —(C$_{0-3}$ alkylene)-O(C$_{1-8}$ alkyl), —(C$_{0-3}$ alkylene)-SH, —(C$_{0-3}$ alkylene)-S(C$_{1-8}$ alkyl), —(C$_{0-3}$ alkylene)-NH$_2$, —(C$_{0-3}$ alkylene)-NH(C$_{1-8}$ alkyl), —(C$_{0-3}$ alkylene)-N(C$_{1-8}$ alkyl)(C$_{1-8}$ alkyl), —(C$_{0-3}$ alkylene)-halogen, —(C$_{0-3}$ alkylene)-(C$_{1-8}$ haloalkyl), —(C$_{0-3}$ alkylene)-CF$_3$, —(C$_{0-3}$ alkylene)-CN, —(C$_{0-3}$ alkylene)-CHO, —(C$_{0-3}$ alkylene)-CO—(C$_{1-8}$ alkyl), —(C$_{0-3}$ alkylene)-COOH, —(C$_{0-3}$ alkylene)-CO—O—(C$_{1-8}$ alkyl), —(C$_{0-3}$ alkylene)-O—CO—(C$_{1-8}$ alkyl), —(C$_{0-3}$ alkylene)-CO—NH$_2$, —(C$_{0-3}$ alkylene)-CO—NH(C$_{1-8}$ alkyl), —(C$_{0-3}$ alkylene)-CO—N(C$_{1-8}$ alkyl)(C$_{1-8}$ alkyl), —(C$_{0-3}$ alkylene)-NH—CO—(C$_{1-8}$ alkyl), —(C$_{0-3}$ alkylene)-N(C$_{1-8}$ alkyl)-CO—(C$_{1-8}$ alkyl), —(C$_{0-3}$ alkylene)-SO$_2$—NH$_2$, —(C$_{0-3}$ alkylene)-SO$_2$—NH(C$_{1-8}$ alkyl), —(C$_{0-3}$ alkylene)-SO$_2$—N(C$_{1-8}$ alkyl)(C$_{1-8}$ alkyl), —(C$_{0-3}$ alkylene)-NH—SO$_2$—(C$_{1-8}$ alkyl), and —(C$_{0-3}$ alkylene)-N(C$_{1-8}$ alkyl)-SO$_2$—(C$_{1-8}$ alkyl).

$R^7$ is selected from hydrogen, C$_{1-8}$ alkyl, C$_{2-8}$ alkenyl, C$_{2-8}$ alkynyl, cycloalkyl, heterocycloalkyl, aryl, heteroaryl, —O—(C$_{1-8}$ alkyl), —O—(C$_{2-8}$ alkenyl), —O—(C$_{2-8}$ alkynyl), —O— cycloalkyl, —O-heterocycloalkyl, —O-aryl, —O-heteroaryl, —N(R$^{71}$)—(C$_{1-8}$ alkyl), —N(R$^{71}$)—(C$_{2-8}$ alkenyl), —N(R$^{71}$)—(C$_{2-8}$ alkynyl), —N(R$^{71}$)-cycloalkyl, —N(R$^{71}$)-heterocycloalkyl, —N(R$^{71}$)-aryl, and —N(R$^{71}$)-heteroaryl, wherein said C$_{1-8}$ alkyl or the C$_{1-8}$ alkyl moiety comprised in any of the aforementioned groups, said C$_{2-8}$ alkenyl or the C$_{2-8}$ alkenyl moiety comprised in any of the aforementioned groups, and said C$_{2-8}$ alkynyl or the C$_{2-8}$ alkynyl moiety comprised in any of the aforementioned groups are each optionally substituted with one or more groups R$^{72}$, and further wherein said cycloalkyl or the cycloalkyl moiety comprised in any of the aforementioned groups, said heterocycloalkyl or the heterocycloalkyl moiety comprised in any of the aforementioned groups, said aryl or the aryl moiety comprised in any of the aforementioned groups, and said heteroaryl or the heteroaryl moiety comprised in any of the aforementioned groups are each optionally substituted with one or more groups R$^{73}$.

Each R$^{71}$ is independently selected from hydrogen and C$_{1-8}$ alkyl.

Each R$^{72}$ is independently selected from —OH, —O(C$_{1-8}$ alkyl), —SH, —S(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH(C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl).

Each R$^{73}$ is independently selected from C$_{1-8}$ alkyl, C$_{2-8}$ alkenyl, C$_{2-8}$ alkynyl, —(C$_{0-3}$ alkylene)-OH, —(C$_{0-3}$ alkylene)-O(C$_{1-8}$ alkyl), —(C$_{0-3}$ alkylene)-SH, —(C$_{0-3}$ alkylene)-S(C$_{1-8}$ alkyl), —(C$_{0-3}$ alkylene)-NH$_2$, —(C$_{0-3}$ alkylene)-NH(C$_{1-8}$ alkyl), —(C$_{0-3}$ alkylene)-N(C$_{1-8}$ alkyl)(C$_{1-8}$ alkyl), —(C$_{0-3}$ alkylene)-halogen, —(C$_{0-3}$ alkylene)-(C$_{1-8}$ haloalkyl), —(C$_{0-3}$ alkylene)-CF$_3$, —(C$_{0-3}$ alkylene)-CN, —(C$_{0-3}$ alkylene)-CHO, —(C$_{0-3}$ alkylene)-CO—(C$_{1-8}$ alkyl), —(C$_{0-3}$ alkylene)-COOH, —(C$_{0-3}$ alkylene)-CO—O—(C$_{1-8}$ alkyl), —(C$_{0-3}$ alkylene)-O—CO—(C$_{1-8}$ alkyl), —(C$_{0-3}$ alkylene)-CO—NH$_2$, —(C$_{0-3}$ alkylene)-CO—NH(C$_{1-8}$ alkyl), —(C$_{0-3}$ alkylene)-CO—N(C$_{1-8}$ alkyl)(C$_{1-8}$ alkyl), —(C$_{0-3}$ alkylene)-NH—CO—(C$_{1-8}$ alkyl), —(C$_{0-3}$ alkylene)-N(C$_{1-8}$ alkyl)-CO—(C$_{1-8}$ alkyl), —(C$_{0-3}$ alkylene)-SO$_2$—NH$_2$, —(C$_{0-3}$ alkylene)-SO$_2$—NH(C$_{1-8}$ alkyl), —(C$_{0-3}$ alkylene)-SO$_2$—N(C$_{1-8}$ alkyl)(C$_{1-8}$ alkyl), —(C$_{0-3}$ alkylene)-NH—SO$_2$—(C$_{1-8}$ alkyl), and —(C$_{0-3}$ alkylene)-N(C$_{1-8}$ alkyl)-SO$_2$—(C$_{1-8}$ alkyl).

Each R$^8$ is independently selected from C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH(C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl).

Each R$^9$ is independently selected from C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-}$ alkyl), —O—CO—($C_{1-8}$ alkyl), —CO—$NH_2$, —CO—NH ($C_{1-8}$ alkyl), —CO—N($C_{1-8}$ alkyl)($C_{1-8}$ alkyl), —NH—CO—($C_{1-8}$ alkyl), —N($C_{1-8}$ alkyl)-CO—($C_{1-8}$ alkyl), —$SO_2$—$NH_2$, —$SO_2$—NH($C_{1-8}$ alkyl), —$SO_2$—N($C_{1-8}$ alkyl)($C_{1-8}$ alkyl), —NH—$SO_2$—($C_{1-8}$ alkyl), and —N($C_{1-8}$ alkyl)-$SO_2$—($C_{1-8}$ alkyl).

n is an integer of 0 to 8.

m is an integer of 0 to 6.

The present invention also relates to a pharmaceutical composition comprising a compound of formula (I) or a pharmaceutically acceptable salt or solvate thereof, in combination with a pharmaceutically acceptable excipient. Accordingly, the invention relates to a compound of formula (I) or a pharmaceutically acceptable salt or solvate thereof, or a pharmaceutical composition comprising any of the aforementioned entities and a pharmaceutically acceptable excipient, for use as a medicament.

The invention further relates to a compound of formula (I) or a pharmaceutically acceptable salt or solvate thereof, or a pharmaceutical composition comprising any of the aforementioned entities and a pharmaceutically acceptable excipient, for use in the treatment or prevention of cancer.

Moreover, the present invention relates to the use of a compound of formula (I) or a pharmaceutically acceptable salt or solvate thereof in the preparation of a medicament for the treatment or prevention of cancer.

The invention likewise relates to a method of treating or preventing cancer, the method comprising administering a compound of formula (I) or a pharmaceutically acceptable salt or solvate thereof, or a pharmaceutical composition comprising any of the aforementioned entities in combination with a pharmaceutically acceptable excipient, to a subject (preferably a human) in need thereof.

It will be understood that a therapeutically effective amount of the compound of formula (I) or the pharmaceutically acceptable salt or solvate thereof, or of the pharmaceutical composition, is to be administered in accordance with this method.

The cancer to be treated or prevented in accordance with the present invention is preferably selected from gastrointestinal cancer, colorectal cancer (e.g., McLean et al. or Goldenstein et al. both *Clin Colorectal Cancer.* 2015), colon cancer, liver cancer (e.g., hepatocellular carcinoma), pancreatic cancer (e.g., Cid-Arregui et al. *World J Gastroenterol.* 2015), biliary tract cancer (e.g., Yang R et al. *Anticancer Drugs* 2013), stomach cancer, genitourinary cancer, bladder cancer, testicular cancer, cervical cancer, malignant mesothelioma, osteogenic sarcoma, esophageal cancer, laryngeal cancer, prostate cancer (e.g., hormone-refractory prostate cancer), lung cancer (e.g., small cell lung cancer or non-small cell lung cancer), breast cancer (e.g., triple-negative breast cancer, or breast cancer having a BRCA1 and/or BRCA2 gene mutation), hematological cancer, leukemia (e.g., acute lymphoblastic leukemia, acute myeloid leukemia, chronic lymphocytic leukemia, or chronic myeloid leukemia), lymphoma (e.g., Hodgkin lymphoma or non-Hodgkin lymphoma, such as, e.g., follicular lymphoma or diffuse large B-cell lymphoma), ovarian cancer (e.g., Bogliolo et al. *Expert Opin Investig Drugs.* 2015), brain cancer, neuroblastoma, Ewing's sarcoma, kidney cancer, epidermoid cancer, skin cancer, melanoma, head and/or neck cancer (e.g., head and neck squamous cell carcinoma), and mouth cancer. The cancer to be treated or prevented in accordance with the invention may also be a gynecological cancer, such as, e.g., cervical cancer, ovarian cancer (e.g., ovarian carcinoma), uterine cancer, vaginal cancer, or vulvar cancer, particularly endometrial cancer. The cancer to be treated or prevented may further be, e.g., hepatobiliary cancer, thymoma, Merkel-cell cancer, anal cancer (particularly anal squamous cell carcinoma), or a neuroendocrine cancer. The present invention relates, in particular, to the treatment or prevention of colorectal cancer, colon cancer, pancreatic cancer, lung cancer (particularly non-small cell lung cancer), ovarian cancer (particularly ovarian carcinoma), bladder cancer, cervical cancer, malignant mesothelioma, melanoma, head and/or neck cancer (particularly head and neck squamous cell carcinoma), or testicular cancer. Even more preferably, the cancer to be treated or prevented in accordance with the present invention is colorectal cancer, colon cancer, pancreatic cancer, lung cancer (particularly non-small cell lung cancer), ovarian cancer (particularly ovarian carcinoma), cervical cancer, melanoma, or head and/or neck cancer (particularly head and neck squamous cell carcinoma). Accordingly, the cancer to be treated or prevented may thus be, for example, ovarian cancer (particularly ovarian carcinoma), lung cancer (particularly non-small cell lung cancer), or head and/or neck cancer (particularly head and neck squamous cell carcinoma). Yet even more preferably, the cancer to be treated or prevented in accordance with the present invention is colorectal cancer, colon cancer, or pancreatic cancer.

The compounds of formula (I) will be described in more detail in the following:

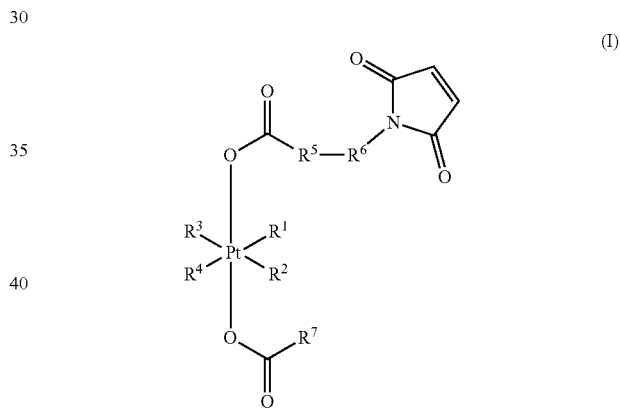

(I)

or a pharmaceutically acceptable salt or solvate thereof.

In formula (I), $R^1$ and $R^2$ are joined together to form a moiety (A1), (A2) or (A3):

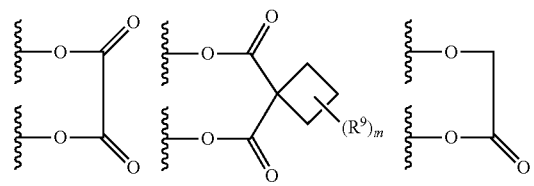

Preferably, $R^1$ and $R^2$ are joined together to form a moiety (A1) or (A2). More preferably, $R^1$ and $R^2$ are joined together to form a moiety (A1).

$R^3$ and $R^4$ are joined together to form a moiety (1), or $R^3$ is a moiety (B2) and $R^4$ is —$NH_3$, or $R^3$ and $R^4$ are each —$NH_3$:

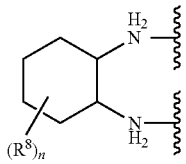
(B1)

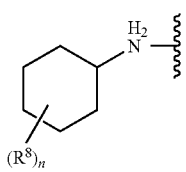
(B2)

Preferably, R³ and R⁴ are joined together to form a moiety (1), or R³ and R⁴ are each —NH₃. More preferably, R³ and R⁴ are joined together to form a moiety (1).

It is preferred that R¹, R², R³ and R⁴ are selected so as to provide a compound of formula (I) having any one of the following structures:

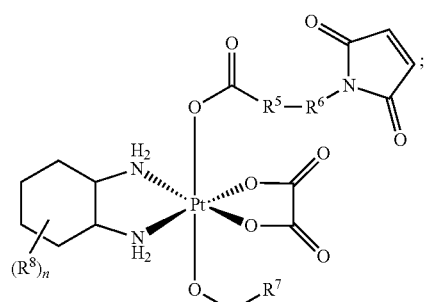

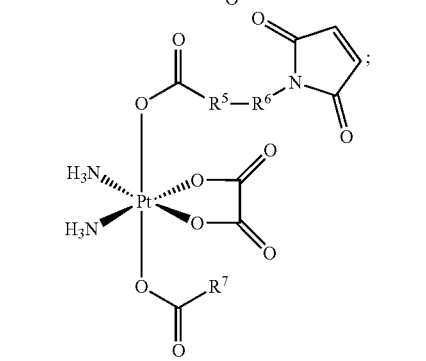

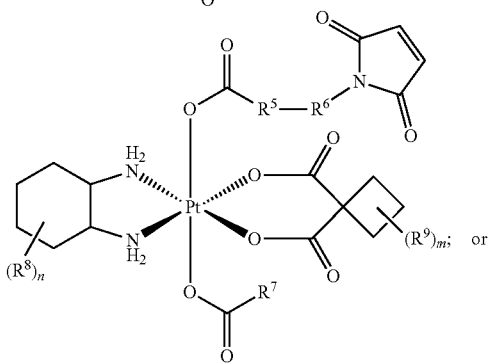

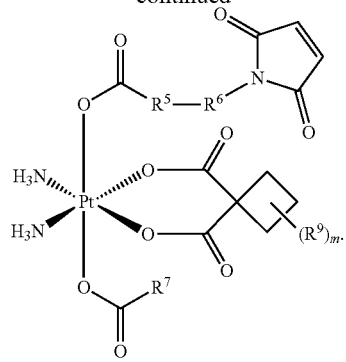

It is particularly preferred that either $R^1$ and $R^2$ are joined together to form a moiety (A1) and $R^3$ and $R^4$ are joined together to form a moiety (B31), or $R^1$ and $R^2$ are joined together to form a moiety (A2) and $R^3$ and $R^4$ are each —NH₃. Most preferably, $R^1$ and $R^2$ are joined together to form a moiety (A1) and $R^3$ and $R^4$ are joined together to form a moiety (B31).

It is furthermore preferred that the two asymmetric carbon atoms of the cyclohexyl ring comprised in moiety (E1) both have the R-configuration, i.e. that the cyclohexane-1,2-diamine group in moiety (E1) is present as (1R,2R)-cyclohexane-1,2-diamine, as illustrated in the following:

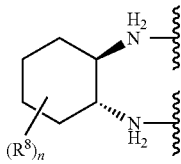

$R^5$ is —N($R^{51}$)— or —CH₂—. Preferably, $R^5$ is —N($R^{51}$)—.

$R^{51}$ is hydrogen or $C_{1-8}$ alkyl. Preferably, $R^{51}$ is hydrogen or $C_{1-5}$ alkyl. More preferably, $R^{51}$ is hydrogen, methyl, or ethyl. Even more preferably, $R^{51}$ is hydrogen.

In accordance with the meanings of $R^5$ and $R^{51}$ described above, it is particularly preferred that $R^5$ is —NH—, —N(—CH₃)— or —N(—CH₂CH₃)—, and most preferably $R^5$ is —NH—.

$R^6$ is $C_{1-8}$ alkylene, wherein one or two —CH₂— units comprised in said $C_{1-8}$ alkylene are each optionally replaced by a group independently selected from —O—, —CO—, —C(=O)O—, —O—C(=O)—, —N($R^{61}$)—, —N($R^{61}$)—CO—, —CO—N($R^{61}$)—, arylene, and heteroarylene, wherein said arylene and said heteroarylene are each optionally substituted with one or more (e.g., one, two, three, or four) groups $R^{62}$. Preferably, $R^6$ is $C_{1-8}$ alkylene, wherein one or two —CH₂— units comprised in said $C_{1-8}$ alkylene are each optionally replaced by a group independently selected from —O—, —CO—, —C(=O)O—, —O—C(=O)—, —N($R^{61}$)—, —N($R^{61}$)—CO—, and —CO—N($R^{61}$)—. More preferably, $R^6$ is $C_{1-8}$ alkylene, wherein one —CH₂— unit comprised in said $C_{1-8}$ alkylene is optionally replaced by a group selected from —O—, —CO—, —C(=O)O—, —O—C(=O)—, —N($R^{61}$)—, —N($R^{61}$)—CO—, and —CO—N($R^{61}$)—. Even more preferably, $R^6$ is $C_{1-8}$ alkylene (such as, e.g., —CH₂—, —(CH₂)₂—, —(CH₂)₃—, —(CH₂)₄—, —(CH₂)₅—, —(CH₂)₆—, —(CH₂)₇—, or —(CH₂)₈—). Even more preferably, $R^6$ is $C_{1-5}$ alkylene. Yet even more preferably, $R^6$ is selected from —$CH_2$—, —$(CH_2)_2$—, —$(CH_2)_3$—, —$(CH_2)_4$—, and —$(CH_2)$—. Still more preferably, $R^6$ is selected from —$CH_2$—, —$(CH_2)_2$—, and —$(CH_2)_3$—. Most preferably, $R^6$ is —$(CH_2)_2$—.

Each $R^{61}$ is independently selected from hydrogen and $C_{1-8}$ alkyl. Preferably, each $R^{61}$ is independently selected from hydrogen and $C_{1-5}$ alkyl. More preferably, each $R^{61}$ is independently selected from hydrogen, methyl, and ethyl. Even more preferably, each $R^{61}$ is hydrogen.

Each $R^{62}$ is independently selected from $C_{1-8}$ alkyl, $C_{2-8}$ alkenyl, $C_{2-8}$ alkynyl, —$(C_{0-3}$ alkylene)-OH, —$(C_{0-3}$ alkylene)-O($C_{1-8}$ alkyl), —$(C_{0-3}$ alkylene)-SH, —$(C_{0-3}$ alkylene)-S($C_{1-8}$ alkyl), —$(C_{0-3}$ alkylene)-$NH_2$, —$(C_{0-3}$ alkylene)-NH($C_{1-8}$ alkyl), —$(C_{0-3}$ alkylene)-N($C_{1-8}$ alkyl)($C_{1-8}$ alkyl), —$(C_{0-3}$ alkylene)-halogen, —$(C_{0-3}$ alkylene)-($C_{1-8}$ haloalkyl), —$(C_{0-3}$ alkylene)-$CF_3$, —$(C_{0-3}$ alkylene)-CN, —$(C_{0-3}$ alkylene)-CHO, —$(C_{0-3}$ alkylene)-CO—($C_{1-8}$ alkyl), —$(C_{0-3}$ alkylene)-COOH, —$(C_{0-3}$ alkylene)-CO—O—($C_{1-8}$ alkyl), —$(C_{0-3}$ alkylene)-O—CO—($C_{1-8}$ alkyl), —$(C_{0-3}$ alkylene)-CO—$NH_2$, —$(C_{0-3}$ alkylene)-CO—NH($C_{1-8}$ alkyl), —$(C_{0-3}$ alkylene)-CO—N($C_{1-8}$ alkyl)($C_{1-8}$ alkyl), —$(C_{0-3}$ alkylene)-NH—CO—($C_{1-8}$ alkyl), —$(C_{0-3}$ alkylene)-N($C_{1-8}$ alkyl)-CO—($C_{1-8}$ alkyl), —$(C_{0-3}$ alkylene)-$SO_2$—$NH_2$, —$(C_{0-3}$ alkylene)-$SO_2$—NH($C_{1-8}$ alkyl), —$(C_{0-3}$ alkylene)-$SO_2$—N($C_{1-8}$ alkyl)($C_{1-8}$ alkyl), —$(C_{0-3}$ alkylene)-NH—$SO_2$—($C_{1-8}$ alkyl), and —$(C_{0-3}$ alkylene)-N($C_{1-8}$ alkyl)-$SO_2$—($C_{1-8}$ alkyl). Preferably, each $R^{62}$ is independently selected from $C_{1-5}$ alkyl, $C_{2-5}$ alkenyl, $C_{2-5}$ alkynyl, —OH, —O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), and —N($C_{1-5}$ alkyl)-$SO_2$—($C_{1-5}$ alkyl). More preferably, each $R^{62}$ is independently selected from $C_{1-5}$ alkyl, $C_{2-5}$ alkenyl, $C_{2-5}$ alkynyl, —OH, —O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. Even more preferably, each $R^{62}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

$R^7$ is selected from hydrogen, $C_{1-8}$ alkyl, $C_{2-8}$ alkenyl, $C_{2-8}$ alkynyl, cycloalkyl, heterocycloalkyl, aryl, heteroaryl, —O—($C_{1-8}$ alkyl), —O—($C_{2-8}$ alkenyl), —O—($C_{2-8}$ alkynyl), —O-cycloalkyl, —O-heterocycloalkyl, —O-aryl, —O-heteroaryl, —N($R^{71}$)—($C_{1-8}$ alkyl), —N($R^{71}$)—($C_{2-8}$ alkenyl), —N($R^{71}$)—($C_{2-8}$ alkynyl), —N($R^{71}$)-cycloalkyl, —N($R^{71}$)-heterocycloalkyl, —N($R^{71}$)-aryl, and —N($R^{71}$)-heteroaryl, wherein said $C_{1-8}$ alkyl or the $C_{1-8}$ alkyl moiety comprised in any of the aforementioned groups (e.g., the $C_{1-8}$ alkyl moiety comprised in said —O—($C_{1-8}$ alkyl)), said $C_{2-8}$ alkenyl or the $C_{2-8}$ alkenyl moiety comprised in any of the aforementioned groups, and said $C_{2-8}$ alkynyl or the $C_{2-8}$ alkynyl moiety comprised in any of the aforementioned groups are each optionally substituted with one or more (e.g., one, two, or three) groups $R^{72}$, and further wherein said cycloalkyl or the cycloalkyl moiety comprised in any of the aforementioned groups (e.g., the cycloalkyl moiety comprised in said —O-cycloalkyl), said heterocycloalkyl or the heterocycloalkyl moiety comprised in any of the aforementioned groups, said aryl or the aryl moiety comprised in any of the aforementioned groups, and said heteroaryl or the heteroaryl moiety comprised in any of the aforementioned groups are each optionally substituted with one or more (e.g., one, two, three, or four) groups $R^{73}$. Preferably, $R^7$ is selected from hydrogen, $C_{1-8}$ alkyl, $C_{2-8}$ alkenyl, $C_{2-8}$ alkynyl, cycloalkyl, heterocycloalkyl, aryl (e.g., phenyl), heteroaryl, —O—($C_{1-8}$ alkyl), —O—($C_{2-8}$ alkenyl), —O—($C_{2-8}$ alkynyl), —O-cycloalkyl, —O-heterocycloalkyl, —O-aryl, and —O-heteroaryl, wherein said $C_{1-8}$ alkyl, said $C_{2-8}$ alkenyl, said $C_{2-8}$ alkynyl, the $C_{1-8}$ alkyl moiety comprised in said —O—($C_{1-8}$ alkyl), the $C_{2-8}$ alkenyl moiety comprised in said —O—($C_{2-8}$ alkenyl), and the $C_{2-8}$ alkynyl moiety comprised in said —O—($C_{2-8}$ alkynyl) are each optionally substituted with one or more (e.g., one, two, or three) groups $R^{72}$, and further wherein said cycloalkyl, said heterocycloalkyl, said aryl, said heteroaryl, the cycloalkyl moiety comprised in said —O-cycloalkyl, the heterocycloalkyl moiety comprised in said —O-heterocycloalkyl, the aryl moiety comprised in said —O-aryl, and the heteroaryl moiety comprised in said —O-heteroaryl are each optionally substituted with one or more (e.g., one, two, three, or four) groups $R^{73}$. More preferably, $R^7$ is selected from $C_{1-8}$ alkyl, $C_{2-8}$ alkenyl, and $C_{2-8}$ alkynyl. Even more preferably, $R^7$ is $C_{1-8}$ alkyl. Yet even more preferably, $R^7$ is $C_{1-5}$ alkyl. Still more preferably, $R^7$ is selected from —$CH_3$, —$CH_2CH_3$, —$(CH_2)_2$—$CH_3$, —$(CH_2)_3$—$CH_3$, and —$(CH_2)_4$—$CH_3$. Most preferably, $R^7$ is —$CH_3$.

Each $R^{71}$ is independently selected from hydrogen and $C_{1-8}$ alkyl. Preferably, each $R^{71}$ is independently selected from hydrogen and $C_{1-5}$ alkyl. More preferably, each $R^{71}$ is independently selected from hydrogen, methyl, and ethyl. Even more preferably, each $R^{71}$ is hydrogen.

Each $R^{72}$ is independently selected from —OH, —O($C_{1-8}$ alkyl), —SH, —S($C_{1-8}$ alkyl), —$NH_2$, —NH($C_{1-8}$ alkyl), —N($C_{1-8}$ alkyl)($C_{1-8}$ alkyl), halogen, $C_{1-8}$ haloalkyl, —$CF_3$, —CN, —CHO, —CO—($C_{1-8}$ alkyl), —COOH, —CO—O—($C_{1-8}$ alkyl), —O—CO—($C_{1-8}$ alkyl), —CO—$NH_2$, —CO—NH($C_{1-8}$ alkyl), —CO—N($C_{1-8}$ alkyl)($C_{1-8}$ alkyl), —NH—CO—($C_{1-8}$ alkyl), —N($C_{1-8}$ alkyl)-CO—($C_{1-8}$ alkyl), —$SO_2$—$NH_2$, —$SO_2$—NH($C_{1-8}$ alkyl), —$SO_2$—N($C_{1-8}$ alkyl)($C_{1-8}$ alkyl), —NH—$SO_2$—($C_{1-8}$ alkyl), and —N($C_{1-8}$ alkyl)-$SO_2$—($C_{1-8}$ alkyl). Preferably, each $R^{72}$ is independently selected from —OH, —O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. More preferably, each $R^{72}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_4$ alkyl)($C_{1-4}$ alkyl) (e.g., —$N(CH_3)_2$), halogen (e.g., —F, —Cl, —Br, or —I), —$CF_3$, and —CN.

Each $R^{73}$ is independently selected from $C_{1-8}$ alkyl, $C_{2-8}$ alkenyl, $C_{2-8}$ alkynyl, —$(C_{0-3}$ alkylene)-OH, —$(C_{0-3}$ alkylene)-O($C_{1-8}$ alkyl), —$(C_{0-3}$ alkylene)-SH, —$(C_{0-3}$ alkylene)-S($C_{1-8}$ alkyl), —$(C_{0-3}$ alkylene)-$NH_2$, —$(C_{0-3}$ alkylene)-NH($C_{1-8}$ alkyl), —$(C_{0-3}$ alkylene)-N($C_{1-8}$ alkyl)($C_{1-8}$ alkyl), —$(C_{0-3}$ alkylene)-halogen, —$(C_{0-3}$ alkylene)-($C_{1-8}$ haloalkyl), —$(C_{0-3}$ alkylene)-$CF_3$, —$(C_{0-3}$ alkylene)-CN, —$(C_{0-3}$ alkylene)-CHO, —$(C_{0-3}$ alkylene)-CO—($C_{1-8}$ alkyl), —$(C_{0-3}$ alkylene)-COOH, —$(C_{0-3}$ alkylene)-CO—O—($C_{1-8}$ alkyl), —$(C_{0-3}$ alkylene)-O—CO—($C_{1-8}$ alkyl), —$(C_{0-3}$ alkylene)-CO—$NH_2$, —$(C_{0-3}$ alkylene)-CO—NH($C_{1-8}$ alkyl), —$(C_{0-3}$ alkylene)-CO—N($C_{1-8}$ alkyl)($C_{1-8}$ alkyl), —$(C_{0-3}$ alkylene)-NH—CO—($C_{1-8}$ alkyl), —$(C_{0-3}$ alkylene)-N($C_{1-8}$ alkyl)-CO—($C_{1-8}$ alkyl), —$(C_{0-3}$ alkylene)-$SO_2$—$NH_2$, —$(C_{0-3}$ alkylene)-$SO_2$—NH($C_{1-8}$ alkyl), —$(C_{0-3}$ alkylene)-$SO_2$—N($C_{1-8}$ alkyl)($C_{1-8}$ alkyl), —(C$_{0-3}$ alkylene)-NH—SO$_2$—(C$_{1-8}$ alkyl), and —(C$_{0-3}$ alkylene)-N(C$_{1-8}$ alkyl)-SO$_2$—(C$_{1-8}$ alkyl). Preferably, each R$^{73}$ is independently selected from C$_{1-5}$ alkyl, C$_{2-5}$ alkenyl, C$_{2-5}$ alkynyl, —OH, —O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, —CN, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), and —N(C$_{1-5}$ alkyl)-SO$_2$—(C$_{1-5}$ alkyl). More preferably, each R$^{73}$ is independently selected from C$_{1-5}$ alkyl, C$_{2-5}$ alkenyl, C$_{2-5}$ alkynyl, —OH, —O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN. Even more preferably, each R$^{73}$ is independently selected from C$_{1-4}$ alkyl (e.g., methyl or ethyl), —OH, —O(C$_{1-4}$ alkyl) (e.g., —OCH$_3$ or —OCH$_2$CH$_3$), —NH$_2$, —NH(C$_{1-4}$ alkyl) (e.g., —NHCH$_3$), —N(C$_{1-4}$ alkyl)(C$_{1-4}$ alkyl) (e.g., —N(CH$_3$)$_2$), halogen (e.g., —F, —C, —Br, or —I), —CF$_3$, and —CN.

Each R$^8$ is independently selected from C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH(C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl). Preferably, each R$^8$ is independently selected from C$_{1-8}$ alkyl, C$_{2-8}$ alkenyl, and C$_{2-8}$ alkynyl. More preferably, each R$^8$ is independently C$_{1-8}$ alkyl. Even more preferably, each R$^8$ is independently C$_{1-4}$ alkyl (e.g., methyl or ethyl).

For example, the moiety (1) may carry one methyl substituent (i.e., n is 1, and R$^8$ is methyl), particularly in the 4-position of the cyclohexyl ring, as shown in the following:

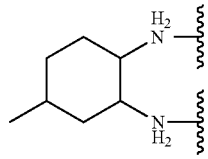

Any substituent R$^8$, if present, may have the R-configuration or the S-configuration. For example, if the moiety (E1) carries one methyl substituent, particularly in the 4-position of the cyclohexyl ring (as described above), this methyl substituent may have the R-configuration or the S-configuration. Thus, moiety (E1) may be, e.g., a (1R,2R,4R)-4-methyl-cyclohexane-1,2-diamine moiety or a (1R,2R,4S)-4-methyl-cyclohexane-1,2-diamine moiety.

Each R$^9$ is independently selected from C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH(C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl). Preferably, each R$^9$ is independently selected from C$_{1-8}$ alkyl, C$_{2-8}$ alkenyl, and C$_{2-8}$ alkynyl. More preferably, each R$^9$ is independently C$_{1-8}$ alkyl. Even more preferably, each R$^9$ is independently C$_{1-4}$ alkyl (e.g., methyl or ethyl).

n is an integer of 0 to 8. Preferably, n is an integer of 0 to 6. More preferably, n is 0, 1, 2, 3, or 4. Even more preferably, n is 0, 1, or 2. Yet even more preferably, n is 0 or 1. Most preferably, n is 0.

m is an integer of 0 to 6. More preferably, m is 0, 1, 2, 3, or 4. Even more preferably, m is 0, 1, or 2. Yet even more preferably, m is 0 or 1. Most preferably, m is 0.

It is to be understood that n indicates the number of substituents R$^8$ that are bound to the corresponding cyclohexyl ring, e.g., the cyclohexyl ring comprised in moiety (1) or (B2) or in formula (Ia). If n is 0, then this cyclohexyl ring is not substituted with any group R$^8$, i.e. is substituted with hydrogen instead of R$^8$. Likewise, it is to be understood that m indicates the number of substituents R$^9$ that are bound to the cyclobutyl ring comprised in moiety (A2). If m is 0, then this cyclobutyl ring is unsubstituted, i.e. is substituted with hydrogen instead of R$^9$.

Exemplary compounds of formula (I) are the following compounds KP2299, 17, 18, 19, 20, 21, 22, 23, 24, 31, 32, 33, 34, 35, 36, 37, 38, 39, 40, 41 and 42 as well as pharmaceutically acceptable salts or solvates of any of these compounds:

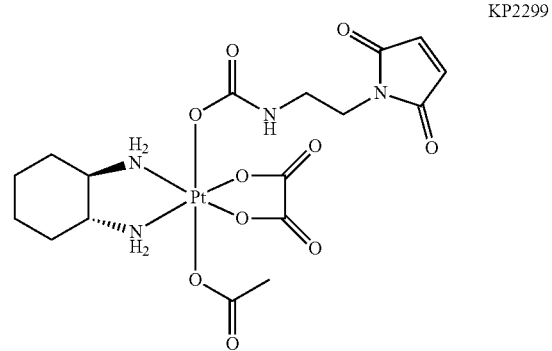

KP2299

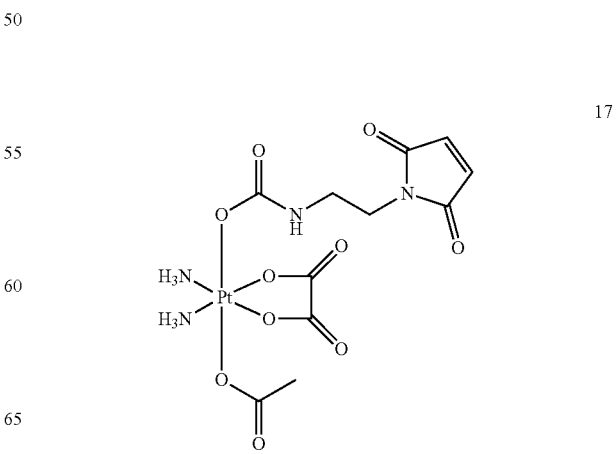

17

18
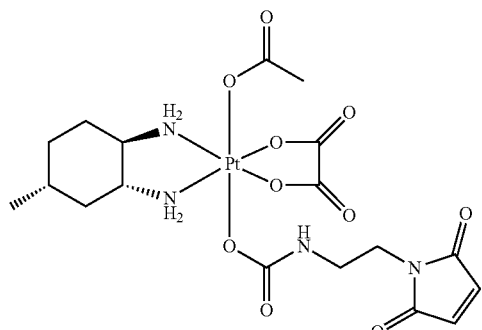
19
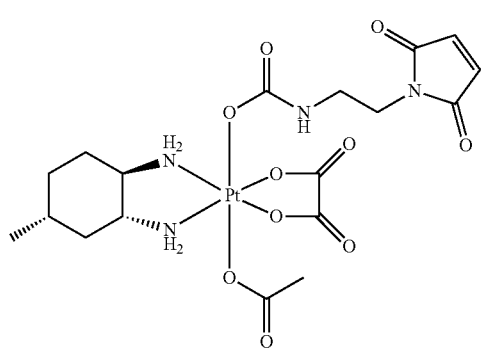
20
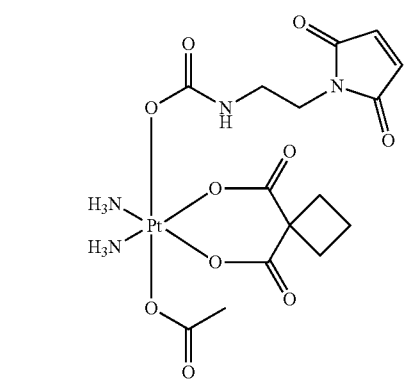
21
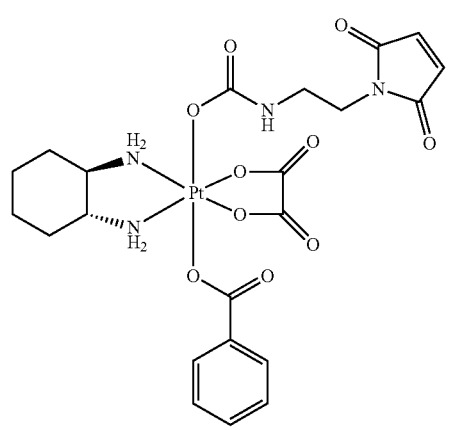
22
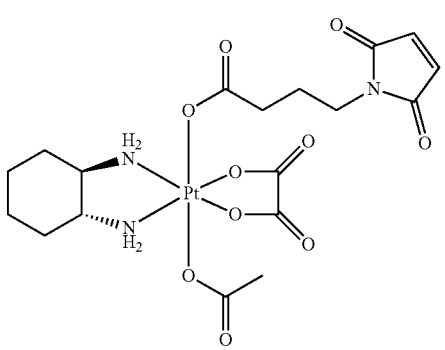
23
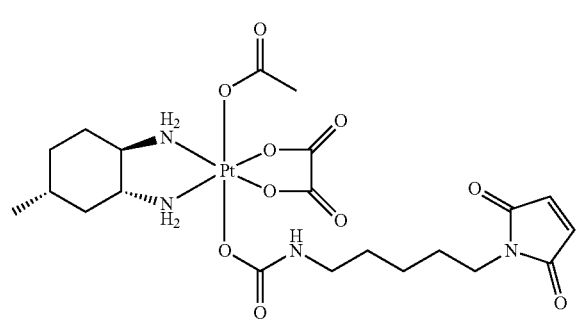
24
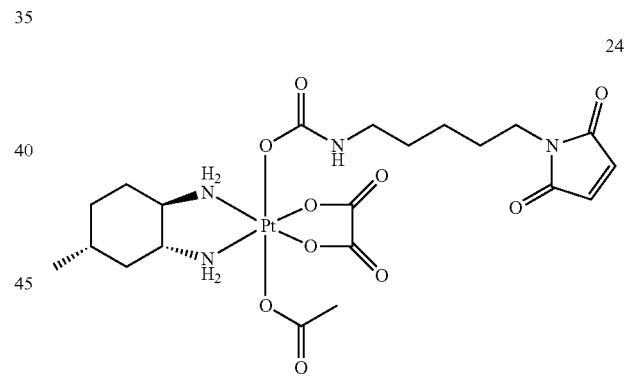
31
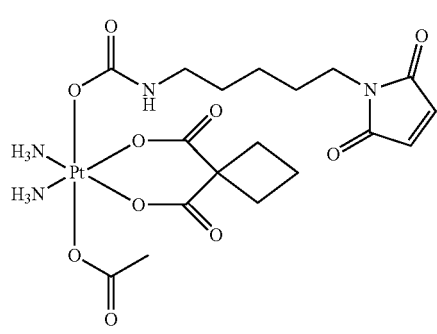

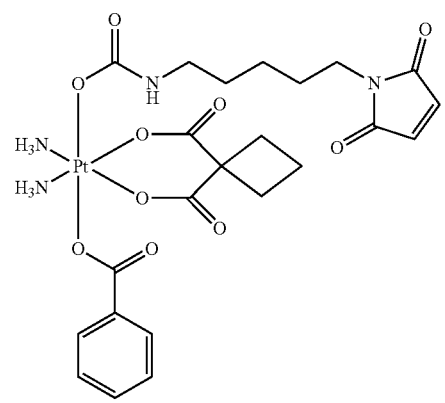
32
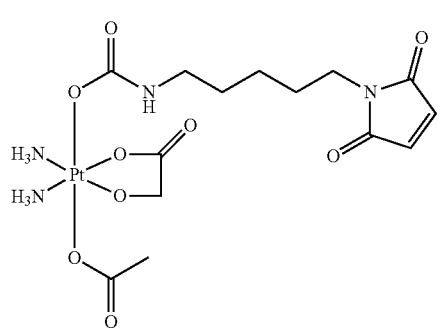
36
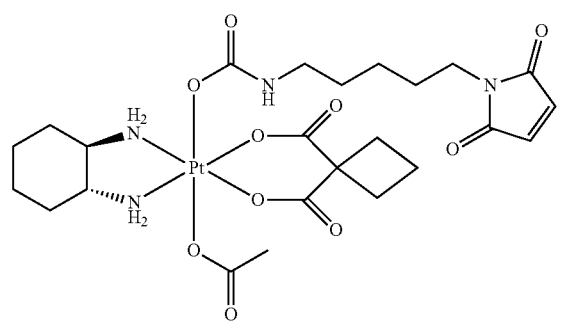
33
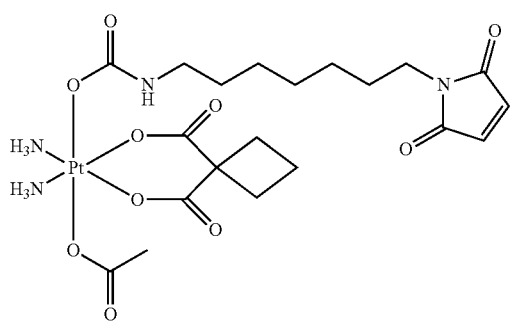
37
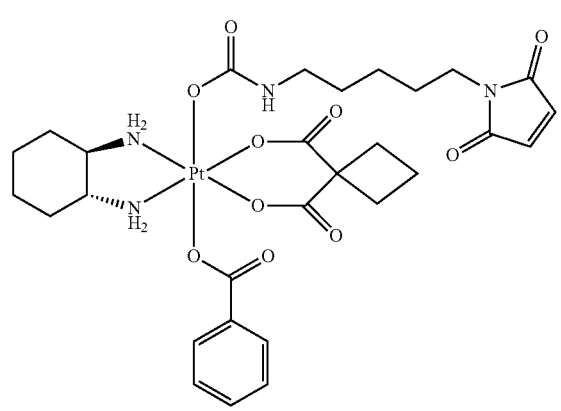
34
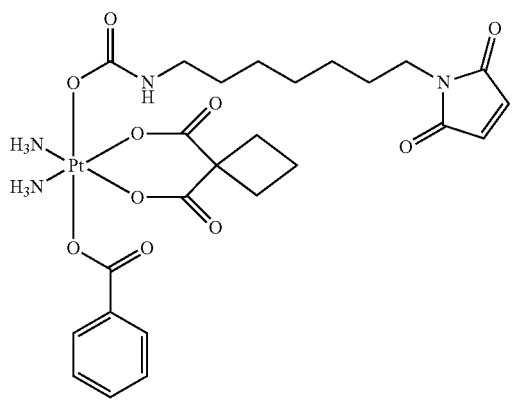
38
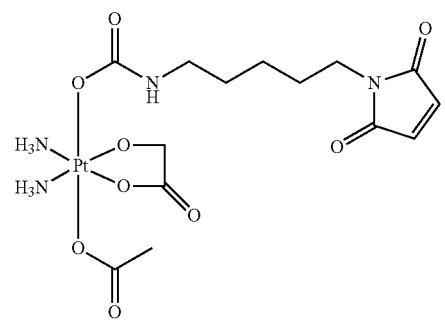
35
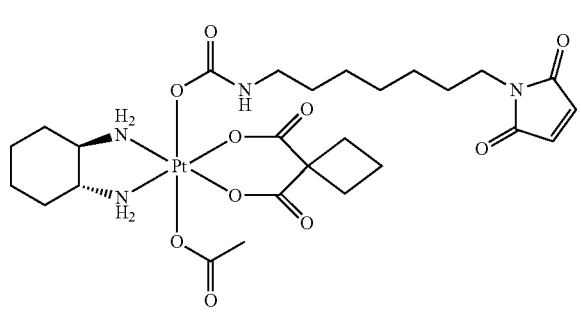
39

-continued

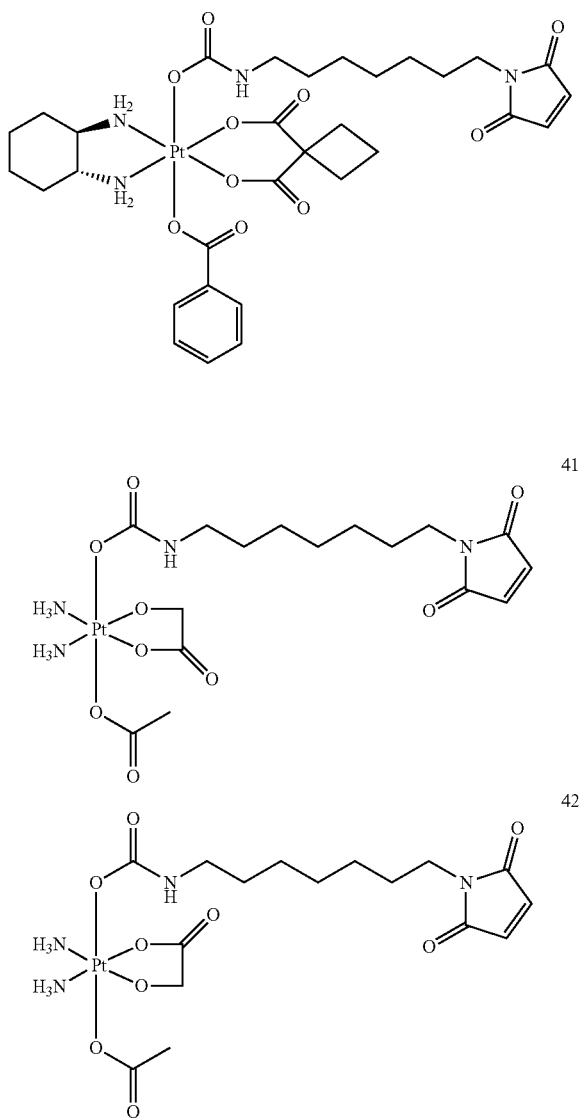

In a particularly preferred embodiment, the compound of formula (I) is a compound of the following formula (Ia) or a pharmaceutically acceptable salt or solvate thereof:

(Ia)

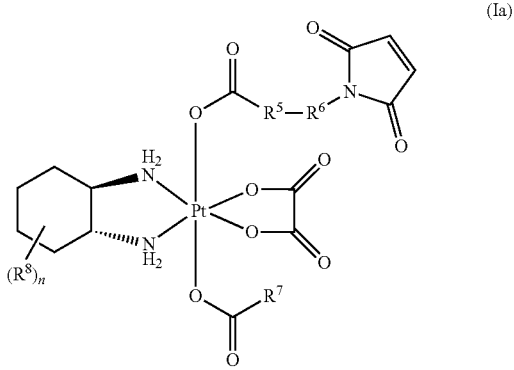

wherein the groups and variables in formula (Ia), including in particular $R^5$, $R^6$, $R^7$, $R^8$ and n, have the same meanings, including the same preferred meanings, as described and defined herein above for the compound of formula (I).

In an even more preferred embodiment, the compound of formula (I) is a compound of the following formula (Ib) or a pharmaceutically acceptable salt or solvate thereof:

(Ib)

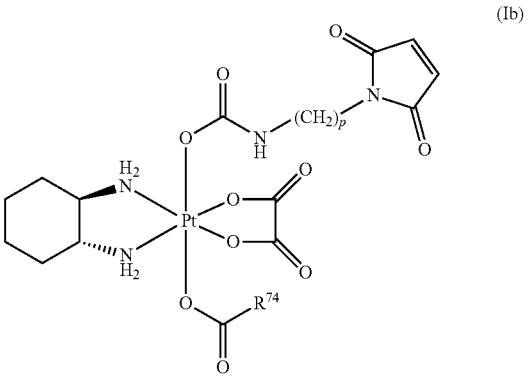

In formula (Ib), $R^{74}$ is selected from hydrogen, $C_{1-8}$ alkyl, $C_{2-8}$ alkenyl, $C_{2-8}$ alkynyl, cycloalkyl, heterocycloalkyl, aryl, heteroaryl, —O—($C_{1-8}$ alkyl), —O—($C_{2-8}$ alkenyl), —O—($C_{2-8}$ alkynyl), —O-cycloalkyl, —O-heterocycloalkyl, —O-aryl, and —O-heteroaryl, wherein said $C_{1-8}$ alkyl, said $C_{2-8}$ alkenyl, said $C_{2-8}$ alkynyl, the $C_{1-8}$ alkyl moiety comprised in said —O—($C_{1-8}$ alkyl), the $C_{2-8}$ alkenyl moiety comprised in said —O—($C_{2-8}$ alkenyl), and the $C_{2-8}$ alkynyl moiety comprised in said —O—($C_{2-8}$ alkynyl) are each optionally substituted with one or more (e.g., one, two, or three) groups $R^{72}$, and further wherein said cycloalkyl, said heterocycloalkyl, said aryl, said heteroaryl, the cycloalkyl moiety comprised in said —O-cycloalkyl, the heterocycloalkyl moiety comprised in said —O-heterocycloalkyl, the aryl moiety comprised in said —O-aryl, and the heteroaryl moiety comprised in said —O-heteroaryl are each optionally substituted with one or more (e.g., one, two, three, or four) groups $R^{73}$. The groups $R^{72}$ and $R^{73}$ have the same meanings, including the same preferred meanings, as described and defined herein above for the compound of formula (I).

Preferably, $R^{74}$ is selected from $C_{1-8}$ alkyl, $C_{2-8}$ alkenyl, and $C_{2-8}$ alkynyl. More preferably, $R^{74}$ is $C_{1-8}$ alkyl. Even more preferably, $R^{74}$ is $C_{1-5}$ alkyl. Yet even more preferably, $R^{74}$ is selected from —$CH_3$, —$CH_2CH_3$, —$(CH_2)_2$—$CH_3$, —$(CH_2)_3$—$CH_3$, and —$(CH_2)_4$—$CH_3$. Most preferably, $R^{74}$ is —$CH_3$.

p is an integer of 1 to 8. Preferably, p is 1, 2, 3, 4, or 5. More preferably, p is 1, 2, or 3. Even more preferably, p is 2.

A particularly preferred compound of formula (I), (Ia) or (Ib) is the following compound (which is also referred as "KP2299" in this specification):

KP2299

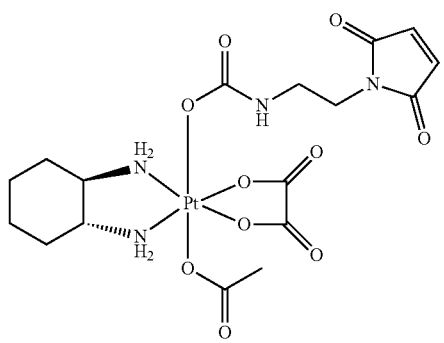

or a pharmaceutically acceptable salt or solvate thereof.

In a further specific embodiment, the compound of formula (I) is a compound of the following formula (Ic) or a pharmaceutically acceptable salt or solvate thereof:

(Ic)

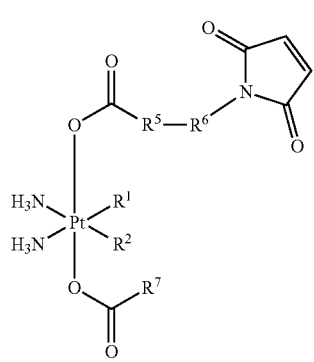

wherein the groups $R^1$ and $R^2$ in formula (Ic) are joined together to form a moiety (A1) or (A2) as defined herein above, preferably a moiety (A2), and wherein the further groups and variables in formula (Ic), including in particular $R^5$, $R^6$, $R^7$, $R^9$ and m, have the same meanings, including the same preferred meanings, as described and defined herein above for the compound of formula (I).

Exemplary compounds of formula (Ic) are the following compounds 17, 20, 31, 32, 37 and 38 as well as pharmaceutically acceptable salts or solvates of any of these compounds:

17

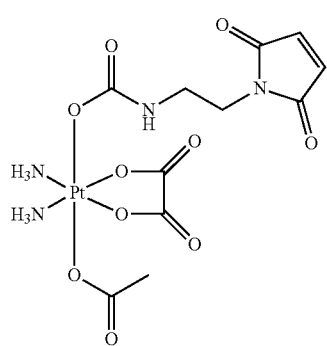

20

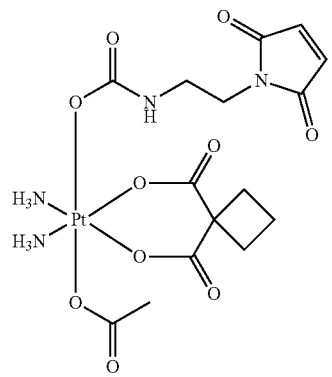

31

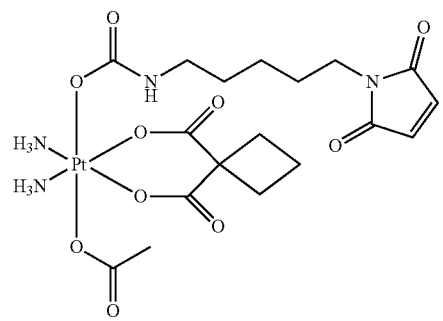

32

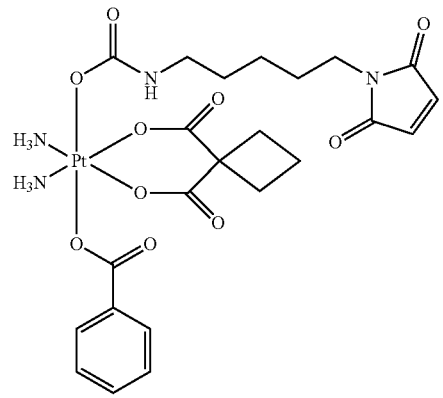

37

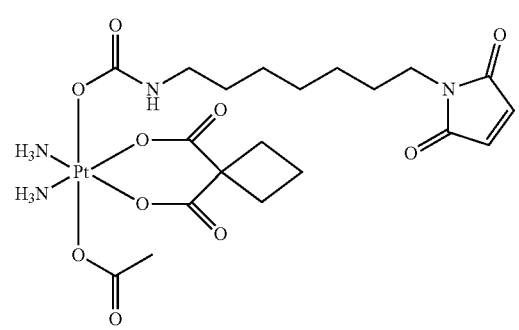

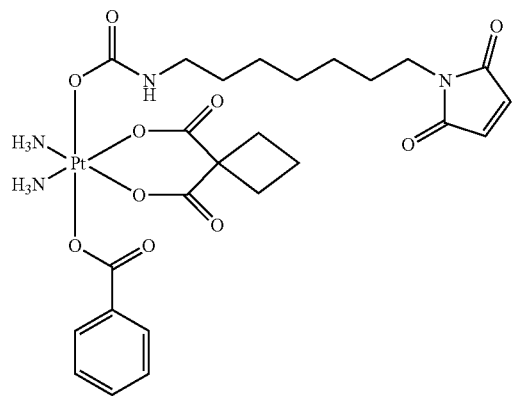

38

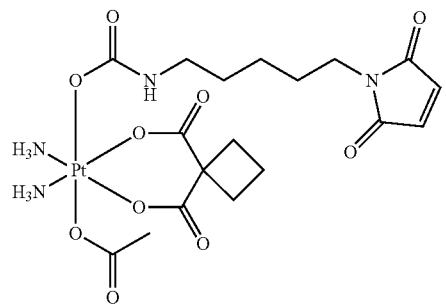

31

In a further preferred embodiment, the compound of formula (I) is a compound of the following formula (Id) or a pharmaceutically acceptable salt or solvate thereof:

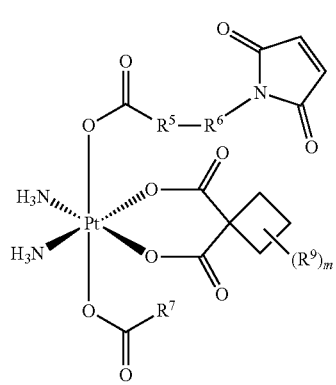

(Id)

wherein the groups and variables in formula (Id), including in particular $R^5$, $R^6$, $R^7$, $R^9$ and m, have the same meanings, including the same preferred meanings, as described and defined herein above for the compound of formula (I).

Particularly preferred compounds of formula (Id) are the following compounds 20 and 31 as well as pharmaceutically acceptable salts or solvates of any of these compounds:

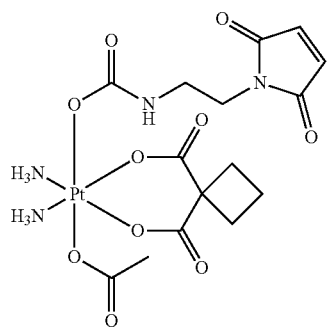

20

In a further embodiment, the compound of formula (I) is a compound of the following formula (Ie) or a pharmaceutically acceptable salt or solvate thereof:

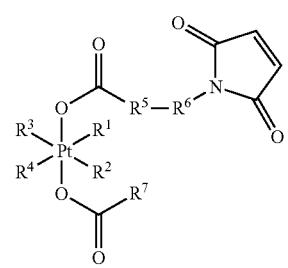

(Ie)

wherein $R^1$ and $R^2$ in formula (Ie) are joined together to form a moiety (A2) or (A3) as defined herein above, and wherein the further groups and variables in formula (Ie) have the same meanings, including the same preferred meanings, as described and defined herein above for the compound of formula (I).

In a further embodiment, the compound of formula (I) is a compound of the following formula (If) or a pharmaceutically acceptable salt or solvate thereof:

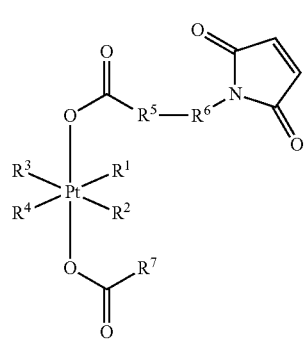

(If)

wherein $R^1$ and $R^2$ in formula (If) are joined together to form a moiety (A2) as defined herein above, and wherein the further groups and variables in formula (If) have the same meanings, including the same preferred meanings, as described and defined herein above for the compound of formula (I).

In a further embodiment, the compound of formula (I) is a compound of the following formula (Ig) or a pharmaceutically acceptable salt or solvate thereof:

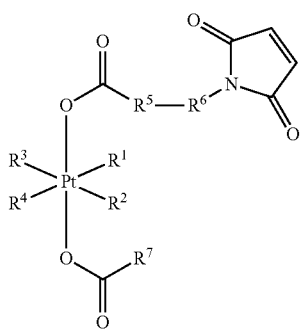

(Ig)

wherein $R^1$ and $R^2$ in formula (Ig) are joined together to form a moiety (A2) as defined herein above, wherein $R^3$ and $R^4$ are joined together to form a moiety (E1) as defined herein above, and wherein the further groups and variables in formula (Ig) have the same meanings, including the same preferred meanings, as described and defined herein above for the compound of formula (I).

In a further embodiment, the compound of formula (I) is a compound of the following formula (Ih) or a pharmaceutically acceptable salt or solvate thereof:

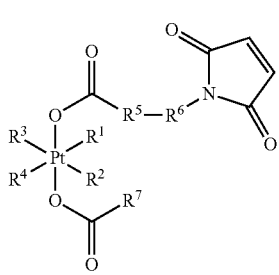

(Ih)

wherein $R^1$ and $R^2$ in formula (Ih) are joined together to form a moiety (A2) as defined herein above, wherein $R^3$ and $R^4$ are each —$NH_3$, and wherein the further groups and variables in formula (Ih) have the same meanings, including the same preferred meanings, as described and defined herein above for the compound of formula (I).

In a further embodiment, the compound of formula (I) is a compound of the following formula (Ii) or a pharmaceutically acceptable salt or solvate thereof:

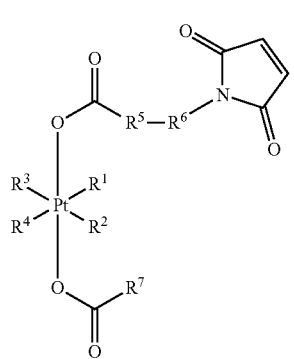

(Ii)

wherein $R^1$ and $R^2$ in formula (Ii) are joined together to form a moiety (A3) as defined herein above, and wherein the further groups and variables in formula (Ii) have the same meanings, including the same preferred meanings, as described and defined herein above for the compound of formula (I).

In a further embodiment, the compound of formula (I) is a compound of the following formula (Ij) or a pharmaceutically acceptable salt or solvate thereof:

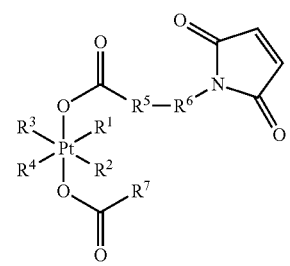

(Ij)

wherein $R^3$ in formula (Ij) is a moiety (B2) as defined herein above, wherein $R^4$ is —$NH_3$, and wherein the further groups and variables in formula (Ij) have the same meanings, including the same preferred meanings, as described and defined herein above for the compound of formula (I).

For a person skilled in the field of synthetic chemistry, various ways for the preparation of the compounds of formula (I) will be readily apparent. For example, the compounds of formula (I) can be prepared as described in the following and, in particular, they can be prepared in accordance with or in analogy to the synthetic routes described in Example 1.

Preparation of the Platinum(II) Precursors:

The platinum(II) precursors (P2) can be synthesized out of potassium tetrachloridoplatinate (P1) in aqueous solution, either using the corresponding amine ligands (E1) according to Kidani, Y; Inagaki, K. *J. Med. Chem.* 1978, 21(12), 1315-1318 or using ammonia ($R^3$ and $R^4$ are each: —$NH_3$) according to Dhara, S. Ch. *Indian J. Chem.* 1970, 8(2), 193-194. (P2) precursors, where $R^3$ is a (B2) moiety and $R^4$ is —$NH_3$ can be synthesized out of (P2), where $R^3$ and $R^4$ are each —$NH_3$, according to Giandomenico, C. M. et al. *Inorg. Chem.* 1995, 34, 1015-1021.

The platinum(II) precursors (P3) can be synthesized out of the precursors (P2) in aqueous solution using $AgNO_3$ or $Ag_2SO_4$ and the corresponding ligands $R^1$ and $R^2$, wherein $R^1$ and $R^2$ are joined together to form a moiety (A1), (A2) or (A3) (Kidani, Y; Inagaki, K. *J. Med. Chem.* 1978, 21(12), 1315-1318 or Rochon, F. D.; Gruia, L. M. *Inorg. Chim. Acta* 2000, 306, 193-204).

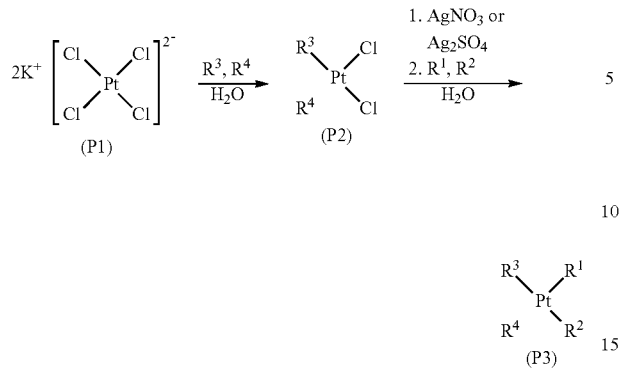

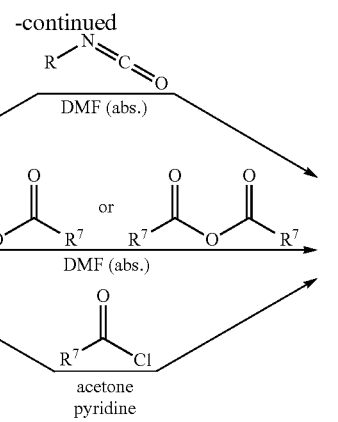

(P5)

Preparation of the Platinum(IV) Precursors:

The platinum(IV) precursors (P5) can be synthesized out of the platinum(II) precursors (P3) using the corresponding ligand $R^7COOH$ as the solvent and $H_2O_2$ according to Lee, Y.-A.; Jung, S. M.; Kang, S. W.; Jung, O.-S. *Transition Met. Chem.* 2004, 29, 710-713.

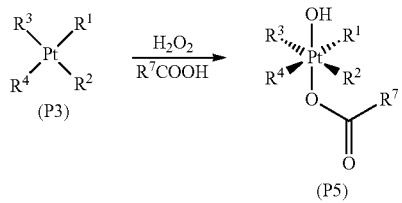

Alternatively, other organic solvents, like tetrahydrofuran or dichloromethane, as well as other oxidizing reagents, like tert-butyl hydroperoxide, can be used for preparation of (P5) (Zhang, J. Z. et al. *Chem. Eur. J.* 2013, 19, 1672-1676).

Another synthesis route for preparation of (P5) is a two-step procedure via the platinum precursors (P4). (P4) can be prepared by oxidation of (P3) with $H_2O_2$ in aqueous solution. In a second step, $R^7COOH$ as an isocyanate, symmetric or asymmetric anhydride, or acyl chloride can be attached to (P4) in an organic solvent like DMF or acetone (with or without pyridine) (in the scheme below, the use of an isocyanate reactant R—N=C=O results in the formation of a compound (P5), wherein —$R^7$ is —NH—R; the group R in the isocyanate reactant can thus be selected to provide a corresponding amino-containing group $R^7$ as defined in connection with the compound of formula (I)). Alternatively, any peptide-coupling reagent like DCC (N,N'dicyclohexylcarbodiimide) or TBTU (N,N,N',N'-tetramethyl-O-(benzotriazol-1-yl)uronium tetrafluoroborate) in an organic solvent can be used for coupling of RCOOH to (P4) (Zhang, J. Z. et al. *Chem. Eur. J.* 2013, 19, 1672-1676).

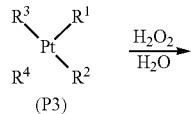

General Procedure for the Preparation of Isocyanates:

To a solution of the corresponding carboxylic acid in an organic solvent like acetone and 1.0-1.2 eq. of a base like triethylamine (at about −5° C.), an alkyl chloroformate like ethyl chloroformate (1.0-1.2 eq.) in an organic solvent like acetone is added. Subsequently, $NaN_3$ (1 eq.) is added and stirring is continued without cooling for 20-60 min. The reaction mixture is poured into water and extracted with toluene. The combined organic layers are dried over $MgSO_4$ and heated to reflux at 120-140° C. for 50-100 min. After removal of the solvent under reduced pressure, the crude product can be used without further purification.

General Procedure for the Preparation of Anhydrides:

Symmetric anhydrides can be prepared using triphosgene. Asymmetric anhydrides can be synthesized either using acetic anhydride (Höfer, D et al. *J. Inorg. Biochem.* in press, doi:10.1016/j.jinorgbio.2015.08.018), acyl chlorides (Kim, S. et al. *J Org. Chem.* 1985, 50, 560-565) or alkylchloroformates.

General Procedure for the Preparation of Acyl Chlorides:

Acyl chlorides can be prepared using for example oxalyl chloride and dimethylformamide as a catalyst (Mantovani, G. et al. *J. Am. Chem. Soc.* 2005, 127, 2966-2973).

Preparation of Compounds of Formula (I):

The compounds of formula (I) can be synthesized out of the platinum(IV) precursors (P5) using the maleimide-containing ligand as isocyanate, symmetric or asymmetric anhydride or acyl chloride in an organic solvent like DMF or acetone (with or without pyridine). Alternatively, any peptide-coupling reagent like DCC (N,N'dicyclohexylcarbodiimide) or TBTU (N,N,N',N'-tetramethyl-O-(benzotriazol-1-yl)uronium tetrafluoroborate) etc. in an organic solvent can be used for coupling of the maleimide-containing ligand to (P5) (Zhang, J. Z. et al. *Chem. Eur. J.* 2013, 19, 1672-1676).

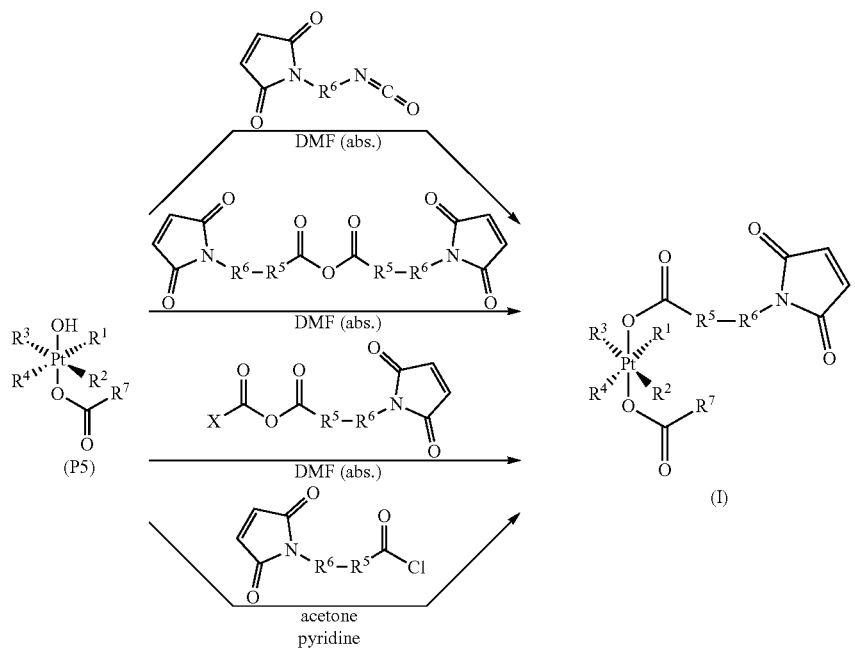

Alternatively, the maleimide-containing ligand as an isocyanate, symmetric or asymmetric anhydride or acyl chloride in an organic solvent like DMF or acetone (with or without pyridine) can be attached to precursor (P4) first to form (P6). Alternatively, any peptide-coupling reagent like DCC (N,N'-dicyclohexylcarbodiimide) or TBTU (N,N,N',N'-tetramethyl-O-(benzotriazol-1-yl)uronium tetrafluoroborate) in an organic solvent can be used for coupling of the maleimide-containing ligand to form (P6) (Zhang, J. Z. et al. *Chem. Eur. J.* 2013, 19, 1672-1676).

In a second step, $R^0COOH$ as isocyanate, symmetric or asymmetric anhydride or acyl chloride can be attached to (P6) in an organic solvent like DMF or acetone (with or without pyridine) to form the corresponding compound of formula (I). Alternatively, any peptide-coupling reagent like DCC (N,N'-dicyclohexylcarbodiimide) or TBTU (N,N,N',N'-tetramethyl-O-(benzotriazol-1-yl)uronium tetrafluoroborate) in an organic solvent can be used for coupling of RCOOH to (P6) to form the corresponding compound of formula (I) (Zhang, J. Z. et al. *Chem. Eur. J.* 2013, 19, 1672-1676).

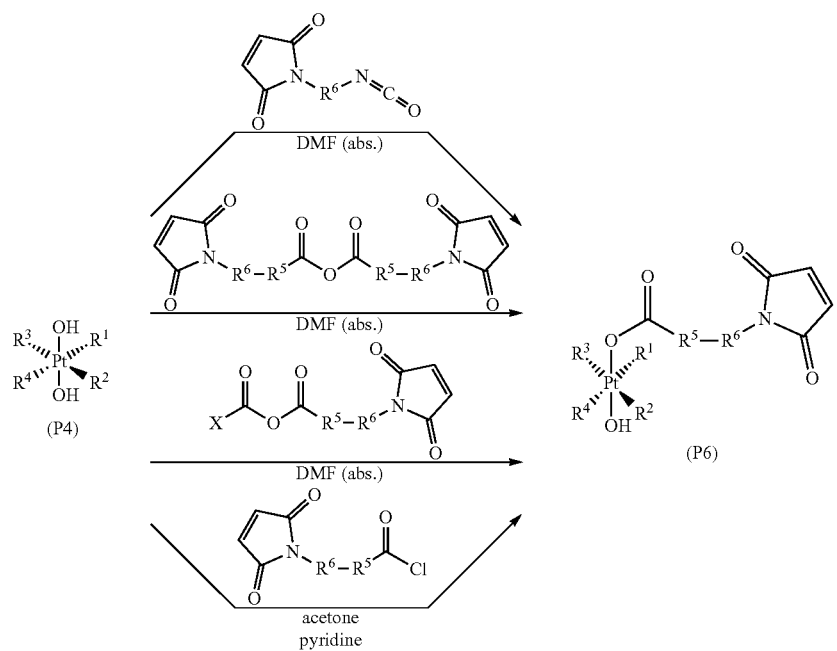

The following definitions apply throughout the present specification, unless specifically indicated otherwise.

As used herein, the term "hydrocarbon group" refers to a group consisting of carbon atoms and hydrogen atoms.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-8}$ alkyl" denotes an alkyl group having 1 to 8 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-8}$ alkenyl" denotes an alkenyl group having 2 to 8 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-8}$ alkynyl" denotes an alkynyl group having 2 to 8 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group, which may be linear or branched. A "$C_{1-8}$ alkylene" denotes an alkylene group having 1 to 8 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene (—$CH_2$—), ethylene (e.g., —$CH_2$—$CH_2$— or —CH(—$CH_3$)—), propylene (e.g., —$CH_2$—$CH_2$—$CH_2$—, —CH(—$CH_2$—$CH_3$)—, —$CH_2$—CH(—$CH_3$)—, or —CH(—$CH_3$)—$CH_2$—), or butylene (e.g., —$CH_2$—$CH_2$—$CH_2$—$CH_2$—). Unless defined otherwise, the term "alkylene" preferably refers to $C_{1-4}$ alkylene (including, in particular, linear $C_{1-4}$ alkylene), more preferably to methylene or ethylene.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "arylene" refers to an aryl group, as defined herein above, but having two points of attachment, i.e. a divalent aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Arylene" may, e.g., refer to phenylene (e.g., phen-1,2-diyl, phen-1,3-diyl, or phen-1,4-diyl), naphthylene (e.g., naphthalen-1,2-diyl, naphthalen-1,3-diyl, naphthalen-1,4-diyl, naphthalen-1,5-diyl, naphthalen-1,6-diyl, naphthalen-1,7-diyl, naphthalen-2,3-diyl, naphthalen-2,5-diyl, naphthalen-2,6-diyl, naphthalen-2,7-diyl, or naphthalen-2,8-diyl), 1,2-dihydronaphthylene, 1,2,3,4-tetrahydronaphthylene, indanylene, indenylene, anthracenylene, phenanthrenylene, 9H-fluorenylene, or azulenylene. Unless defined otherwise, an "arylene" preferably has 6 to 14 ring atoms, more preferably 6 to 10 ring atoms, even more preferably refers to phenylene or naphthylene, and most preferably refers to phenylene (particularly phen-1,4-diyl).

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three, or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 2H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3- triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5- to 14-membered (more preferably 5- to 10-membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5- or 6-membered monocyclic ring comprising one or more (e.g., one, two or three) ring heteroatoms independently selected from O, S, and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "heteroarylene" refers to a heteroaryl group, as defined herein above, but having two points of attachment, i.e. a divalent aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three, or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroarylene" may, e.g., refer to thienylene (i.e., thiophenylene; e.g., thien-2,3-diyl, thien-2,4-diyl, or thien-2,5-diyl), benzo[b]thienylene, naphtho[2,3-b]thienylene, thianthrenylene, furylene (i.e., furanylene; e.g., furan-2,3-diyl, furan-2,4-diyl, or furan-2,5-diyl), benzofuranylene, isobenzofuranylene, chromanylene, chromenylene, isochromenylene, chromonylene, xanthenylene, phenoxathiinylene, pyrrolylene, imidazolylene, pyrazolylene, pyridylene (i.e., pyridinylene), pyrazinylene, pyrimidinylene, pyridazinylene, indolylene, isoindolylene, indazolylene, indolizinylene, purinylene, quinolinylene, isoquinolinylene, phthalazinylene, naphthyridinylene, quinoxalinylene, cinnolinylene, pteridinylene, carbazolylene, β-carbolinylene, phenanthridinylene, acridinylene, perimidinylene, phenanthrolinylene, phenazinylene, thiazolylene (e.g., thiazol-2,4-diyl, thiazol-2,5-diyl, or thiazol-4,5-diyl), isothiazolylene (e.g., isothiazol-3,4-diyl, isothiazol-3,5-diyl, or isothiazol-4,5-diyl), phenothiazinylene, oxazolylene (e.g., oxazol-2,4-diyl, oxazol-2,5-diyl, or oxazol-4,5-diyl), isoxazolylene (e.g., isoxazol-3,4-diyl, isoxazol-3,5-diyl, or isoxazol-4,5-diyl), oxadiazolylene (e.g., 1,2,4-oxadiazol-3,5-diyl, 1,2,5-oxadiazol-3,4-diyl, or 1,3,4-oxadiazol-2,5-diyl), thiadiazolylene (e.g., 1,2,4-thiadiazol-3,5-diyl, 1,2,5-thiadiazol-3,4-diyl, or 1,3,4-thiadiazol-2,5-diyl), phenoxazinylene, pyrazolo[1,5-a]pyrimidinylene, 1,2-benzoisoxazolylene, benzothiazolylene, benzothiadiazolylene, benzoxazolylene, benzisoxazolylene, benzimidazolylene, benzo[b]thiophenylene (i.e., benzothienylene), triazolylene (e.g., 1H-1,2,3-triazolylene, 2H-1,2,3-triazolylene, 1H-1,2,4-triazolylene, or 4H-1,2,4-triazolylene), benzotriazolylene, 1H-tetrazolylene, 2H-tetrazolylene, triazinylene (e.g., 1,2,3-triazinylene, 1,2,4-triazinylene, or 1,3,5-triazinylene), furo[2,3-c]pyridinylene, dihydrofuropyridinylene (e.g., 2,3-dihydrofuro[2,3-c]pyridinylene or 1,3-dihydrofuro[3,4-c]pyridinylene), imidazopyridinylene (e.g., imidazo[1,2-a]pyridinylene or imidazo[3,2-a]pyridinylene), quinazolinylene, thienopyridinylene, tetrahydrothienopyridinylene (e.g., 4,5,6,7-tetrahydrothieno[3,2-c]pyridinylene), dibenzofuranylene, 1,3-benzodioxolylene, benzodioxanylene (e.g., 1,3-benzodioxanylene or 1,4-benzodioxanylene), or coumarinylene. Unless defined otherwise, the term "heteroarylene" preferably refers to a divalent 5- to 14-membered (more preferably 5- to 10-membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroarylene" refers to a divalent 5- or 6-membered monocyclic ring comprising one or more (e.g., one, two or three) ring heteroatoms independently selected from O, S, and N, wherein one or more S ring atoms (if present) and/or one or more N ring atoms (if present) are optionally oxidized, and wherein one or more carbon ring atoms are optionally oxidized. A "heteroarylene", including any of the specific heteroarylene groups described herein, may be attached through two carbon ring atoms, particularly through those two carbon ring atoms that have the greatest distance from one another (in terms of the number of ring atoms separating them by the shortest possible connection) within one single ring or within the entire ring system of the corresponding heteroarylene. Moreover, unless defined otherwise, the term "heteroarylene" particularly preferably refers to pyridinylene, imidazolylene, thiazolylene, 1H-tetrazolylene, 2H-tetrazolylene, thienylene (i.e., thiophenylene), or pyrimidinylene.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3- to 11-membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5- to 7-membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —CF$_3$, —CHF$_2$, —CH$_2$F, —CF$_2$—CH$_3$, —CH$_2$—CF$_3$, —CH$_2$—CHF$_2$, —CH$_2$—CF$_2$—CH$_3$, —CH$_2$—CF$_2$—CF$_3$, or —CH(CF$_3$)$_2$. A particularly preferred "haloalkyl" group is —CF$_3$.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, unless explicitly indicated otherwise or contradicted by context, the terms "a", "an" and "the" are used interchangeably with "one or more" and "at least one". Thus, for example, a composition comprising "a" compound of formula (I) can be interpreted as referring to a composition comprising "one or more" compounds of formula (I).

As used herein, the term "about" preferably refers to ±10% of the indicated numerical value, more preferably to ±5% of the indicated numerical value, and in particular to the exact numerical value indicated.

As used herein, the term "comprising" (or "comprise", "comprises", "contain", "contains", or "containing"), unless explicitly indicated otherwise or contradicted by context, has the meaning of "containing, interalia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

The scope of the invention embraces all pharmaceutically acceptable salt forms of the compounds of formula (I) which may be formed, e.g., by protonation of an atom carrying an electron lone pair, which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. If the compound of formula (I) is in the form of a pharmaceutically acceptable salt, it is preferably in the form of a hydrochloride salt. Most preferably, however, the compound of formula (I), including any one of the specific compounds of formula (I) described herein (such as KP2299), is not in the form of a salt.

Moreover, the scope of the invention embraces the compounds of formula (I) in any solvated form, including, e.g., solvates with water (i.e., as a hydrate) or solvates with organic solvents such as, e.g., methanol, ethanol or acetonitrile (i.e., as a methanolate, ethanolate or acetonitrilate), or in any crystalline form (i.e., as any polymorph), or in amorphous form. It is to be understood that such solvates of the compounds of the formula (I) also include solvates of pharmaceutically acceptable salts of the compounds of the formula (I).

Furthermore, the compounds of formula (I) may exist in the form of different isomers, in particular stereoisomers (including, e.g., geometric isomers (or cis/trans isomers), enantiomers and diastereomers) or tautomers. All such isomers of the compounds of formula (I) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. In particular, if one or both of the ligand pairs $R^1/R^2$ and $R^3/R^4$ is/are asymmetric, e.g., due to their substitution pattern or the presence of moiety (A3) and/or moiety (B2), the platinum(IV) atom in the corresponding compound of formula (I) will form a stereocenter, resulting in stereoisomers that differ with respect to the orientation of the two axial ligands (i.e., the axial ligand containing $R^5$ and $R^6$, and the axial ligand containing $R^7$), such as, e.g., the stereoisomers 18 and 19 as depicted herein above; any such stereoisomers of the compounds of formula (I) are likewise encompassed by the present invention. The present invention further encompasses any tautomers of the compounds provided herein.

The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2$H; also referred to as "D"). Accordingly, the invention also embraces compounds of formula (I) which are enriched in deuterium. Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water (D20). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^1$H hydrogen atoms in the compounds of formula (I) is preferred.

The present invention also embraces compounds of formula (I), in which one or more atoms are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers or imaging probes in positron emission tomography (PET). The invention thus includes (i) compounds of formula (I), in which one or more fluorine atoms (or, e.g., all fluorine atoms) are replaced by $^{18}$F atoms, (ii) compounds of formula (I), in which one or more carbon atoms (or, e.g., all carbon atoms) are replaced by $^{11}$C atoms, (iii) compounds of formula (I), in which one or more nitrogen atoms (or, e.g., all nitrogen atoms) are replaced by $^{13}$N atoms, (iv) compounds of formula (I), in which one or more oxygen atoms (or, e.g., all oxygen atoms) are replaced by 150 atoms, (v) compounds of formula (I), in which one or more bromine atoms (or, e.g., all bromine atoms) are replaced by $^{76}$Br atoms, (vi) compounds of formula (I), in which one or more bromine atoms (or, e.g., all bromine atoms) are replaced by $^{77}$Br atoms, (vii) compounds of formula (I), in which one or more iodine atoms (or, e.g., all iodine atoms) are replaced by $^{120}$I atoms, and (viii) compounds of formula (I), in which one or more iodine atoms (or, e.g., all iodine atoms) are replaced by $^{124}$I atoms. In general, it is preferred that none of the atoms in the compounds of formula (I) are replaced by specific isotopes.

The compounds provided herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions may comprise one or more solubility enhancers, such as, e.g., poly(ethylene glycol), including poly(ethylene glycol) having a molecular weight in the range of about 200 to about 5,000 Da (e.g., PEG 200, PEG 300, PEG 400, or PEG 600), ethylene glycol, propylene glycol, glycerol, a non-ionic surfactant, tyloxapol, polysorbate 80, macrogol-15-hydroxystearate (e.g., Kolliphor® HS 15, CAS 70142-34-6), a phospholipid, lecithin, dimyristoyl phosphatidylcholine, dipalmitoyl phosphatidylcholine, distearoyl phosphatidylcholine, a cyclodextrin, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, a carboxyalkyl thioether, hydroxypropyl methylcellulose, hydroxypropylcellulose, polyvinylpyrrolidone, a vinyl acetate copolymer, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in "Remington: The Science and Practice of Pharmacy", Pharmaceutical Press, $22^{nd}$ edition. The pharmaceutical compositions can be formulated as dosage forms for oral, parenteral, such as intramuscular, intravenous, subcutaneous, intradermal, intraarterial, or intraperitoneal (especially in form of hyperthermic chemoperfusion) administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders, and granules for reconstitution. Emulsions are a preferred dosage form for parenteral administration.

The compounds of formula (I) or the above described pharmaceutical compositions comprising a compound of formula (I) may be administered to a subject by any convenient route of administration, whether systemically/peripherally or at the site of desired action, including but not limited to one or more of: oral (e.g., as a tablet, capsule, or as an ingestible solution), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, or ophthalmic (including intravitreal or intracameral) administration.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution, which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773, 919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds of formula (I) for pulmonary administration, particularly inhalation. Such dry powders may be prepared by spray drying under conditions, which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the invention can be carried out, e.g., as described generally in the "Spray Drying Handbook", 5th ed., K. Masters, John Wiley & Sons, Inc., NY (1991), in WO 97/41833, or in WO 03/053411.

The present invention thus relates to the compounds or the pharmaceutical compositions provided herein, wherein the corresponding compound or pharmaceutical composition is to be administered by any one of: an oral route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; or ophthalmic route, including by intravitreal, or intracameral route. Particularly preferred routes of administration are parenteral administrations like, e.g., intravenous and intraperitoneal (during hyperthermic chemoperfusion).

Typically, a physician will determine the actual dosage, which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for intravenous administration to a human (of approximately 70 kg body weight) may be 10 to 1000 mg, preferably 250 to 350 mg, of the active ingredient (such as KP2299) per unit dose. The unit dose may be administered, e.g., once every two weeks. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compound of formula (I) or a pharmaceutical composition comprising the compound of formula (I) can be administered in monotherapy (e.g., without concomitant administration of any further therapeutic agents or, in particular, without concomitant administration of any further anticancer drugs). However, the compound of formula (I) or a pharmaceutical composition comprising the compound of formula (I) can also be administered in combination with one or more further therapeutic agents. If the compound of formula (I) is used in combination with a second therapeutic agent active against the same disease or condition (e.g., a further anticancer drug), the dose of each compound may differ from that when the corresponding compound is used alone, in particular, a lower dose of each compound may be used. The combination of the compound of formula (I) with one or more further therapeutic agents may comprise the simultaneous/concomitant administration of the compound of formula (I) and the further therapeutic agent(s) (either in a single pharmaceutical formulation or in separate pharmaceutical formulations), or the sequential/separate administration of the compound of formula (I) and the further therapeutic agent(s). If administration is sequential, either the compound of formula (I) according to the invention or the one or more further therapeutic agents may be administered first. If administration is simultaneous, the one or more further therapeutic agents may be included in the same pharmaceutical formulation as the compound of formula (I), or they may be administered in one or more different (separate) pharmaceutical formulations.

Preferably, the one or more further therapeutic agents to be administered in combination with a compound of the present invention are anticancer drugs. The anticancer drug (s) to be administered in combination with a compound of formula (I) according to the invention may, e.g., be selected from: an angiogenesis inhibitor (e.g., a protease inhibitor, a fibroblast growth factor receptor kinase inhibitor, or a vascular endothelial growth factor receptor kinase inhibitor); a cytostatic drug (e.g., an antimetabolite, such as purine and pyrimidine analog antimetabolites); an antimitotic agent (e.g., a microtubule-stabilizing drug or an antimitotic alkaloid); a platinum coordination complex; an anti-tumor antibiotic; an alkylating agent (e.g., a nitrogen mustard or a nitrosourea); an endocrine agent (e.g., an adrenocorticosteroid, an androgen, an anti-androgen, an estrogen, an anti-estrogen, an aromatase inhibitor, a gonadotropin-releasing hormone agonist, or a somatostatin analog); or a compound that targets an enzyme or receptor that is overexpressed and/or otherwise involved in a specific metabolic pathway that is misregulated/deregulated in the tumor cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors, PI3K inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/ antagonists. In addition, this also includes combination with an immunooncology therapeutic agent e.g. targeting CTLA-4, PD-1/PD-L1 but also other immune-stimulatory strategies.

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex, which can be used as an anticancer drug in combination with a compound of the present invention may be, for example, cisplatin, carboplatin, nedaplatin, oxaliplatin, satraplatin, or triplatin tetranitrate.

A cytotoxic drug, which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent, which can be used as an anticancer drug in combination with a compound of the present invention may be, for example, a taxane (such as docetaxel, larotaxel, ortataxel, paclitaxel/taxol, tesetaxel, or nab-paclitaxel (e.g., Abraxane®)), a *Vinca* alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic, which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor, which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, axitinib, nintedanib, ponatinib, or vandetanib.

A topoisomerase inhibitor, which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

A PARP inhibitor, which can be used as an anticancer drug in combination with a compound of the present invention may be, for example, BMN-673, olaparib, rucaparib, veliparib, CEP 9722, MK 4827, BGB-290, or 3-aminobenzamide.

An EGFR inhibitor/antagonist, which can be used as an anticancer drug in combination with a compound of the present invention may be, for example, gefitinib, erlotinib, lapatinib, afatinib, osimertinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, or matuzumab.

Further anticancer drugs may also be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, or iniparib.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP1071752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in co-therapy approaches with the compounds of the invention can be found, e.g., in: Taylor P C. Curr Opin Pharmacol. 2003. 3(3):323-328; or Roxana A. Maedica. 2006. 1(1):63-65.

An anticancer drug, which can be used in combination with a compound of the present invention may, in particular, be an immunooncology therapeutic (such as an antibody (e.g., a monoclonal antibody or a polyclonal antibody), an antibody fragment, an antibody construct (e.g., a single-chain construct), or a modified antibody (e.g., a CDR-grafted antibody, a humanized antibody, or a "full humanized" antibody) targeting any one of CTLA-4, PD-1/PD-L1, TIM3, LAG3, OX4, CSF1R, IDO, or CD40. Such immunooncology therapeutics include, e.g., an anti-CTLA-4 antibody (particularly an antagonistic or pathway-blocking anti-CTLA-4 antibody; e.g., ipilimumab or tremelimumab), an anti-PD-1 antibody (particularly an antagonistic or pathway-blocking anti-PD-1 antibody; e.g., nivolumab (BMS-936558), pembrolizumab (MK-3475), pidilizumab (CT-011), AMP-224, or APE02058), an anti-PD-L1 antibody (particularly a pathway-blocking anti-PD-L1 antibody; e.g., BMS-936559, MED14736, MPDL3280A (RG7446), MDX-1105, or MED16469), an anti-TIM3 antibody (particularly a pathway-blocking anti-TIM3 antibody), an anti-LAG3 antibody (particularly an antagonistic or pathway-blocking anti-LAG3 antibody; e.g., BMS-986016, IMP701, or IMP731), an anti-OX4 antibody (particularly an agonistic anti-OX4 antibody; e.g., MED10562), an anti-CSF1R antibody (particularly a pathway-blocking anti-CSF1R antibody; e.g., IMC-CS4 or RG7155), an anti-IDO antibody (particularly a pathway-blocking anti-IDO antibody), or an anti-CD40 antibody (particularly an agonistic anti-CD40 antibody; e.g., CP-870,893 or Chi Lob 7/4). Further immunooncology therapeutics are known in the art and are described, e.g., in: Kyi C et al., FEBS Lett, 2014, 588(2):368-76; Intlekofer A M et al., J Leukoc Biol, 2013, 94(1):25-39; Callahan M K et al., J Leukoc Biol, 2013, 94(1):41-53; Ngiow S F et al., Cancer Res, 2011, 71(21):6567-71; and Blattman J N et al., Science, 2004, 305(5681):200-5.

It is particularly preferred that the compounds of formula (I), such as KP2299, are to be administered in combination with folinic acid (e.g., leucovorin calcium or leucovorin sodium) and 5-fluorouracil.

A further example of a combination therapy may comprise the administration of a compound of formula (I), including in particular one wherein $R^1$ and $R^2$ are joined together to form a moiety (A2) and wherein $R^3$ and $R^4$ are each —$NH_3$ (such as, e.g., compound 20), in combination with a taxane (such as, e.g., paclitaxel/taxol, nab-paclitaxel (e.g., Abraxane®), docetaxel, larotaxel, ortataxel, or tesetaxel; preferably paclitaxel or nab-paclitaxel; more preferably paclitaxel) and an anti-PD-1 antibody (particularly an antagonistic anti-PD-1 antibody; such as, e.g., nivolumab, pembrolizumab, pidilizumab, AMP-224, or APE02058; preferably nivolumab). It is preferred that said compound of formula (I) is to be administered in combination with paclitaxel and nivolumab.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e., the compound of formula (I) or a pharmaceutically acceptable salt or solvate thereof) or the further therapeutic agent(s) may be administered first.

When administration is simultaneous, the combination may be administered either in the same pharmaceutical composition or in different pharmaceutical compositions. When combined in the same formulation, it will be appreciated that the two or more compounds must be stable and compatible with each other and the other components of the formulation. When formulated separately, they may be provided in any convenient formulation.

The compounds of formula (I) can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formula (I) or a pharmaceutically acceptable salt or solvate thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with one or more anticancer drugs and/or in combination with radiotherapy and/or immunotherapy.

Yet, the compounds of formula (I) can also be used in monotherapy, particularly in the monotherapeutic treatment or prevention of cancer (i.e., without administering any other anticancer agents until the treatment with the compound(s) of formula (I) is terminated). Accordingly, the invention also relates to a compound of formula (I) or a pharmaceutically acceptable salt or solvate thereof, or a pharmaceutical composition comprising any of the aforementioned entities in combination with a pharmaceutically acceptable excipient, for use in the monotherapeutic treatment or prevention of cancer.

The subject or patient to be treated in accordance with the present invention may be an animal (e.g., a non-human animal), a vertebrate animal, a mammal, a rodent (e.g., a guinea pig, a hamster, a rat, or a mouse), a canine (e.g., a dog), a feline (e.g., a cat), a porcine (e.g., a pig), an equine (e.g., a horse), a primate or a simian (e.g., a monkey or an ape, such as a marmoset, a baboon, a gorilla, a chimpanzee, an orangutan, or a gibbon), or a human. In accordance with the present invention, it is envisaged that animals are to be treated which are economically, agronomically or scientifically important. Scientifically important organisms include, but are not limited to, mice, rats, and rabbits. Lower organisms such as, e.g., fruit flies like *Drosophila* melagonaster and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, a cattle, or a pig). Most preferably, the subject/patient is a human. The subject/patient to be treated in accordance with the invention may be female or male. In a particular aspect, the present invention relates to the treatment of a female subject/patient, preferably a female animal (e.g., a female of any one of the species mentioned in this paragraph), more preferably a female human or a female non-human mammal, and even more preferably a female human.

The term "treatment" of a disorder or disease as used herein (e.g., "treatment" of cancer) is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease as used herein (e.g., "prevention" of cancer) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

The present invention particularly relates to the following items:

1. A compound of the following formula (I)

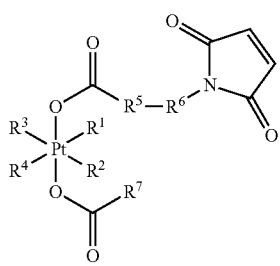
(I)

wherein:

$R^1$ and $R^2$ are joined together to form a moiety (A1), (A2) or (A3):

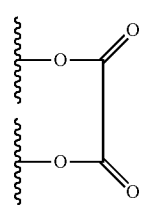
(A1)

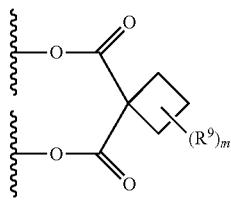
(A2)

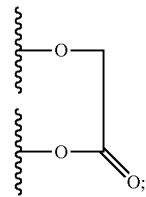
(A3)

$R^3$ and $R^4$ are joined together to form a moiety (1), or $R^3$ is a moiety (B2) and $R^4$ is —$NH_3$, or $R^3$ and $R^4$ are each —$NH_3$:

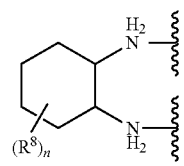
(B1)

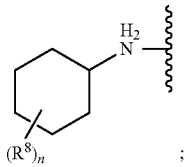
(B2)

$R^5$ is —$N(R^{51})$— or —$CH_2$—;
$R^{51}$ is hydrogen or $C_{1-8}$ alkyl;
$R^6$ is $C_{1-8}$ alkylene, wherein one or two —$CH_2$— units comprised in said $C_{1-8}$ alkylene are each optionally replaced by a group independently selected from —O—, —CO—, —C(=O)O—, —O—C(=O)—, —N($R^{61}$)—, —N($R^{61}$)—CO—, —CO—N($R^{61}$)—, arylene, and heteroarylene, wherein said arylene and said heteroarylene are each optionally substituted with one or more groups $R^{62}$;
each $R^{61}$ is independently selected from hydrogen and $C_{1-8}$ alkyl;
each $R^{62}$ is independently selected from $C_{1-8}$ alkyl, $C_{2-8}$ alkenyl, $C_{2-8}$ alkynyl, —($C_{0-3}$ alkylene)-OH, —($C_{0-3}$ alkylene)-O($C_{1-8}$ alkyl), —($C_{0-3}$ alkylene)-SH, —($C_{0-3}$ alkylene)-S($C_{1-8}$ alkyl), —($C_{0-3}$ alkylene)-$NH_2$, —($C_{0-3}$ alkylene)-NH($C_{1-8}$ alkyl), —($C_{0-3}$ alkylene)-N($C_{1-8}$ alkyl)($C_{1-8}$ alkyl), —($C_{0-3}$ alkylene)-halogen, —($C_{0-3}$ alkylene)-($C_{1-8}$ haloalkyl), —($C_{0-3}$ alkylene)-$CF_3$, —($C_{0-3}$ alkylene)-CN, —($C_{0-3}$ alkylene)-CHO, —($C_{0-3}$ alkylene)-CO—($C_{1-8}$ alkyl), —($C_{0-3}$ alkylene)-COOH, —($C_{0-3}$ alkylene)-CO—O—($C_{1-8}$ alkyl), —($C_{0-3}$ alkylene)-O—CO—($C_{1-8}$ alkyl), —($C_{0-3}$ alkylene)-CO—$NH_2$, —($C_{0-3}$ alkylene)-CO—NH($C_{1-8}$ alkyl), —($C_{0-3}$ alkylene)-CO—N($C_{1-8}$ alkyl)($C_{1-8}$ alkyl), —($C_{0-3}$ alkylene)-NH—CO—($C_{1-8}$ alkyl), —($C_{0-3}$ alkylene)-N($C_{1-8}$ alkyl)-CO—($C_{1-8}$ alkyl), —($C_{0-3}$ alkylene)-SO$_2$—NH$_2$, —($C_{0-3}$ alkylene)-SO$_2$—NH($C_{1-8}$ alkyl), —($C_{0-3}$ alkylene)-SO$_2$—N($C_{1-8}$ alkyl)($C_{1-8}$ alkyl), —($C_{0-3}$ alkylene)-NH—SO$_2$—($C_{1-8}$ alkyl), and —($C_{0-3}$ alkylene)-N($C_{1-8}$ alkyl)-SO$_2$—($C_{1-8}$ alkyl);

$R^7$ is selected from hydrogen, $C_{1-8}$ alkyl, $C_{2-8}$ alkenyl, $C_{2-8}$ alkynyl, cycloalkyl, heterocycloalkyl, aryl, heteroaryl, —O—($C_{1-8}$ alkyl), —O—($C_{2-8}$ alkenyl), —O—($C_{2-8}$ alkynyl), —O-cycloalkyl, —O-heterocycloalkyl, —O-aryl, —O-heteroaryl, —N($R^{71}$)—($C_{1-8}$ alkyl), —N($R^{71}$)—($C_{2-8}$ alkenyl), —N($R^{71}$)—($C_{2-8}$ alkynyl), —N($R^{71}$)-cycloalkyl, —N($R^{71}$)-heterocycloalkyl, —N($R^{71}$)-aryl, and —N($R^{71}$)-heteroaryl, wherein said $C_{1-8}$ alkyl or the $C_{1-8}$ alkyl moiety comprised in any of the aforementioned groups, said $C_{2-8}$ alkenyl or the $C_{2-8}$ alkenyl moiety comprised in any of the aforementioned groups, and said $C_{2-8}$ alkynyl or the $C_{2-8}$ alkynyl moiety comprised in any of the aforementioned groups are each optionally substituted with one or more groups $R^{72}$, and further wherein said cycloalkyl or the cycloalkyl moiety comprised in any of the aforementioned groups, said heterocycloalkyl or the heterocycloalkyl moiety comprised in any of the aforementioned groups, said aryl or the aryl moiety comprised in any of the aforementioned groups, and said heteroaryl or the heteroaryl moiety comprised in any of the aforementioned groups are each optionally substituted with one or more groups $R^{73}$;

each $R^{71}$ is independently selected from hydrogen and $C_{1-8}$ alkyl;

each $R^{72}$ is independently selected from —OH, —O($C_{1-8}$ alkyl), —SH, —S($C_{1-8}$ alkyl), —NH$_2$, —NH($C_{1-8}$ alkyl), —N($C_{1-8}$ alkyl)($C_{1-8}$ alkyl), halogen, $C_{1-8}$ haloalkyl, —CF$_3$, —CN, —CHO, —CO—($C_{1-8}$ alkyl), —COOH, —CO—O—($C_{1-8}$ alkyl), —O—CO—($C_{1-8}$ alkyl), —CO—NH$_2$, —CO—NH($C_{1-8}$ alkyl), —CO—N($C_{1-8}$ alkyl)($C_{1-8}$ alkyl), —NH—CO—($C_{1-8}$ alkyl), —N($C_{1-8}$ alkyl)-CO—($C_{1-8}$ alkyl), —SO$_2$—NH$_2$, —SO$_2$—NH($C_{1-8}$ alkyl), —SO$_2$—N($C_{1-8}$ alkyl)($C_{1-8}$ alkyl), —NH—SO$_2$—($C_{1-8}$ alkyl), and —N($C_{1-8}$ alkyl)-SO$_2$—($C_{1-8}$alkyl);

each $R^{73}$ is independently selected from $C_{1-8}$ alkyl, $C_{2-8}$ alkenyl, $C_{2-8}$ alkynyl, —($C_{0-3}$ alkylene)-OH, —($C_{0-3}$ alkylene)-O($C_{1-8}$ alkyl), —($C_{0-3}$ alkylene)-SH, —($C_{0-3}$ alkylene)-S($C_{1-8}$ alkyl), —($C_{0-3}$ alkylene)-NH$_2$, —($C_{0-3}$ alkylene)-NH($C_{1-8}$ alkyl), —($C_{0-3}$ alkylene)-N($C_{1-8}$ alkyl)($C_{1-8}$ alkyl), —($C_{0-3}$ alkylene)-halogen, —($C_{0-3}$ alkylene)-($C_{1-8}$ haloalkyl), —($C_{0-3}$ alkylene)-CF$_3$, —($C_{0-3}$ alkylene)-CN, —($C_{0-3}$ alkylene)-CHO, —($C_{0-3}$ alkylene)-CO—($C_{1-8}$ alkyl), —($C_{0-3}$ alkylene)-COOH, —($C_{0-3}$ alkylene)-CO—O—($C_{1-8}$ alkyl), —($C_{0-3}$ alkylene)-O—CO—($C_{1-8}$ alkyl), —($C_{0-3}$ alkylene)-CO—NH$_2$, —($C_{0-3}$ alkylene)-CO—NH($C_{1-8}$ alkyl), —($C_{0-3}$ alkylene)-CO—N($C_{1-8}$ alkyl)($C_{1-8}$ alkyl), —($C_{0-3}$ alkylene)-NH—CO—($C_{1-8}$ alkyl), —($C_{0-3}$ alkylene)-N($C_{1-8}$ alkyl)-CO—($C_{1-8}$ alkyl), —($C_{0-3}$ alkylene)-SO$_2$—NH$_2$, —($C_{0-3}$ alkylene)-SO$_2$—NH($C_{1-8}$ alkyl), —($C_{0-3}$ alkylene)-SO$_2$—N($C_{1-8}$ alkyl)($C_{1-8}$ alkyl), —($C_{0-3}$ alkylene)-NH—SO$_2$—($C_{1-8}$ alkyl), and —($C_{0-3}$ alkylene)-N($C_{1-8}$ alkyl)-SO$_2$—($C_{1-8}$ alkyl);

each $R^8$ is independently selected from $C_{1-8}$ alkyl, $C_{2-8}$ alkenyl, $C_{2-8}$ alkynyl, —OH, —O—($C_{1-8}$ alkyl), —SH, —S—($C_{1-8}$ alkyl), —NH$_2$, —NH($C_{1-8}$ alkyl), —N($C_{1-8}$ alkyl)($C_{1-8}$ alkyl), halogen, $C_{1-8}$ haloalkyl, —CF$_3$, —CN, —CHO, —CO—($C_{1-8}$ alkyl), —COOH, —CO—O—($C_{1-8}$ alkyl), —O—CO—($C_{1-8}$ alkyl), —CO—NH$_2$, —CO—NH($C_{1-8}$ alkyl), —CO—N($C_{1-8}$ alkyl)($C_{1-8}$ alkyl), —NH—CO—($C_{1-8}$ alkyl), —N($C_{1-8}$ alkyl)-CO—($C_{1-8}$ alkyl), —SO$_2$—NH$_2$, —SO$_2$—NH($C_{0-8}$ alkyl), —SO$_2$—N($C_{1-8}$ alkyl)($C_{1-8}$ alkyl), —NH—SO$_2$—($C_{1-8}$ alkyl), and —N($C_{1-8}$ alkyl)-SO$_2$—($C_{1-8}$alkyl);

each $R^9$ is independently selected from $C_{1-8}$ alkyl, $C_{2-8}$ alkenyl, $C_{2-8}$ alkynyl, —OH, —O—($C_{1-8}$ alkyl), —SH, —S—($C_{1-8}$ alkyl), —NH$_2$, —NH($C_{1-8}$ alkyl), —N($C_{1-8}$ alkyl)($C_{1-8}$ alkyl), halogen, $C_{1-8}$ haloalkyl, —CF$_3$, —CN, —CHO, —CO—($C_{1-8}$ alkyl), —COOH, —CO—O—($C_{1-8}$ alkyl), —O—CO—($C_{1-8}$ alkyl), —CO—NH$_2$, —CO—NH($C_{1-8}$ alkyl), —CO—N($C_{1-8}$ alkyl)($C_{1-8}$ alkyl), —NH—CO—($C_{1-8}$ alkyl), —N($C_{1-8}$ alkyl)-CO—($C_{1-8}$ alkyl), —SO$_2$—NH$_2$, —SO$_2$—NH($C_{1-8}$ alkyl), —SO$_2$—N($C_{1-8}$ alkyl)($C_{1-8}$ alkyl), —NH—SO$_2$—($C_{1-8}$ alkyl), and —N($C_{1-8}$ alkyl)-SO$_2$—($C_{1-8}$alkyl);

n is an integer of 0 to 8; and m is an integer of 0 to 6;

or a pharmaceutically acceptable salt or solvate thereof.

2. The compound of item 1, wherein $R^1$ and $R^2$ are joined together to form a moiety (A1).

3. The compound of item 1 or 2, wherein $R^3$ and $R^4$ are joined together to form a moiety (E1).

4. The compound of any one of items 1 to 3, wherein $R^5$ is —NH—, —N(—CH$_3$)— or —N(—CH$_2$CH$_3$)—

5. The compound of any one of items 1 to 4, wherein $R^6$ is $C_{1-8}$ alkylene.

6. The compound of any one of items 1 to 5, wherein $R^6$ is selected from —CH$_2$—, —(CH$_2$)$_2$—, —(CH$_2$)$_3$—, —(CH$_2$)$_4$—, and —(CH$_2$)$_5$—.

7. The compound of any one of items 1 to 6, wherein $R^7$ is selected from $C_{1-8}$ alkyl, $C_{2-8}$ alkenyl, and $C_{2-8}$ alkynyl.

8. The compound of any one of items 1 to 7, wherein $R^7$ is $C_{1-5}$ alkyl.

9. The compound of any one of items 1 to 8, wherein n and m are each 0.

10. The compound of any one of items 1 to 9, wherein $R^1$ and $R^2$ are joined together to form a moiety (A1), and wherein $R^3$ and $R^4$ are joined together to form a moiety (E1).

11. The compound of item 1 or any one of its dependent items 3 to 9, wherein $R^1$ and $R^2$ are joined together to form a moiety (A2), and wherein $R^3$ and $R^4$ are each —NH$_3$.

12. The compound of item 1, which is a compound having any one of the following formulae:

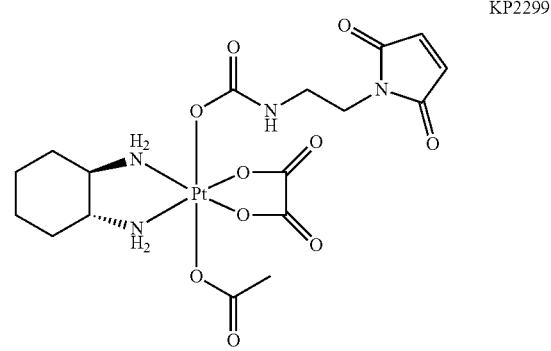

KP2299

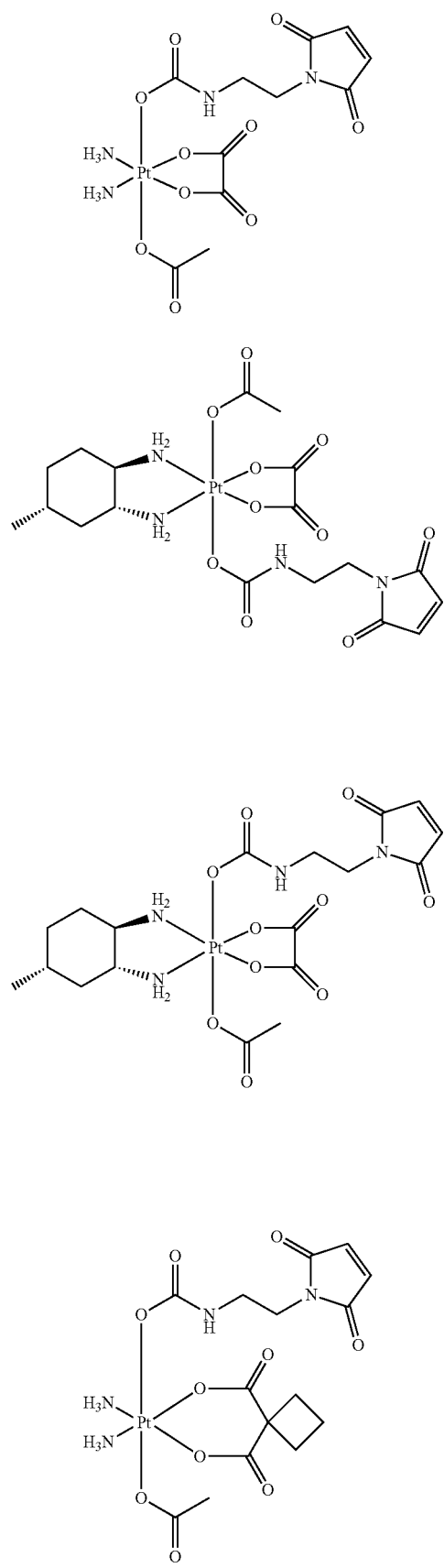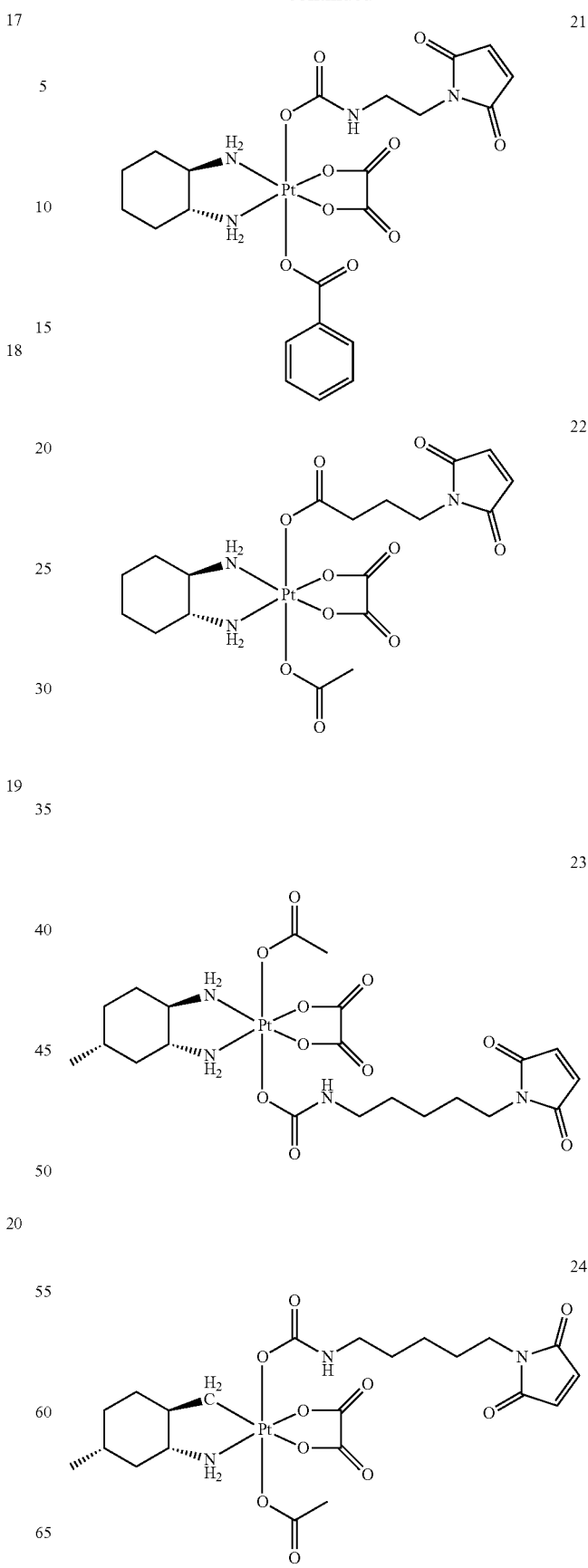

53
-continued
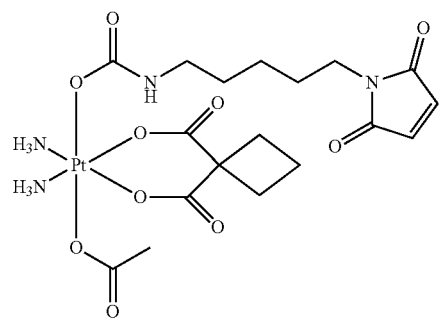
31
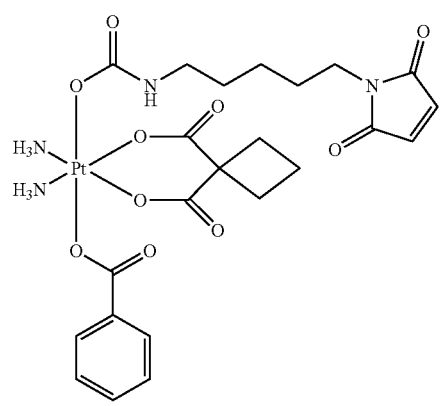
32
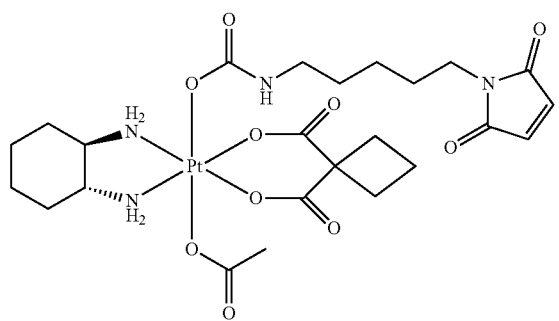
33
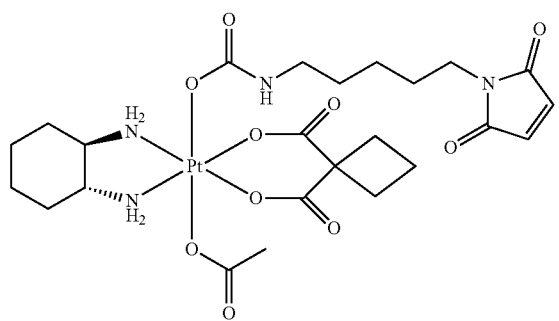
34
54
-continued
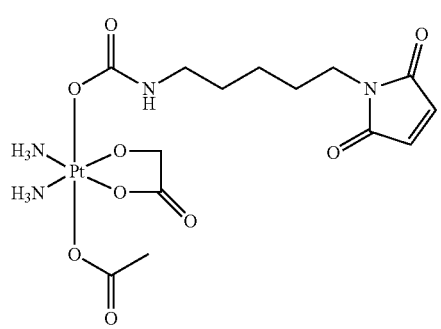
35
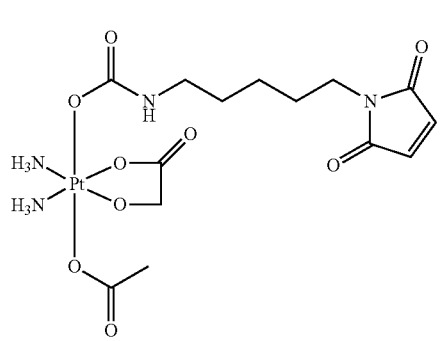
36
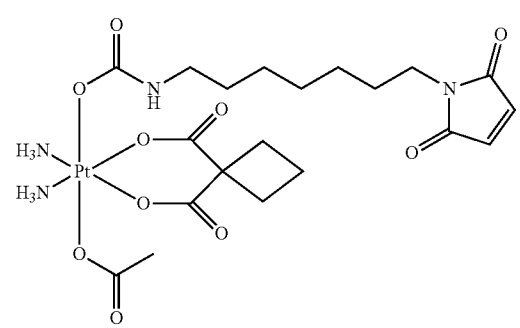
37
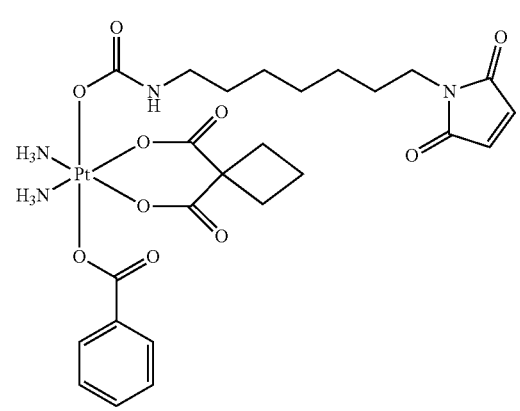
38

39

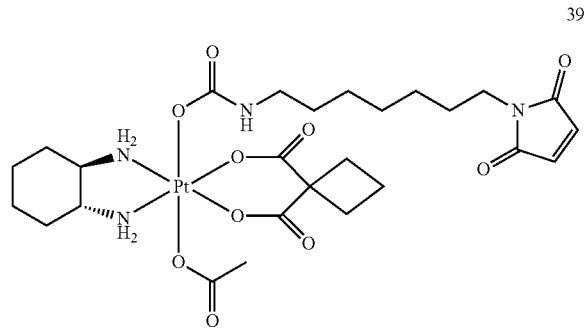

40

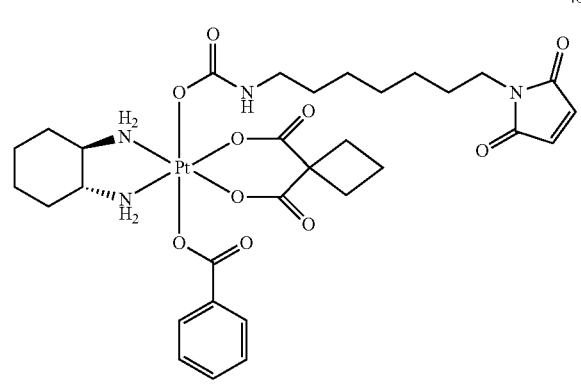

41

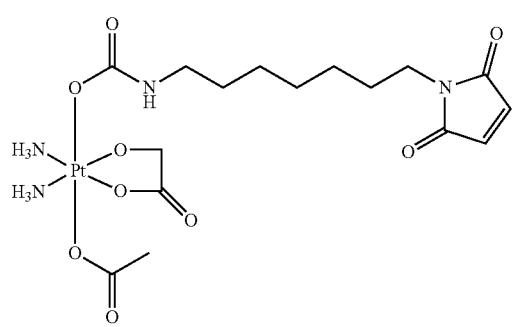

42

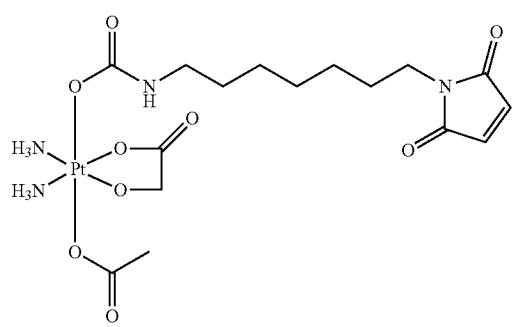

or a pharmaceutically acceptable salt or solvate thereof.
13. The compound of item 1, which is a compound having the following formula:

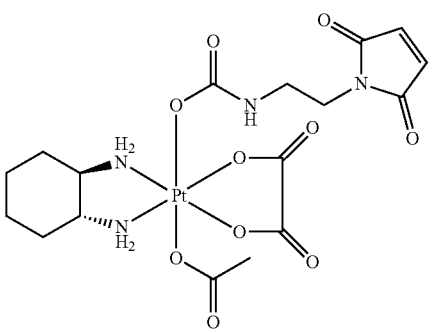

or a pharmaceutically acceptable salt or solvate thereof.
14. The compound of item 1, which is a compound having the following formula:

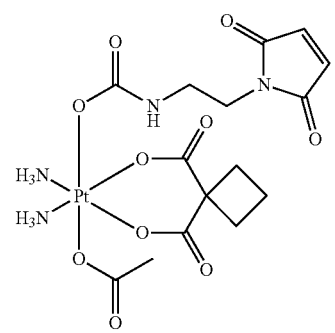

or a pharmaceutically acceptable salt or solvate thereof.
15. The compound of item 1, which is a compound having the following formula:

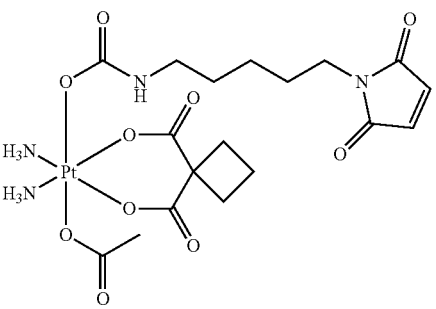

or a pharmaceutically acceptable salt or solvate thereof.
16. A pharmaceutical composition comprising the compound of any one of items 1 to 15 and a pharmaceutically acceptable excipient.
17. The compound of any one of items 1 to 15 or the pharmaceutical composition of item 16 for use as a medicament.
18. The compound of any one of items 1 to 15 or the pharmaceutical composition of item 16 for use in the treatment or prevention of cancer.
19. The compound for use according to item 18 or the pharmaceutical composition for use according to item 18, wherein the cancer is selected from gastrointestinal cancer, colorectal cancer, colon cancer, liver cancer, hepatocellular carcinoma, pancreatic cancer, biliary tract cancer, stomach cancer, genitourinary cancer, bladder cancer, testicular cancer, cervical cancer, malignant mesothelioma, osteogenic sarcoma, esophageal cancer, laryngeal cancer, prostate cancer, hormone-refractory prostate cancer, lung cancer, small cell lung cancer, non-small cell lung cancer, breast cancer, triple-negative breast cancer, breast cancer having a BRCA1 and/or BRCA2 gene mutation, hematological cancer, leukemia, acute lymphoblastic leukemia, acute myeloid leukemia, chronic lymphocytic leukemia, chronic myeloid leukemia, lymphoma, Hodgkin lymphoma, non-Hodgkin lymphoma, follicular lymphoma, diffuse large B-cell lymphoma, ovarian cancer, brain cancer, neuroblastoma, Ewing's sarcoma, kidney cancer, epidermoid cancer, skin cancer, melanoma, head and/or neck cancer, head and neck squamous cell carcinoma, and mouth cancer.
20. The compound for use according to item 18 or 19 or the pharmaceutical composition for use according to item 18 or 19, wherein the cancer is selected from colorectal cancer, colon cancer, pancreatic cancer, lung cancer, non-small cell lung cancer, ovarian cancer, bladder cancer, cervical cancer, malignant mesothelioma, melanoma, head and/or neck cancer, head and neck squamous cell carcinoma, and testicular cancer.
21. The compound for use according to any one of items 18 to 20 or the pharmaceutical composition for use according to any one of items 18 to 20, wherein the cancer is selected from colorectal cancer, colon cancer, pancreatic cancer, lung cancer, non-small cell lung cancer, ovarian cancer, cervical cancer, melanoma, head and/or neck cancer, and head and neck squamous cell carcinoma.
22. The compound for use according to any one of items 18 to 21 or the pharmaceutical composition for use according to any one of items 18 to 21, wherein the cancer is colorectal cancer, colon cancer or pancreatic cancer.
23. The compound for use according to any one of items 18 to 22 or the pharmaceutical composition for use according to any one of items 18 to 22, wherein the compound or the pharmaceutical composition is to be administered in combination with an anticancer drug and/or in combination with radiotherapy and/or immunotherapy.
24. Use of the compound of any one of items 1 to 15 in the preparation of a medicament for the treatment or prevention of cancer.
25. The use of item 24, wherein the cancer is selected from gastrointestinal cancer, colorectal cancer, colon cancer, liver cancer, hepatocellular carcinoma, pancreatic cancer, biliary tract cancer, stomach cancer, genitourinary cancer, bladder cancer, testicular cancer, cervical cancer, malignant mesothelioma, osteogenic sarcoma, esophageal cancer, laryngeal cancer, prostate cancer, hormone-refractory prostate cancer, lung cancer, small cell lung cancer, non-small cell lung cancer, breast cancer, triple-negative breast cancer, breast cancer having a BRCA1 and/or BRCA2 gene mutation, hematological cancer, leukemia, acute lymphoblastic leukemia, acute myeloid leukemia, chronic lymphocytic leukemia, chronic myeloid leukemia, lymphoma, Hodgkin lymphoma, non-Hodgkin lymphoma, follicular lymphoma, diffuse large B-cell lymphoma, ovarian cancer, brain cancer, neuroblastoma, Ewing's sarcoma, kidney cancer, epidermoid cancer, skin cancer, melanoma, head and/or neck cancer, head and neck squamous cell carcinoma, and mouth cancer.
26. The use of item 24 or 25, wherein the cancer is selected from colorectal cancer, colon cancer, pancreatic cancer, lung cancer, non-small cell lung cancer, ovarian cancer, bladder cancer, cervical cancer, malignant mesothelioma, melanoma, head and/or neck cancer, head and neck squamous cell carcinoma, and testicular cancer.
27. The use of any one of items 24 to 26, wherein the cancer is selected from colorectal cancer, colon cancer, pancreatic cancer, lung cancer, non-small cell lung cancer, ovarian cancer, cervical cancer, melanoma, head and/or neck cancer, and head and neck squamous cell carcinoma.
28. The use of any one of items 24 to 27, wherein the cancer is colorectal cancer, colon cancer or pancreatic cancer.
29. The use of any one of items 24 to 28, wherein the medicament is for administration in combination with an anticancer drug and/or in combination with radiotherapy and/or immunotherapy.
30. A method of treating cancer, the method comprising administering the compound of item 1 to a subject in need thereof.
31. The method of item 30, wherein the cancer is selected from gastrointestinal cancer, colorectal cancer, colon cancer, liver cancer, hepatocellular carcinoma, pancreatic cancer, biliary tract cancer, stomach cancer, genitourinary cancer, bladder cancer, testicular cancer, cervical cancer, malignant mesothelioma, osteogenic sarcoma, esophageal cancer, laryngeal cancer, prostate cancer, hormone-refractory prostate cancer, lung cancer, small cell lung cancer, non-small cell lung cancer, breast cancer, triple-negative breast cancer, breast cancer having a BRCA1 and/or BRCA2 gene mutation, hematological cancer, leukemia, acute lymphoblastic leukemia, acute myeloid leukemia, chronic lymphocytic leukemia, chronic myeloid leukemia, lymphoma, Hodgkin lymphoma, non-Hodgkin lymphoma, follicular lymphoma, diffuse large B-cell lymphoma, ovarian cancer, brain cancer, neuroblastoma, Ewing's sarcoma, kidney cancer, epidermoid cancer, skin cancer, melanoma, head and/or neck cancer, head and neck squamous cell carcinoma, and mouth cancer.
32. The method of item 30, wherein the cancer is selected from colorectal cancer, colon cancer, pancreatic cancer, lung cancer, non-small cell lung cancer, ovarian cancer, bladder cancer, cervical cancer, malignant mesothelioma, melanoma, head and/or neck cancer, head and neck squamous cell carcinoma, and testicular cancer.
33. The method of item 30, wherein the cancer is selected from colorectal cancer, colon cancer, pancreatic cancer, lung cancer, non-small cell lung cancer, ovarian cancer, cervical cancer, melanoma, head and/or neck cancer, and head and neck squamous cell carcinoma.
34. The method of item 30, wherein the cancer is colorectal cancer, colon cancer or pancreatic cancer.
35. The method of item 30, wherein the method comprises administering the compound in combination with an anticancer drug and/or in combination with radiotherapy and/or immunotherapy.
36. The method of item 30, wherein the subject is a human.

In a further aspect, the invention relates to the compound KP2260 (as depicted in Example 1) or a pharmaceutically acceptable salt or solvate thereof, or a pharmaceutical composition comprising any of the aforementioned entities in combination with a pharmaceutically acceptable excipient. In this aspect, the invention also relates to KP2260 or a pharmaceutically acceptable salt or solvate thereof, or a pharmaceutical composition comprising any of the aforementioned entities and a pharmaceutically acceptable excipient, for use as a medicament, particularly for use in the treatment or prevention of cancer (including any of the specific cancers described herein in connection with the compound of formula (I)).

The invention is also described by the following illustrative figures. The appended figures show:

FIGS. 1A-G: Superior anticancer activity of KP2299 against CT-26 colon cancer cells in vivo. KP2299 is compared against (FIG. 1A) oxaliplatin, (FIG. 1B) the oxaliplatin-releasing bismaleimide platinum(IV) drug KP2156 and (FIG. 1C) the oxaliplatin-releasing monomaleimide analogue KP2260. Data in FIGS. 1A-C are pooled from several independent experiments. (FIG. 1D) shows data from an experiment regarding a comparison of the cisplatin-releasing monomaleimide analogue KP2372 with cisplatin. (FIG. 1E) and (FIG. 1F) show data from an experiment regarding a comparison of the cisplatin-releasing monomaleimide complex KP2540 and the oxaliplatin-derivate KP2541 (without NH-group in the linker). (FIG. 1G) shows data from one experiment regarding KP2552 (with a 4-methyl-1,2-cyclohexanediamine ligand) and the carboplatin-releasing complex KP2551 in comparison to carboplatin. All experiments have been performed in male Balb/c mice and the control (0.9% NaCl) was treated according to the KP2299 and KP2156 solvent.

FIGS. 2A-D: Impact of gender on the anticancer activity of KP2299 against CT-26 colon cancer cells in vivo. (FIG. 2A) and (FIG. 2B) show tumor burden and survival, respectively, in male animals, while in (FIG. 2C) and (FIG. 2D) data from female mice is shown. In (FIG. 2A) and (FIG. 2B) control mice were treated according to the KP2299 solvent (0.9% NaCl) and in (FIG. 2C) and (FIG. 2D) the control group was treated with 5% glucose according to the oxaliplatin solvent.

FIG. 3: Superior anticancer activity of KP2299 against B16 melanoma cells in vivo. KP2299 is compared against oxaliplatin in male C57/B6JRj mice and the control was treated according to the KP2299 solvent (0.9% NaCl).

FIG. 4: Anticancer activity of KP2299, oxaliplatin, KP2372 and cisplatin against leukemic L1210 cells in vivo. The figure shows data pooled together from several independent experiments.

Figure 5:
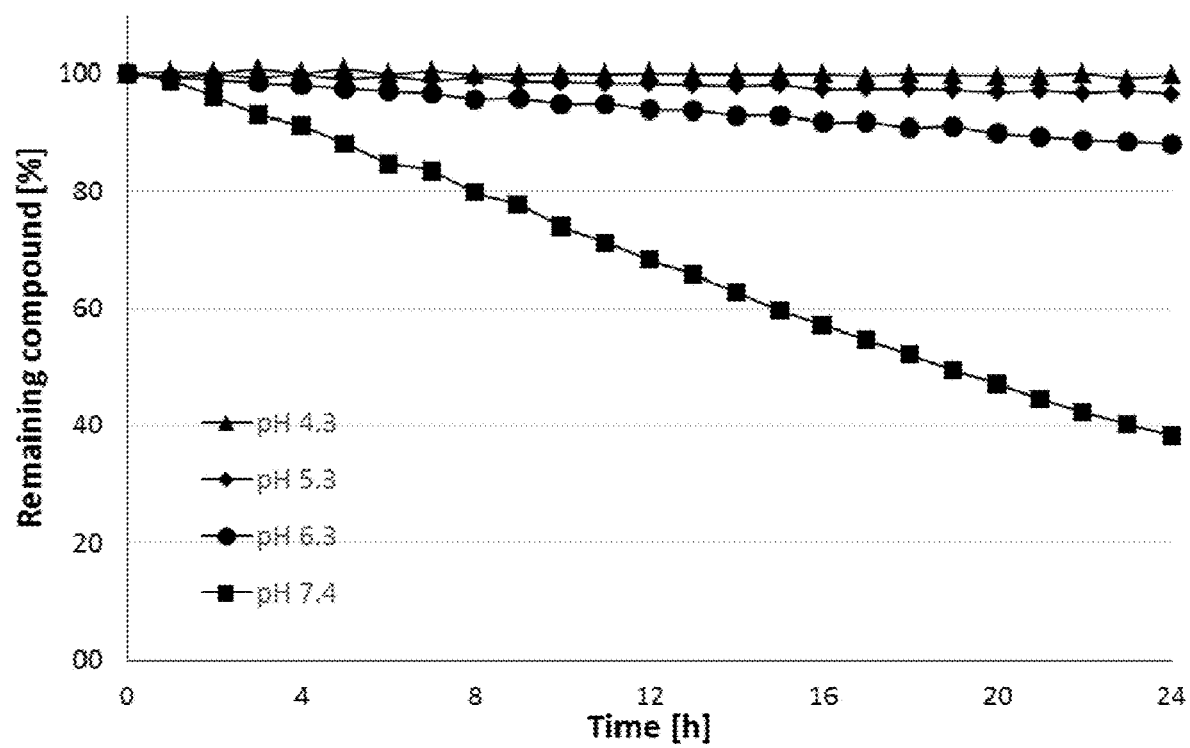

FIG. 5: Hydrolytic stability of KP2299 in buffered aqueous solution at different pH values determined by RP-HPLC.

The invention will now be described by reference to the following examples, which are merely illustrative and are not to be construed as a limitation of the scope of the present invention.

EXAMPLES

The compounds described in this section are defined by their chemical formulae and their corresponding chemical names. In case of conflict between any chemical formula and the corresponding chemical name indicated herein, the present invention relates to both the compound defined by the chemical formula and the compound defined by the chemical name, and particularly relates to the compound defined by the chemical formula.

Example 1: Synthesis of Monomaleimide-Functionalized Platinum Compounds

Scheme 1: Reaction scheme for the synthesis of monomaleimide platinum compounds.

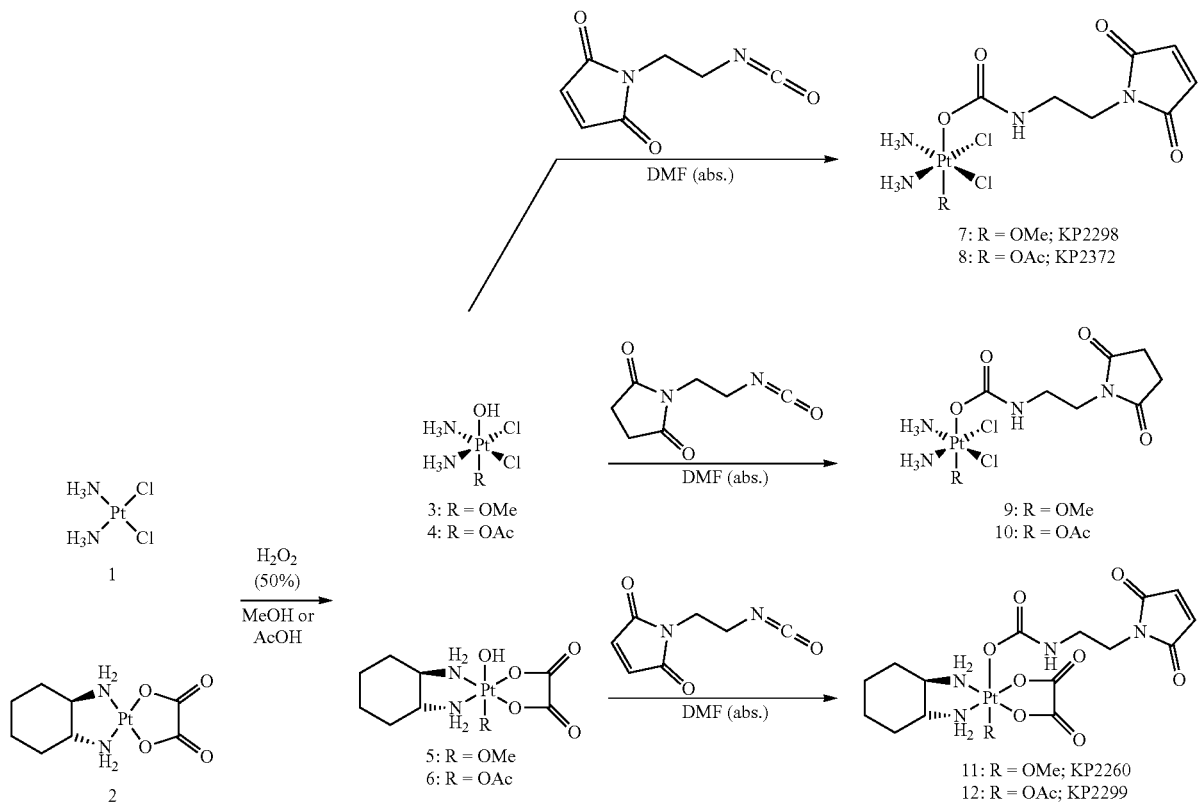

-continued
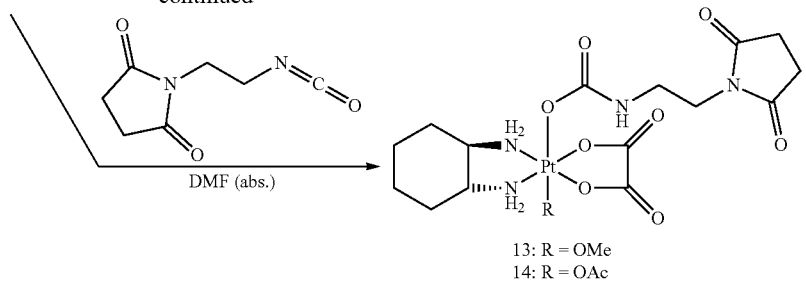
13: R = OMe
14: R = OAc
Scheme 2: Reaction scheme for the synthesis of monomaleimide platinum compounds.
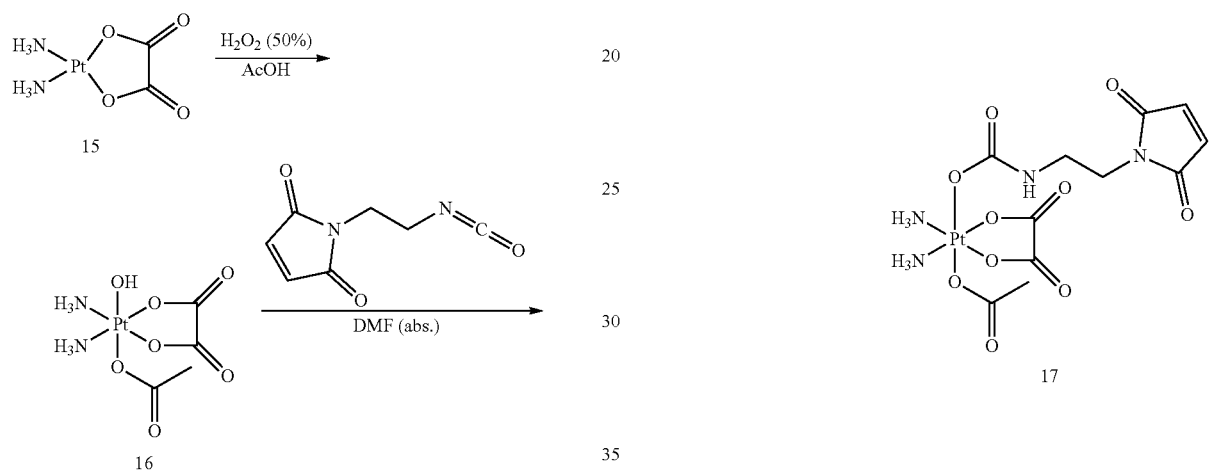

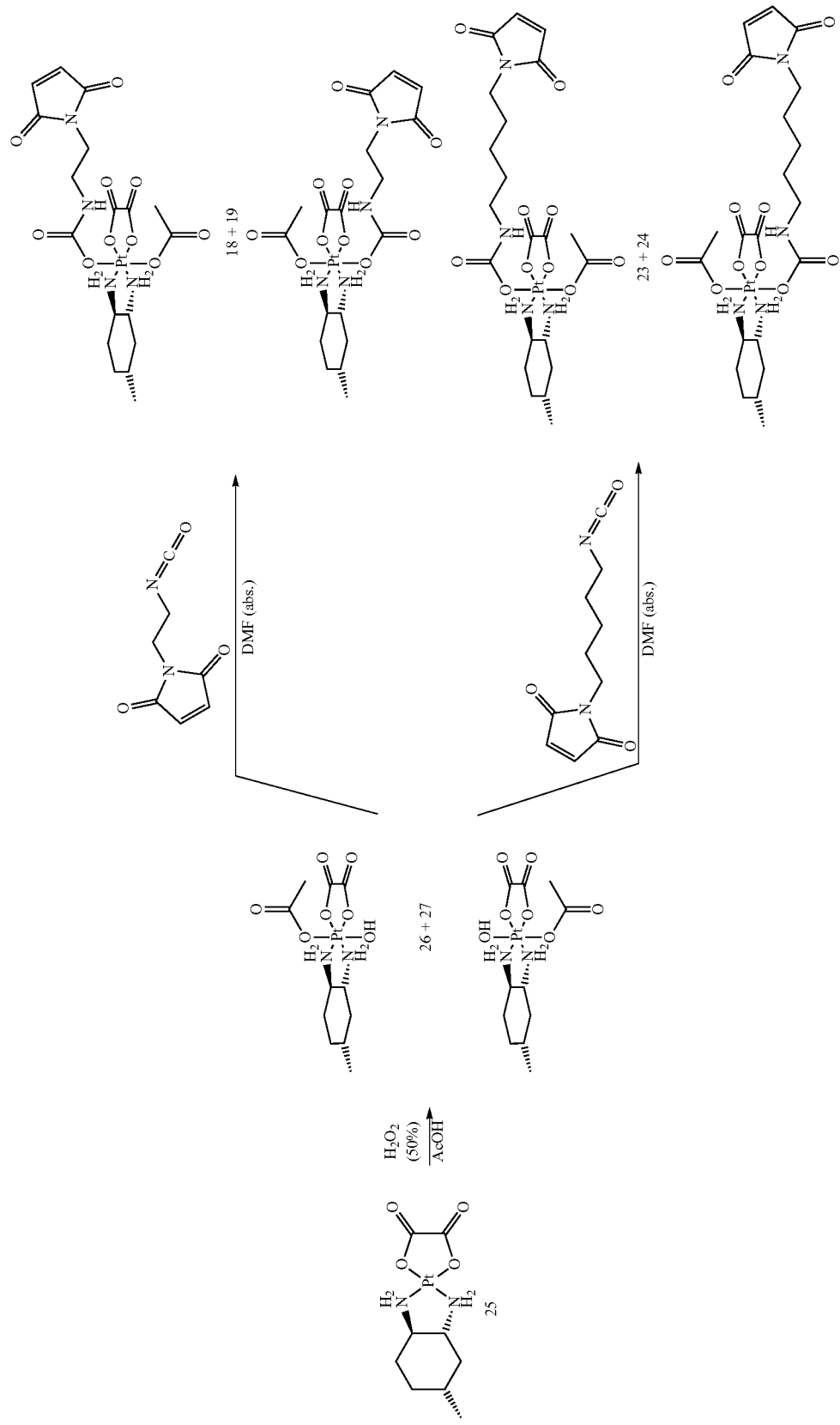
Scheme 3: Reaction scheme for the synthesis of monomaleimide platinum compounds.

Scheme 4: Reaction scheme for the synthesis of monomaleimide platinum compounds.
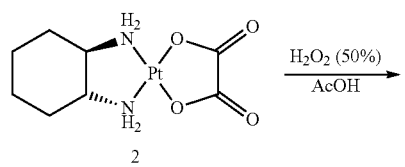
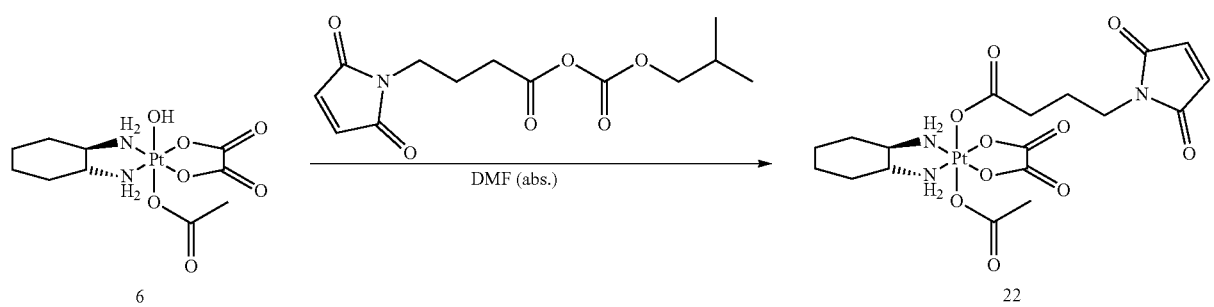
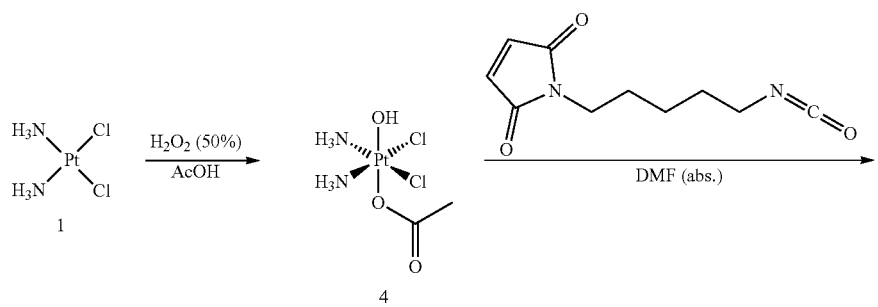
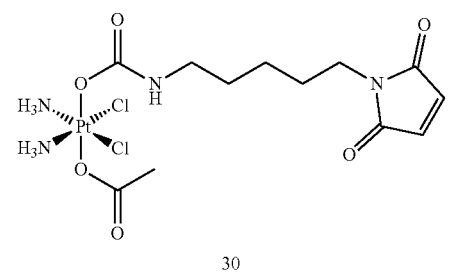
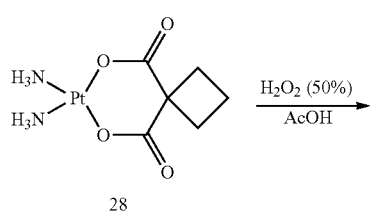

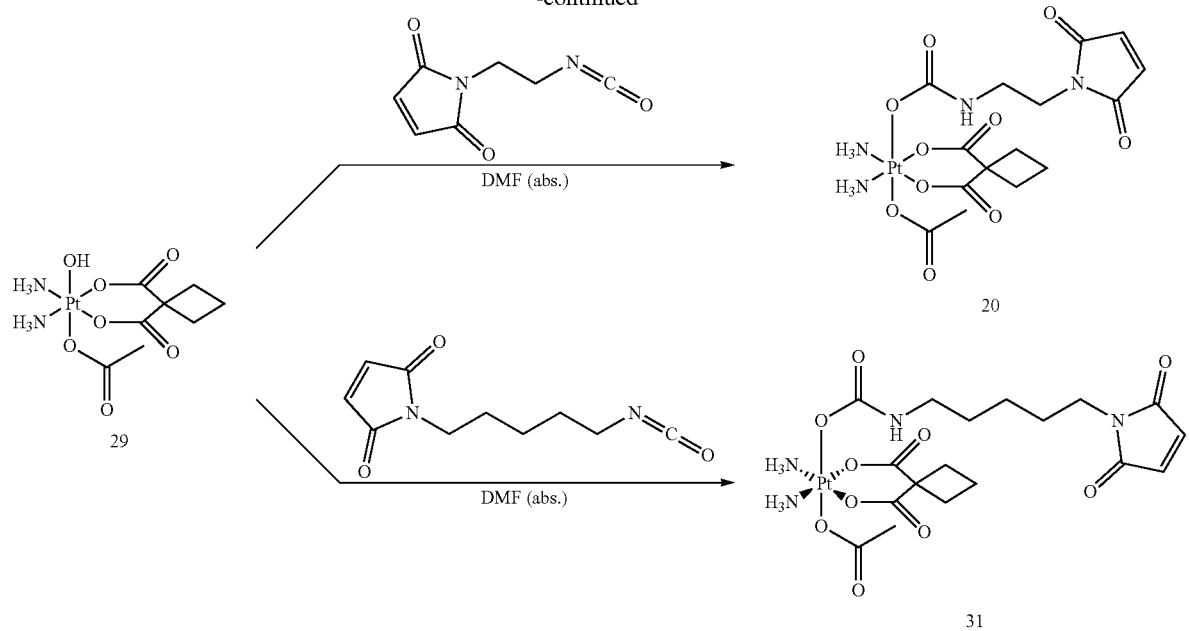

Materials and Methods:

Potassium tetrachloridoplatinate ($K_2PtCl_4$) was purchased from Johnson Matthey (Switzerland). Water for synthesis was taken from a reverse osmosis system and distilled twice before use. For HPLC Milli-Q water (18.2 MΩ·cm, Merck Milli-Q Advantage, Darmstadt, Germany) was used. Other chemicals and solvents were purchased from commercial suppliers (Sigma Aldrich, Acros, Fluka and Fisher Scientific). The platinum(II) precursors cisplatin (1), oxaliplatin (2), (SP-4-2)-diamminediiodidoplatinum(II), (SP-4-3)-[(1R,2R,4R)-4-methylcyclohexane-1,2-diamine] oxalatoplatinum(II) (25) and carboplatin (28) were prepared according to literature-known procedures (cisplatin and (SP-4-2)-diamminediiodidoplatinum(II): Dhara, S. Ch. *Indian J. Chem.* 1970, 8(2), 193-194, oxaliplatin: Kidani, Y; Inagaki, K. *J. Med. Chem.* 1978, 21(12), 1315-1318, carboplatin: Rochon, F. D.; Gruia, L. M. *Inorg. Chim. Acta* 2000, 306, 193-204 and (SP-4-3)-[(1R,2R,4R)-4-methylcyclohexane-1, 2-diamine]oxalatoplatinum(II): Abramkin, S. A.; Jungwirth, U.; Valiahdi, S. M.; Dworak, C.; Habala, L.; Meelich, K.; Berger, W.; Jakupec, M. A.; Hartinger, C. G.; Nazarov, A. A.; Galanski, M.; Keppler, B. K. *J. Med. Chem.* 2010, 53, 7356-7364). Thereafter, these were oxidized with hydrogen peroxide (50%) using either methanol (Dunham, S. O.; Larsen, R. D. *Inorg. Chem.* 1993, 32, 2049-2055) or acetic acid (Lee, Y.-A.; Jung, S. M.; Kang, S. W.; Jung, O.-S. *Transition Met. Chem.* 2004, 29, 710-713) as a solvent to yield the unsymmetrically oxidized platinum(IV) precursors 3-6, 26, 27 and 29. The maleimide- and succinimide-functionalized isocyanate ligands were prepared according to a recently published procedure (Pichler, V.; Mayr, J.; Heffeter, P.; Dömötör, O.; Enyedy, É. A.; Hermann, G.; Groza, D.; Kölensperger, G.; Galanski, M.; Berger, W.; Keppler, B. K.; Kowol, C. R. *Chem. Commun.* 2013, 49, 2049-2051) and the mixed anhydride ligands according to literature-known procedure (Cheronis, J. C.; Whalley, E. T.; Nguyen, K. T.; Eubanks, S. R.; Allen, L. G.; Duggan, M. J.; Loy, S. D.; Bonham, K. A.; Blodgett, J. K. *J. Med. Chem.* 1992, 35, 1563-1572). Compounds 7-14, 17-20, 22-24 and 30-31 were purified by preparative RP-HPLC using a Waters XBridge C18 column on an Agilent 1200 Series system. Milli-Q water, containing 0.1% formic acid and methanol or acetonitrile were used as eluents. Electrospray ionization (ESI) mass spectra were recorded on a Bruker amaZon SL ion trap mass spectrometer in positive and/or negative mode by direct infusion. High resolution mass spectra were measured on a Bruker maXis™ UHR ESI time of flight mass spectrometer. All mass spectra were recorded at the Mass Spectrometry Centre of the University of Vienna. $^1H$-, $^{13}C$-, $^{15}N$-, and $^{195}Pt$-one- and two-dimensional NMR spectra were recorded on a Bruker Avance III 500 MHz spectrometer at 500.10 ($^1H$), 127.75 ($^{13}C$), 50.68 ($^{15}N$), and 107.51 ($^{195}Pt$) MHz at 298 K. For $^1H$- and $^{13}C$-NMR spectra the solvent residual peak was taken as internal reference, whereas $^{195}Pt$-shifts were referenced relative to external $K_2PtCl_4$ and $^{15}N$-shifts relative to external $NH_4Cl$. Elemental analysis measurements were performed on a Perkin Elmer 2400 CHN Elemental Analyzer at the Microanalytical Laboratory of the University of Vienna.

General Procedure for the Synthesis of Compounds 7-14, 17-20, 22-24 and 30-31

The unsymmetrically, oxidized platinum(IV) compound and the corresponding isocyanate (in the case of compounds 7-14, 17-20, 23-24 and 30-31) or the corresponding mixed anhydride (in case of compound 22) were transferred into a Schlenk tube and set under argon atmosphere. After the addition of dry DMF, the suspension was stirred overnight. Remaining precipitates were filtered off, before the DMF was removed under reduced pressure. The remains were taken up as a suspension in methanol and fully precipitated by addition of diethyl ether. After a few hours in the fridge, the crude product was filtered off, washed with diethyl ether and dried under reduced pressure. The crude product was taken up in water and filtered before it was purified by preparative RP-HPLC. Collected product fractions were lyophilized and dried in vacuo.

(OC-6-44)-Diamminedichloridomethoxido[2-(2,5-dioxo-2,5-dihydro-1H-pyrrol-1-yl)ethylcarbamato]platinum(IV) (7; KP2298)

The compound was synthesized from (OC-6-44)-diamminedichloridohydroxidomethoxidoplatinum(IV) (3; 140 mg, 0.40 mmol) and 1-(2-isocyanatoethyl)-1H-pyrrole-2,5-dione (2 eq., 134 mg, 0.80 mmol) in 3 mL DMF (abs.). Purification via preparative RP-HPLC, isocratic with 8% methanol, yielded a pale yellow solid. Yield: 70.5 mg (18%); $^1$H-NMR (DMSO-d6): δ=6.98 (s, 2H, CH), 6.38 (s, 1H, NH), 6.17-5.73 (m, 6H, NH$_3$), 3.46-3.36 (m, 2H, NCH$_2$), 3.06-2.96 (m, 2H, NHCH$_2$), 2.63 (br, 3H, CH$_3$) ppm; $^{13}$C-NMR (DMSO-d6): δ=171.1 (COCH), 164.8 (CONH), 134.5 (CH), 60.5 (CH$_3$), 39.2 (NHCH$_2$), 37.5 (NCH$_2$) ppm; $^{15}$N{$^1$H}-NMR (DMSO-d6): δ=59.5 (NH), −31.7 (NH$_3$) ppm; $^{195}$Pt-NMR (DMSO-d6): δ=2642 (major), 2629 (minor) ppm; HRMS (ESI-TOF): calcd. for [C$_8$H$_{18}$Cl$_2$N$_4$O$_5$Pt—Na$^+$]$^+$: 536.0043, found: 536.0028; elemental analysis calcd. for C$_8$H$_{18}$Cl$_2$N$_4$O$_5$Pt.0.5H$_2$O: C: 18.36, H: 3.27, N: 10.71, O: 16.82, found: C: 18.38, H: 2.92, N: 10.32, O: 16.57.

(OC-6-44)-Acetatodiamminedichlorido[2-(2,5-dioxo-2,5-dihydro-1H-pyrrol-1-yl)ethylcarbamato]platinum(IV) (8; KP2372)

The compound was synthesized from (OC-6-44)-acetatodiamminedichloridohydroxidoplatinum(IV) (4; 450 mg, 1.20 mmol) and 1-(2-isocyanatoethyl)-1H-pyrrole-2,5-dione (2 eq., 398 mg, 2.39 mmol) in 5 mL DMF (abs.). Purification via preparative RP-HPLC, isocratic with 3% methanol, yielded a pale yellow solid. Yield: 267.0 mg (42%); $^1$H-NMR (DMSO-d6): δ=6.98 (s, 2H, CH), 6.80-6.37 (m, 6H, NH$_3$), 6.67 (br, 1H, NH), 3.45-3.37 (m, 2H, NCH$_2$), 3.07-2.99 (m, 2H, NHCH$_2$), 1.90 (s, 3H, CH$_3$) ppm; $^{13}$C-NMR (DMSO-d6): δ=178.2 (COCH$_3$), 171.1 (COCH), 163.8 (CONH), 134.5 (CH), 38.9 (NHCH$_2$), 37.4 (NCH$_2$), 22.8 (CH$_3$) ppm; $^{15}$N{$^1$H}-NMR (DMSO-d6): δ=59.2 (NH), −39.4 (NH$_3$) ppm; $^{195}$Pt-NMR (DMSO-d6): δ=2880 (major), 2860 (minor) ppm; HRMS (ESI-TOF): calcd. for [C$_9$H$_{18}$Cl$_2$N$_4$O$_6$Pt—Na$^+$]$^+$: 564.9944, found: 564.9977; elemental analysis calcd. for C$_9$H$_{18}$Cl$_2$N$_4$O$_6$Pt.1.5H$_2$O: C: 18.99, H: 3.36, N: 9.84, found: C: 18.73, H: 3.18, N: 9.70.

(OC-6-44)-Diamminedichloridomethoxido[2-(2,5-dioxopyrrolidin-1-yl)ethyl)carbamato]platinum(IV) (9)

The compound was synthesized from (OC-6-44)-diamminedichloridohydroxidomethoxidoplatinum(IV) (3; 200 mg, 0.57 mmol) and 1-(2-isocyanatoethyl)pyrrolidine-2,5-dione (1.5 eq., 145 mg, 0.86 mmol) in 3 mL DMF (abs.). Purification via preparative RP-HPLC, isocratic with 5% methanol, yielded a pale yellow solid. Yield: 124.2 mg (42%); $^1$H-NMR (DMSO-d6): δ=6.32 (s, 1H, NH), 6.20-5.70 (m, 6H, NH$_3$), 3.47-3.29 (m, 2H, NCH$_2$), 3.10-2.92 (m, 2H, NHCH$_2$), 2.63 (br, 3H, CH$_3$), 2.58 (br, 4H, COCH$_2$) ppm; $^{13}$C-NMR (DMSO-d6): δ=177.9 (COCH$_2$), 164.9 (CONH), 60.5 (CH$_3$), 38.3 (br, NHCH$_2$, NCH$_2$), 28.1 (COCH2) ppm; $^{195}$Pt-NMR (DMSO-d6): δ=2642 (major), 2629 (minor) ppm; HRMS (ESI-TOF): calcd. for [C$_8$H$_{18}$Cl$_2$N$_4$O$_5$Pt—Na$^+$]$^+$: 538.0200, found: 538.0195; elemental analysis calcd. for C$_8$H$_{18}$Cl$_2$N$_4$O$_5$Pt.0.5H$_2$O: C: 18.32, H: 3.65, N: 10.69, found: C: 18.73, H: 3.66, N: 10.22.

(OC-6-44)-Acetatodiamminedichlorido[2-(2,5-dioxopyrrolidin-1-yl)ethyl)carbamato]platinum(IV) (10)

The compound was synthesized from (OC-6-44)-acetatodiamminedichloridohydroxidoplatinum(IV) (4; 600 mg, 1.60 mmol) and 1-(2-isocyanatoethyl)pyrrolidine-2,5-dione (1.5 eq., 402 mg, 2.39 mmol) in 5 mL DMF (abs.). Purification via preparative RP-HPLC, with a gradient from 5-10.5% methanol in 10 min, yielded a pale yellow solid. Yield: 232.2 mg (27%); $^1$H-NMR (DMSO-d6): δ=6.89-6.33 (m, 7H, NH$_3$, NH), 3.41-3.34 (m, 2H, NCH$_2$), 3.03 (q, J=6.2 Hz, 2H, NHCH$_2$), 2.59 (br, 4H, COCH$_2$), 1.90 (s, 3H, CH$_3$) ppm; $^{13}$C-NMR (DMSO-d6): δ=178.2 (COCH$_3$), 177.8 (COCH$_2$), 163.9 (CONH), 38.2 (NHCH$_2$, NCH$_2$), 28.1 (COCH$_2$), 22.8 (CH$_3$) ppm; $^{195}$Pt-NMR (DMSO-d6): δ=2880 (major), 2859 (minor) ppm; HRMS (ESI-TOF): calcd. for [CH$_{18}$Cl$_2$N$_4$O$_6$Pt—Na$^+$]$^+$: 567.0100, found: 567.0138; elemental analysis calcd. for C$_9$H$_{18}$Cl$_2$N$_4$O$_6$Pt.H$_2$O: C: 19.23, H: 3.59, N: 9.96, found: C: 19.17, H: 3.35, N: 9.88.

(OC-6-34)-[(1R,2R)-Cyclohexane-1,2-diamine]methoxidooxalato[2-(2,5-dioxo-2,5-dihydro-1H-pyrrol-1-yl)ethylcarbamato]platinum(IV) (11; KP2260)

The compound was synthesized from (OC-6-44)-[(1R,2R)-cyclohexane-1,2-diamine]hydroxidomethoxidooxalatoplatinum(IV) (5; 170 mg, 0.38 mmol) and 1-(2-isocyanatoethyl)-1H-pyrrole-2,5-dione (2 eq., 127 mg, 0.76 mmol) in 7 mL DMF (abs.). Purification via preparative RP-HPLC, with a gradient from 15-35% methanol in 10 min, yielded a white solid. Yield: 88.7 mg (38%); $^1$H-NMR (DMSO-d6): δ=9.85-9.55 (m, 1H, NH$_2$), 8.33-8.09 (m, 1H, NH$_2$), 7.79-7.59 (m, 1H, NH$_2$), 7.07-6.83 (m, 1H, NH$_2$), 6.98 (s, 2H, COCH), 6.44 (s, 1H, NH), 3.55-3.45 (m, 1H, NCH$_2$), 3.39-3.29 (m, 1H, NCH$_2$), 3.15-3.05 (m, 1H, NHCH$_2$), 3.00-2.90 (m, 1H, NHCH$_2$), 2.63-2.43 (m, 2H, CH$_{2,dach}$), 2.41 (s, 3H, CH$_3$), 2.19-2.07 (m, 1H, CH$_{2,dach}$), 2.07-1.96 (m, 1H, CH$_{2,dach}$), 1.60-1.42 (m, 3H, CH$_{2,dach}$), 1.39-1.27 (m, 1H, CH$_{2,dach}$), 1.25-1.07 (m, 2H, CH$_{2,dach}$) ppm; $^{13}$C-NMR (DMSO-d6): δ=171.0 (COCH), 165.2 (CONH), 163.7 (CO$_{ox}$), 163.6 (CO$_{ox}$), 134.4 (COCH), 61.3 (CH$_{dach}$), 59.5 (CH$_{dach}$), 57.4 (CH$_3$), 39.0 (NHCH$_2$), 37.4 (NCH$_2$), 30.6 (CH$_{2,dach}$), 23.7 (CH$_{2,dach}$), 23.6 (CH$_{2,dach}$) ppm; $^{15}$N{$^1$H}-NMR (DMSO-d6): δ=60.9 (NH), −6.4 (NH$_2$), −1.5 (NH$_2$) ppm; $^{195}$Pt-NMR (DMSO-d6): δ=3001 (major), 2995 (minor) ppm; HRMS (ESI-TOF): calcd. for [C$_{16}$H$_{24}$N$_4$O$_9$Pt—Na$^+$]$^+$: 634.1089, found: 634.1089; elemental analysis calcd. for C$_{16}$H$_{24}$N$_4$O$_9$Pt.H$_2$O: C: 30.53, H: 4.16, N: 8.90 found: C: 30.29, H: 4.08, N: 8.75.

(OC-6-34)-Acetato[(1R,2R)-cyclohexane-1,2-diamine]oxalato[2-(2,5-dioxo-2,5-dihydro-1H-pyrrol-1-yl)ethylcarbamato]platinum(IV) (12, KP2299)

The compound was synthesized from (OC-6-44)-acetato[(1R,2R)-cyclohexane-1,2-diamine]hydroxidooxalatoplatinum(IV) (6; 200 mg, 0.42 mmol) and 1-(2-isocyanatoethyl)-1H-pyrrole-2,5-dione (2 eq., 140 mg, 0.85 mmol) in 2 mL DMF (abs.). Purification via preparative RP-HPLC, isocratic with 15% methanol, yielded a white solid. Yield: 111.2 mg (41%); $^1$H-NMR (DMSO-d6): δ=9.63 (bs, 1H, NH$_2$), 8.74-8.00 (m, 3H, NH$_2$), 6.99 (s, 2H, COCH), 6.79 (t, J=5.9 Hz, 1H, NH), 3.58-3.45 (m, 1H, NCH$_2$), 3.42-3.29 (m, 1H, NCH$_2$), 3.19-3.08 (m, 1H, NHCH$_2$), 3.01-2.89 (m, 1H, NHCH$_2$), 2.70-2.60 (m, 1H, CH$_{dach}$), 2.60-2.50 (m, 1H, CH$_{dach}$), 2.15 (bs, 2H, CH$_{2,dach}$), 1.95 (s, 1H, CH$_3$), 1.59-1.10 (m, 6H, CH$_{2,dach}$) ppm; $^{13}$C-NMR (DMSO-d6): δ=178.4 (COCH$_3$), 171.0 (COCH), 164.2 (CONH), 163.3 (CO$_{ox}$), 134.5 (COCH), 61.1 (CH$_{dach}$), 60.7 (CH$_{dach}$), 39.0 (NHCH$_2$), 37.2 (NCH$_2$), 31.0 (CH$_{2,dach}$), 30.9 (CH$_{2,dach}$), 23.5 (CH$_{2,dach}$), 23.4 (CH$_{2,dach}$), 22.9 (CH$_3$) ppm; $^{195}$Pt-NMR (DMSO-d6): δ=3236 (major), 3227 (minor) ppm; HRMS (ESI-TOF): calcd. for [C$_{17}$H$_{24}$N$_4$O$_{10}$Pt—Na$^+$]$^+$: 662.1038, found: 662.1033; elemental analysis calcd. for C$_{17}$H$_{24}$N$_4$O$_{10}$Pt.H$_2$O: C: 31.05, H: 3.99, N: 8.52, found: C: 30.96, H: 3.91, N: 8.44.

(OC-6-34)-[(1R,2R)-Cyclohexane-1,2-diamine]methoxidooxalato[2-(2,5-dioxopyrrolidin-1-yl)ethyl)carbamato]platinum(IV) (13)

The compound was synthesized from (OC-6-44)-[(1R,2R)-cyclohexane-1,2-diamine]hydroxidomethoxidooxalatoplatinum(IV) (5; 200 mg, 0.45 mmol) and 1-(2-isocyanatoethyl)pyrrolidine-2,5-dione (2 eq., 151 mg, 0.90 mmol) in 3 mL DMF (abs.). Purification via preparative RP-HPLC, isocratic with 14% methanol, yielded a white solid. Yield: 118.1 mg (43%); 1H-NMR (DMSO-d6): δ=9.84-9.42 (m, 1H, NH$_2$), 8.20 (bs, 1H, NH$_2$), 7.70 (bs, 1H, NH$_2$), 6.98 (bs, 1H, NH$_2$), 6.43 (t, J=5.9 Hz, 1H, NH), 3.51-3.41 (m, 1H, NCH$_2$), 3.35-3.25 (m, 1H, NCH$_2$), 3.13-2.94 (m, 2H, NHCH$_2$), 2.62-2.55 (m, 1H, CH$_{dach}$), 2.58 (s, 4H, COCH$_2$), 2.54-2.46 (m, 1H, CH$_{dach}$), 2.41 (s, 3H, CH$_3$), 2.17-2.08 (m, 1H, CH$_{2,dach}$), 2.07-1.96 (m, 1H, CH$_{2,dach}$), 1.58-1.42 (m, 3H, CH$_{2,dach}$), 1.41-1.27 (m, 1H, CH$_{2,dach}$), 1.22-1.08 (m, 2H, CH$_{2,dach}$) ppm; $^{13}$C-NMR (DMSO-d6): δ=177.7 (COCH$_2$), 165.3 (CONH), 163.7 (CO$_{ox}$), 163.6 (CO$_{ox}$), 61.3 (CH$_{dach}$), 59.5 (CH$_{da}$ch), 57.4 (CH$_3$), 38.2 (NHCH$_2$), 38.1 (NCH$_2$), 30.6 (CH$_{2,dach}$), 28.0 (CH$_{2,dach}$), 23.7 (CH$_{2,dach}$), 23.6 (CH$_{2,dach}$) ppm; $^{195}$Pt-NMR (DMSO-d6): δ=3000 (major), 2992 (minor) ppm; HRMS (ESI-TOF): calcd. for [C$_{16}$H$_{26}$N$_4$O$_9$Pt—Na$^+$]$^+$: 636.1245, found: 636.1249; elemental analysis calcd. for C$_{16}$H$_{26}$N$_4$O$_9$Pt.H$_2$O: C: 30:43, H: 4:47, N: 8:87, found: C: 30:26, H: 4:59, N: 8:72.

(OC-6-34)-Acetato[(1R,2R)-cyclohexane-1,2-diamine]oxalato[2-(2,5-dioxopyrrolidin-1-yl)ethyl)carbamato]platinum(IV) (14)

The compound was synthesized from (OC-6-44)-acetato[(1R,2R)-cyclohexane-1,2-diamine]hydroxidooxalatoplatinum(IV) (6; 200 mg, 0.42 mmol) and 1-(2-isocyanatoethyl)pyrrolidine-2,5-dione (1.5 eq., 107 mg, 0.63 mmol) in 4 mL DMF (abs.). Purification via preparative RP-HPLC, isocratic with 17% methanol, yielded a white solid. Yield: 92.2 mg (18%); $^1$H-NMR (DMSO-d6): δ=9.76-9.25 (m, 1H, NH$_2$), 8.74-8.02 (m, 3H, NH$_2$), 6.76 (t, J=6.0 Hz, 1H, NH), 3.53-3.42 (m, 1H, NCH$_2$), 3.37-3.25 (m, 1H, NCH$_2$), 3.14-2.95 (m, 2H, NHCH$_2$), 2.71-2.62 (m, 1H, CH$_{dach}$), 2.62-2.53 (m, 1H, CH$_{dach}$), 2.58 (s, 4H, COCH$_2$), 2.14 (bs, 2H, CH$_{2,dach}$), 1.95 (s, 1H, CH$_3$), 1.57-1.33 (m, 4H, CH$_{2,dach}$), 1.29-1.10 (m, 2H, CH$_{2,dach}$) ppm; $^{13}$C-NMR (DMSO-d6): δ=178.4 (COCH$_3$), 177.7 (COCH), 164.2 (CONH), 163.3 (CO$_{ox}$), 61.1 (CH$_{dach}$), 60.8 (CH$_{dach}$), 38.1 (NHCH$_2$), 37.9 (NCH$_2$), 31.0 (CH$_{2,dach}$), 30.9 (CH$_{2,dach}$), 28.0 (COCH$_2$), 23.5 (CH$_{2,dach}$), 23.4 (CH$_{2,dach}$), 22.9 (CH$_3$) ppm; $^{195}$Pt-NMR (DMSO-d6): δ=3236 (major), 3225 (minor) ppm; HRMS (ESI-TOF): calcd. for [C$_{17}$H$_{26}$N$_4$O$_{10}$Pt—Na$^+$]$^+$: 664.1194, found: 664.1189; elemental analysis calcd. for C$_{17}$H$_{26}$N$_4$O$_{10}$Pt·1.5H$_2$O: C: 30.54, H: 4.37, N: 8.38, found: C: 30.37, H: 3.98, N: 8.24.

(SP-4-2)-Diammineoxalatoplatinum(II) (15)

692 mg of (SP-4-2)-diamminediiodidoplatinum(II) (1.43 mmol) were suspended in 13 mL triple distilled water and 475 mg AgNO$_3$ (1.95 eq., 2.80 mmol) were added. The suspension was stirred vigorously for 8 h. Thereafter, the precipitate was filtered off, 257.6 mg potassium oxalate (0.975 eq., 1.40 mmol) were added and the reaction mixture was stirred overnight. After 1 h at 4° C., the white product was filtered off, washed with small amounts of cold triple distilled water, and dried over P$_2$O$_5$ under reduced pressure. Yield: 434.1 mg (98%).

(OC-6-44)-Acetatodiamminehydroxidooxalatoplatinum(IV) (16)

200 mg of (SP-4-2)-diammineoxalatoplatinum(II) (15) (0.63 mmol) were suspended in 35 mL glacial acetic acid. After the addition of 715 µL H$_2$O$_2$ (50%) (20 eq., 12.61 mmol), the suspension was stirred in the dark for 2 days. The white precipitate was filtered off, washed with glacial acetic acid and diethyl ether and dried under reduced pressure. The product was used without further purification. Yield: 175 mg (71%).

(OC-6-34)-Acetatodiammineoxalato[2-(2,5-dioxo-2,5-dihydro-1H-pyrrol-1-yl)ethylcarbamato]platinum(IV) (17)

The compound was synthesized from (OC-6-44)-acetatodiamminehydroxidooxalatoplatinum(IV) (16; 66.3 mg, 0.17 mmol) and 1-(2-isocyanatoethyl)-1H-pyrrole-2,5-dione (2 eq., 56.0 mg, 0.34 mmol) in 5 mL DMF (abs.) according to the general procedure. Purification via preparative RP-HPLC, isocratic with 3% methanol, yielded a white solid. Yield: 17.5 mg (20%); $^1$H-NMR (DMSO-d6): δ=6.99 (s, 2H, CH), 6.85-6.39 (m, 6H, NH$_3$), 6.82 (br, 1H, NH), 3.42 (t, J=6.5 Hz, 2H, NCH$_2$), 3.10-3.00 (m, 2H, NHCH$_2$), 1.92 (s, 3H, CH$_3$) ppm; $^{13}$C-NMR (DMSO-d6): δ=177.8 (COCH$_3$), 171.5 (COCH), 164.2 (CO$_{ox}$), 163.6 (CONH), 135.0 (CH), 39.5 (NHCH$_2$), 37.9 (NCH$_2$), 22.8 (CH$_3$) ppm; $^{195}$Pt-NMR (DMSO-d6): δ=3393 (major), 3383 (minor) ppm; HRMS (ESI-TOF): calcd. for [C$_{11}$H$_{16}$N$_4$O$_{10}$Pt—Na$^+$]$^+$: 582.0406, found: 582.0417.

(OC-6-54-A)-Acetato[(1R,2R,4R)-4-methylcyclohexane-1,2-diamine]hydroxidooxalatoplatinum(IV) (26) and (OC-6-54-C)-Acetato[(1R,2R,4R)-4-methylcyclohexane-1,2-diamine]hydroxidooxalatoplatinum(IV) (27)

The compound mixture was synthesized out of 51.5 mg of (SP-4-3)-[(1R,2R,4R)-4-methylcyclohexane-1,2-diamine]oxalatoplatinum(II) (25, 125.2 µmol) which was suspended in 2 mL glacial acetic acid. After the addition of 71.0 µL H$_2$O$_2$ (50%) (10 eq. 1.25 mmol), the suspension was stirred in the dark for 16 h. The remaining solution was concentrated under reduced pressure and the product precipitated by the addition of MeOH and diethyl ether. The white product was filtered off, washed with diethyl ether and dried under reduced pressure. The product was used without further purification. Yield: 56.0 mg (92%).

Mixture of (OC-6-35-A)-Acetato[(1R,2R,4R)-4-methylcyclohexan-1,2-diamin]oxalato[2-(2,5-dioxo-2,5-dihydro-1H-pyrrol-1-yl)ethylcarbamato]platin(IV) (18) and (OC-6-35-C)-Acetato[(1R,2R,4R)-4-methylcyclohexan-1,2-diamin]oxalato[2-(2,5-dioxo-2,5-dihydro-1H-pyrrol-1-yl)ethylcarbamato]platin(IV) (19)

The compound mixture was synthesized from the racemic mixture of (OC-6-54-A/C)-acetato[(1R,2R,4R)-4-methylcyclohexane-1,2-diamine]hydroxidooxalatoplatinum(IV) (26/27; 50 mg, 102.59 µmol) and 1-(2-isocyanatoethyl)-1H-pyrrole-2,5-dione (3 eq., 51.1 mg, 307.78 µmol) in 1.5 mL DMF (abs.) according to the general procedure. Purification via preparative RP-HPLC, with a gradient from 23-33% methanol in 20 min, yielded a white solid. Yield: 16.7 mg (25%); 1H-NMR (DMSO-d6): δ=9.59 (br, 1H, $NH_2$), 8.53 (br, 1H, $NH_2$), 8.30 (br, 1H, $NH_2$), 8.20 (br, 1H, $NH_2$), 7.00 (s, 2H, COCH), 6.80 (br, 1H, NH), 3.58-3.46 (m, 1H, $NCH_2$), 3.41-3.28 (m, 1H, $NCH_2$), 3.19-3.09 (m, 1H, $NHCH_2$), 3.04-2.92 (m, 1H, $NHCH_2$), 2.80-2.51 (m, 2H, $CH_{dach}$), 2.11 (br, 2H, $CH_{2,dach}$), 1.96 (s, 1H, $CH_3$), 1.60-1.37 (m, 3H, $CH_{2,dach}$), 1.23-1.09 (m, 1H, $CH_{2,dach}$), 1.04-0.86 (m, 1H, $CH_{dach}$), 0.95 (d, J=6.4 Hz, 3H, $CH_{3,dach}$) ppm; HRMS (ESI-TOF): calcd. for $[C_{18}H_{26}N_4O_{10}Pt-Na^+]^+$: 676.1190, found: 676.1190; elemental analysis calcd. for $C_{18}H_{26}N_4O_{10}Pt \cdot H_2O$: C: 32.63, H: 4.11, N: 8.47, found: C: 32.69, H: 4.12, N: 8.15. If desired, compounds 18 and 19 can be separated using, e.g., chiral column chromatography (particularly chiral HPLC).

(SP-4-2)-Diamminecyclobutane-1,1-dicarboxylatoplatinum(II) (28)

1.894 g of (SP-4-2)-diamminediiodidoplatinum(II) (3.92 mmol) were suspended in 150 mL triple distilled water and 1.198 g $Ag_2SO_4$ (0.98 eq., 3.84 mmol) were added. The suspension was stirred vigorously for 4 h. Thereafter, the precipitate was filtered off, a solution of 635.9 mg cyclobutane-1,1-dicarboxylic acid (1.13 eq., 4.41 mmol) and 1.213 g $Ba(OH)_2 \cdot 8H_2O$ (0.98 eq., 3.84 mmol) in 50 mL triple distilled water was added and the reaction mixture was stirred for another hour. After filtration, the solution was concentrated under reduced pressure and the product precipitated with MeOH. The white product was filtered off, washed with MeOH and dried under reduced pressure. Yield: 1.214 g (85%).

(OC-6-44)-acetatodiamminecyclobutane-1,1-dicarboxylatohydroxidoplatinum(IV) (29)

300 mg of (SP-4-2)-diamminecyclobutane-1,1-dicarboxylatoplatinum(II) (28) (0.81 mmol) were suspended in 7 mL glacial acetic acid. After the addition of 458.0 µL $H_2O_2$ (50%) (10 eq. 8.08 mmol), the suspension was stirred in the dark for 2 days. The remaining solution was concentrated under reduced pressure and the product precipitated by the addition of MeOH and diethyl ether. The white product was filtered off, washed with diethyl ether and dried under reduced pressure. The product was used without further purification. Yield: 337.2 mg (93%).

(OC-6-34)-Acetatodiamminecyclobutane-1,1-dicarboxylato[2-(2,5-dioxo-2,5-dihydro-1H-pyrrol-1-yl)ethylcarbamato]platinum(IV) (20; KP2551)

The compound was synthesized from (OC-6-44)-acetatodiamminecyclobutane-1,1-dicarboxylatohydroxidoplatinum (IV) (29; 300.0 mg, 0.67 mmol) and 1-(2-isocyanatoethyl)-1H-pyrrole-2,5-dione (2 eq., 222.8 mg, 1.34 mmol) in 3 mL DMF (abs.) according to the general procedure. Purification via preparative RP-HPLC, isocratic with 7% acetonitrile, yielded a white solid. Yield: 50.6 mg (12%); 1H-NMR (DMSO-d6): δ=6.99 (s, 2H, CH), 6.71-6.24 (m, 6H, $NH_3$), 6.62 (br, 1H, NH), 3.42 (t, J=6.4 Hz, 2H, $NCH_2$), 3.05 (q, J=6.4 Hz, 2H, $NHCH_2$), 2.49 (t, J=8.0 Hz, 4H, $CH_2CCH_2$), 1.90 (s, 3H, $CH_3$), 1.81 (quint, J=8.0 Hz, 2H, $CH_2CCH_2$) ppm; HRMS (ESI-TOF): calcd. for $[C_{15}H_{22}N_4O_{10}Pt-Na^+]^+$: 636.0876, found: 636.0884; elemental analysis calcd. for $C_{16}H_{22}N_4O_{10}Pt \cdot H_2O$: C: 28.53, H: 3.83, N: 8.87, found: C: 28.62, H: 3.75, N: 8.64.

(OC-6-44)-Acetato[(1R,2R)-cyclohexane-1,2-diamine]oxalato[4-(2,5-dioxo-2,5-dihydro-1H-pyrrol-1-yl)butanoato]platinum(IV) (22; KP2541)

The compound was synthesized from (OC-6-44)-acetato[(1R,2R)-cyclohexane-1,2-diamine]hydroxidooxalatoplatinum(IV) (6; 150 mg, 317.7 µmol) and (isobutyl carbonic) 4-(2,5-dioxo-2,5-dihydro-1H-pyrrol-1-yl)butanoic anhydride (1.5 eq., 140 mg, 0.85 mmol) in 2 mL DMF (abs.) according to the general procedure. Purification via preparative RP-HPLC, with a gradient from 15-35% methanol in 20 min, yielded a white solid. Yield: 52.4 mg (26%); 1H-NMR (DMSO-d6): δ=8.52-8.11 (m, 4H, $NH_2$), 7.01 (s, 2H, COCH), 3.46-3.36 (m, 2H, $NCH_2$), 2.67-2.51 (m, 2H, $CH_{dach}$), 2.27 (t, J=7.3 Hz, 2H, $COCH_2$), 2.18-2.06 (m, 2H, $CH_{2,dach}$), 1.96 (s, 3H, $CH_3$), 1.68 (quint, J=7.3 Hz, 2H, $COCH_2CH_2$), 1.56-1.35 (m, 4H, $CH_{2,dach}$), 1.28-1.11 (m, 2H, $CH_{2,dach}$) ppm; HRMS (ESI-TOF): calcd. for $[C_{18}H_{25}N_3O_{10}Pt-Na^+]^+$: 661.1080, found: 661.1080; elemental analysis calcd. for $C_{18}H_{25}N_3{10}Pt \cdot H_2O$: C: 32.93, H: 4.15, N: 6.40, found: C: 33.02, H: 4.12, N: 6.33.

Mixture of (OC-6-35-A)-Acetato[(1R,2R,4R)-4-methylcyclohexan-1,2-diamin]oxalato[5-(2,5-dioxo-2,5-dihydro-1H-pyrrol-1-yl)pentylcarbamato]platin(IV) (23) and (OC-6-35-C)-Acetato[(1R,2R,4R)-4-methylcyclohexan-1,2-diamin]oxalato[5-(2,5-dioxo-2,5-dihydro-1H-pyrrol-1-yl)pentylcarbamato]platin(IV) (24)

The compound mixture (KP2552) was synthesized from the racemic mixture of (OC-6-54-A/C)-acetato[(1R,2R,4R)-4-methylcyclohexane-1,2-diamine]hydroxidooxalatoplatinum(IV) (26/27; 52.0 mg, 106.7 µmol) and 1-(5-isocyanatopentyl)-1H-pyrrole-2,5-dione (3 eq., 66.6 mg, 320.1 µmol) in 1.5 mL DMF (abs.) according to the general procedure. Purification via preparative RP-HPLC, with a gradient from 18-33% methanol in 30 min, yielded a white solid. Yield: 19.7 mg (27%); 1H-NMR (DMSO-d6): δ=9.62 (br, 1H, $NH_2$), 8.55 (br, 1H, $NH_2$), 8.25 (br, 2H, $NH_2$), 7.01 (s, 2H, COCH), 6.78 (br, 1H, NH), 3.41-3.33 (m, 2H, $NCH_2$), 2.96-2.77 (m, 2H, $CH_2$), 2.71-2.48 (m, 2H, $CH_{2,dach}$), 2.16-2.02 (m, 2H, $CH_{2,dach}$), 1.96 (s, 1H, $CH_3$), 1.57-1.25 (m, 7H, $CH_{2,dach}$, $CH_2$), 1.25-1.05 (m, 3H, $CH_{2,dach}$, $CH_2$), 1.01-0.84 (m, 1H, $CH_{dach}$), 0.93 (d, J=6.3 Hz, 3H, $CH_{3,dach}$) ppm; HRMS (ESI-TOF): calcd. for $[C_{21}H_{32}N_4O_{10}Pt-Na^+]^+$: 718.1660, found: 718.1661; elemental analysis calcd. for $C_{21}H_{32}N_4O_1Pt \cdot 0.5H_2O$: C: 35.80, H: 4.72, N: 7.95, found: C: 36.11, H: 4.68, N: 7.63.

(OC-6-44)-Acetatodiamminedichlorido[5-(2,5-di-oxo-2,5-dihydro-1H-pyrrol-1-yl)pentylcarbamato]platinum(IV) (30; KP2540)

The compound was synthesized from (OC-6-44)-acetatodiamminedichloridohydroxidoplatinum(IV) (4; 322 mg, 0.86 mmol) and 1-(5-isocyanatopentyl)-1H-pyrrole-2,5-dione (2 eq., 356 mg, 1.71 mmol) in 5 mL DMF (abs.) according to the general procedure. Purification via preparative RP-HPLC, isocratic with 25% methanol, yielded a pale yellow solid. Yield: 165.0 mg (33%); $^1$H-NMR (DMSO-d6): δ=7.01 (s, 2H, CH), 6.89-6.34 (m, 6H, NH$_3$), 6.54 (br, 1H, NH), 3.38 (t, J=7.1 Hz, 2H, NCH$_2$), 2.96-2.80 (m, 2H, NHCH$_2$), 1.91 (s, 3H, CH$_3$), 1.47 (quint, J=7.3 Hz, 2H, CH$_2$), 1.41-1.30 (m, 2H, CH$_2$), 1.24-1.14 (m, 2H, CH$_2$) ppm; HRMS (ESI-TOF): calcd. for [C$_{12}$H$_{22}$Cl$_2$N$_4$O$_6$Pt—Na$^+$]$^+$: 607.0454, found: 607.0453; elemental analysis calcd. for C$_{12}$H$_{22}$Cl$_2$N$_4$O$_6$Pt: C: 24.67, H: 3.80, N: 9.59, found: C: 24.58, H: 3.90, N: 9.29.

(OC-6-34)-Acetatodiamminecyclobutane-1,1-dicarboxylato[5-(2,5-dioxo-2,5-dihydro-1H-pyrrol-1-yl)pentylcarbamato]platinum(IV) (31)

The compound was synthesized from (OC-6-44)-acetatodiamminecyclobutane-1,1-dicarboxylatohydroxidoplatinum (IV) (29; 41.0 mg, 101.2 μmol) and 1-(5-isocyanatopentyl)-1H-pyrrole-2,5-dione (2 eq., 42.1 mg, 202.3 μmol) in 2 mL DMF (abs.) according to the general procedure. Purification via preparative RP-HPLC, isocratic with 18% acetonitrile, yielded a white solid. Yield: 30.1 mg (51%); 1H-NMR (DMSO-d6): δ=7.07-6.67 (m, 3H, NH$_3$), 6.99 (s, 2H, CH), 6.44-6.00 (m, 3H, NH$_3$), 6.38 (br, 1H, NH), 3.36 (t, J=7.1 Hz, 2H, NCH$_2$), 2.96-2.78 (m, 2H, NHCH$_2$), 2.69-2.54 (m, 3H, CH$_2$CCH$_2$), 2.25-2.13 (m, 1H, CH$_2$CCH$_2$), 1.94 (s, 3H, CH$_3$), 1.87-1.73 (m, 2H, NCH$_2$CH$_2$), 1.51-1.40 (m, 2H, CH$_2$), 1.39-1.28 (m, 2H, CH$_2$), 1.23-1.11 (m, 2H, CH$_2$) ppm; ESI-MS: calcd. for [C$_{18}$H$_{28}$N$_4$O$_{10}$Pt—Na$^+$]$^+$: 678.13, found: 678.34.

Compounds 21 and 32 to 42 can be prepared in accordance with the synthesis procedures described in the general part of the present specification:

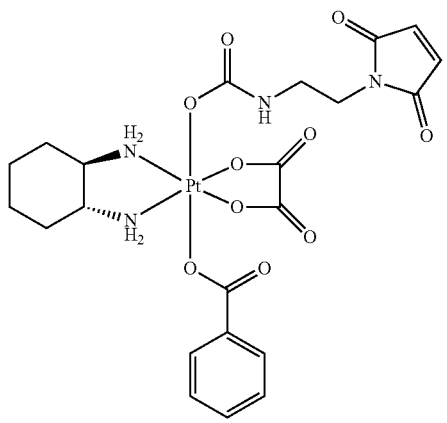

21

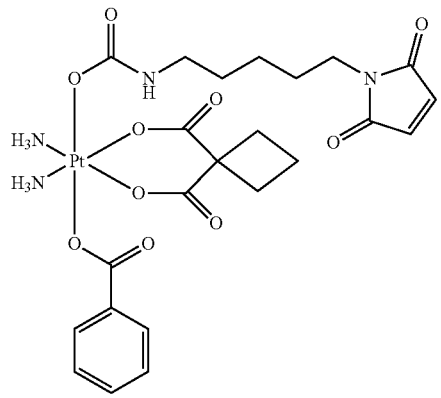

32

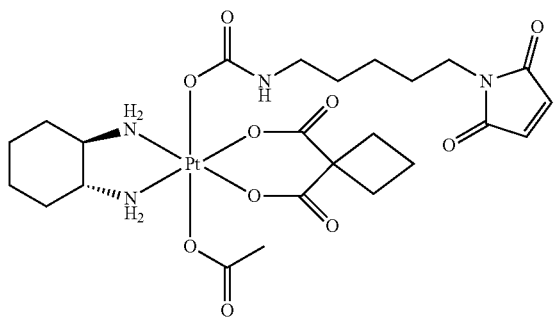

33

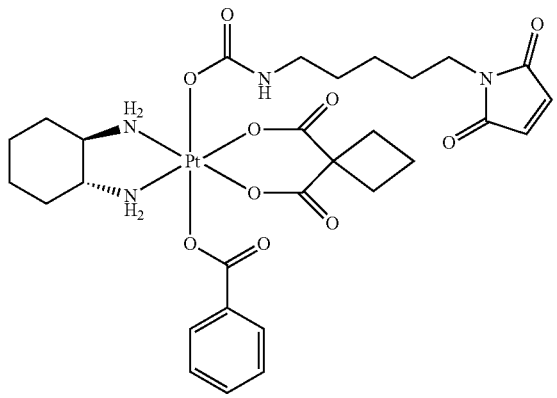

34

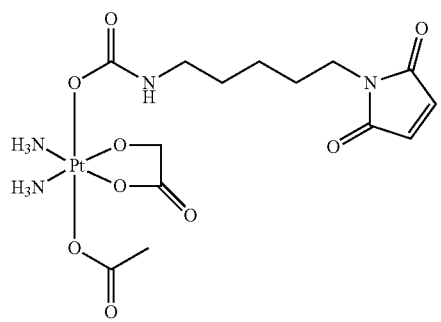

35

36

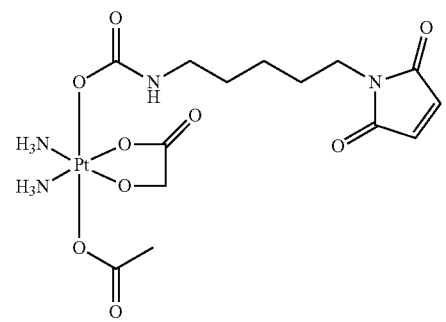

37

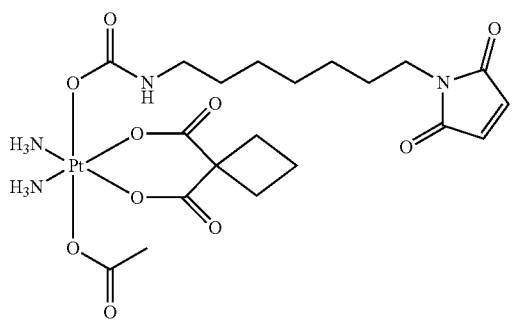

38

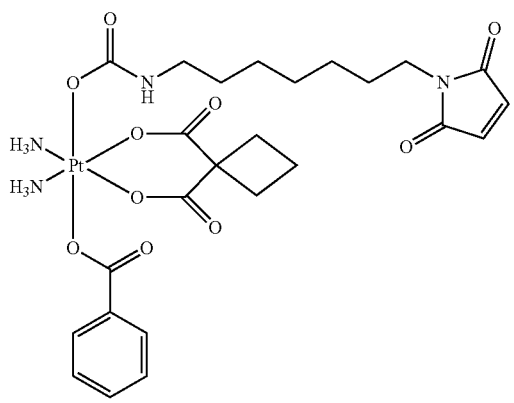

39

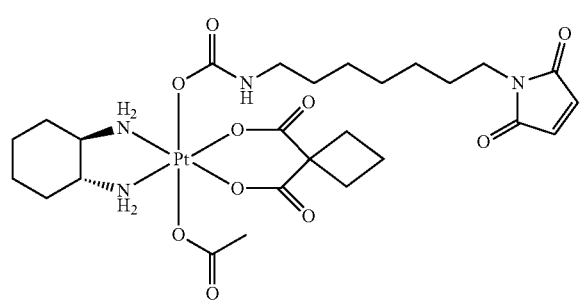

40

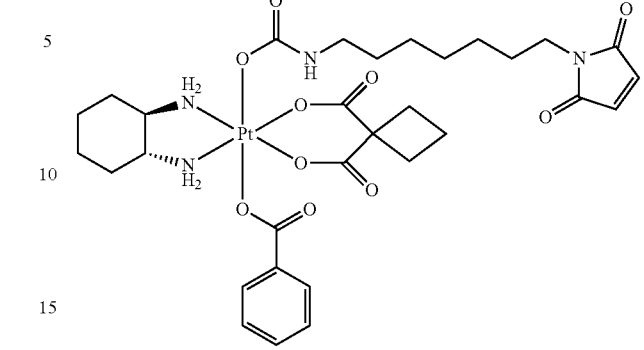

41

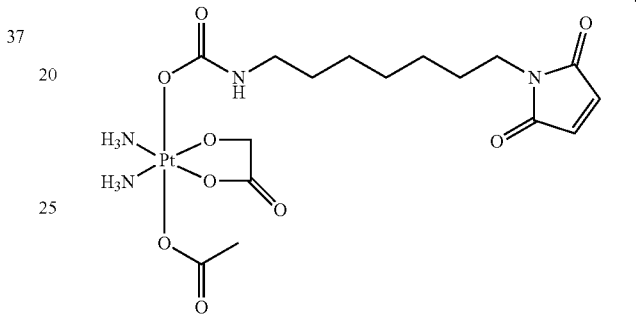

42

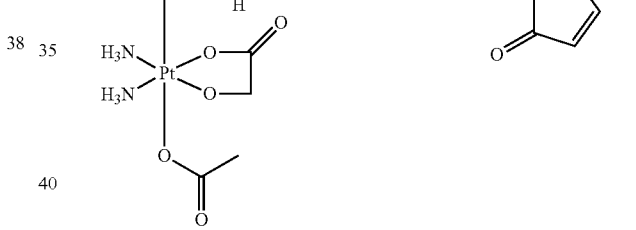

Example 2: RP-HPLC Stability Studies of Compound 12 (KP2299)

The stability of the compounds of the invention in aqueous solutions at different pH values was evaluated by incubation of compound 12 (KP2299) in different buffers and subsequent monitoring of the decrease of the compound peak area with the UV/VIS detector of a RP-HPLC system at 250 nm. Therefore, compound 12 was dissolved at a concentration of 0.5 mM in either 100 mM phosphate buffer pH=7.4, 100 mM sodium acetate buffer pH=6.3, 100 mM sodium acetate buffer pH=5.3 or 100 mM sodium acetate buffer pH=4.3 and incubated at 20° C. for 24 hours. All the measurements were carried out on an Ultimate 3000 RS system (Thermo Scientific, Waltham, Mass., USA) controlled by Chromeleon 7.2 SR4 software using an Acquity BEH C18 reversed phase column (50×3.0 mm, 1.7 μm particle size) from Waters (Milford, USA). Following conditions were used for the runs: flow rate 0.6 mL/min, sampler temperature: 20° C., column oven temperature 25° C., injection volume 10 μL, gradient 5-95% MeOH (and $H_2O$ (+0.1% HCOOH)) in 10 min. The compound was first measured directly after the preparation of the compound (after 2-3 min) and thereafter every 60 min. The decrease of the compound was calculated by the compound peak areas relatively to the peak area directly after the preparation of the compound. It was found that the compound is stable at pH=4.3 and pH=5.3 without significant changes over 24 h. At pH=6.3 the hydrolysis is below 0.5%/h, whereas at pH=7.4 the hydrolysis is quite fast with ~2.6%/h (see FIG. 5). Corresponding results can be obtained when the further compounds of the invention are tested. It has thus been found that the compounds of the present invention, including KP2299, are particularly stable at a pH of about 4 to 6. Hence, the compounds of formula (I) according to the invention can advantageously be provided in the form of a liquid aqueous composition having a pH of 4 to 6 (particularly a pH of about 5), or as a solid composition for rehydration having a pH of 4 to 6 (particularly a pH of about 5) when rehydrated.

Example 3: In Vivo Assays for Anticancer Activity

CT-26 Experiments:

CT-26 colon cancer cells ($5 \times 10^5$ in serum-free medium) were injected subcutaneously into the right flank of Balb/c mice. Animals were treated with the indicated oxaliplatin-releasing drugs at concentrations equimolar to 9 mg/kg oxaliplatin (i.v.; KP2156, KP2299 (compound 12), and KP2541 (compound 22) were dissolved in 0.9% NaCl solution, KP2260 (compound 11) was dissolved in 10% propylene glycol/0.9% NaCl and oxaliplatin was dissolved in 5% glucose solution according to the clinical protocol) twice a week (Mondays and Thursdays). Also in case of KP2552 (mixture of compounds 23 and 24, with the 4-methyl-1,2-cyclohexanediamine moiety) the solvent and application scheme of oxaliplatin was used. In case of cisplatin-releasing prodrugs KP2372 (compound 8) and KP2540 (compound 30), a dose equimolar to 3 mg/kg cisplatin was applied twice a week. For the carboplatin derivative KP2551 (compound 20) a dose equimolar to 12 mg/kg carboplatin was applied. The complexes were dissolved in 0.9% NaCl, while for the platinum(II) drugs 5% glucose solution was used according to the clinical protocol. Animals were controlled for distress development every day and tumor size was assessed regularly by caliper measurement. Tumor volume was calculated using the formula: (length×width$^2$).

B16 Experiments:

B16 melanoma cells ($1 \times 10^5$ in serum-free medium) were injected subcutaneously into the right flank of male C57/B6JRj mice. Animals were treated with KP2299 at concentrations equimolar to 9 mg/kg oxaliplatin (i.v.; dissolved in 0.9% NaCl solution) twice a week. Oxaliplatin was dissolved in 5% glucose solution according to the clinical protocol. Animals were controlled for distress development every day and tumor size was assessed regularly by caliper measurement. Tumor volume was calculated using the formula: (length×width$^2$).

L1210 Experiments:

L1210 murine leukemia cells ($1 \times 10^5$) were injected intraperitoneally in a volume of 0.2 mL into female DBA/2J (cisplatin-releasing drugs) or male DBA/2J×Balb/c SCID F1 mice (oxaliplatin-releasing drugs). Compounds (see FIG. 4; dissolved as described above) were administered intraperitoneally at drug concentrations equimolar to 3 mg/kg cisplatin and 9 mg/kg oxaliplatin, respectively, on day 1, 5, and 9. Toxicity was monitored by daily observation of animals and registration of their body weight. Therapeutic efficacy of the drug candidate was monitored by recording the lengths of survival of experimental mice compared to untreated control animals.

Results:

One of the mono-functionalized oxaliplatin derivatives (KP2299) revealed exceptionally increased anticancer activity compared to oxaliplatin (see FIGS. 1A and 2 for CT-26 and FIG. 3 for B16 tumors) and to the bismaleimide compound KP2156 (see FIG. 1B). It is noteworthy that this activity was especially pronounced in female mice (see FIG. 2), where treatment resulted in complete remission in 3 out of 4 animals. This is remarkable as the very similar mono-functionalized analogue KP2260 (see FIG. 1C), the oxaliplatin-analogue KP2541 which lacks the NH-group in the linker (see FIGS. 1E and 1F) as well as the 4-methyl-1,2-cyclohexanediamine derivative KP2552 were far less or at least later active than KP2299 (see FIG. 1G). In addition, the cisplatin analogues KP2372 (see FIG. 1D) and KP2540 were widely inactive (see FIGS. 1E and 1F). In contrast, the carboplatin prodrug KP2551 had very strong anticancer activity resulting in complete remissions in 2/4 animals. This was especially remarkable as carboplatin in equimolar concentration had no impact on CT-26 tumor growth at all (see FIG. 1G).

In addition to these promising effects in solid cancer models, also in a leukemia model (L1210) distinctly enhanced anticancer activity resulting in cure of several animals was observed. In contrast, free oxaliplatin resulted only in life prolongation in ~50% of the treated animals (see FIG. 4). Again, the cisplatin-releasing derivatives did not show effects superior to free cisplatin. These anti-leukemic effects are unexpected, as maleimide-functionalized drugs are supposed to specifically target the solid tumor tissue due to the so-called enhanced permeability and retention effect (EPR effect).

It has thus been demonstrated that the compounds of formula (I) according to the present invention, including in particular the compounds KP2299 (compound 12) and KP2551 (compound 20), are highly effective in the therapy of cancer, including colon cancer, melanoma and leukemia.

The invention claimed is:

1. A method of treating cancer, wherein the cancer is selected from the group consisting of colon cancer, melanoma, leukemia, ovarian cancer, cervical cancer, lung cancer, small cell lung cancer, non-small cell lung cancer, head and/or neck cancer, head and neck squamous cell carcinoma, breast cancer, and triple-negative breast cancer, the method comprising administering a compound of formula (I) or a pharmaceutically acceptable salt or hydrate thereof to a subject in need thereof,

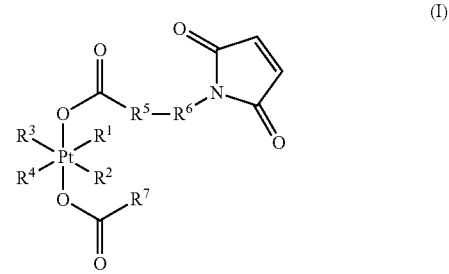

(I)

wherein:

$R^1$ and $R^2$ are joined together to form a moiety (A2) or (A3):

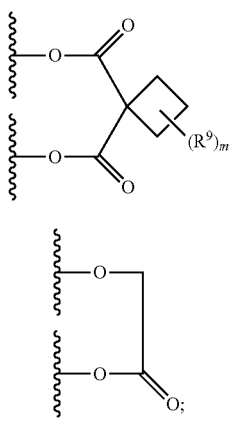

(A2)

(A3)

$R^3$ and $R^4$ are joined together to form a moiety (B1), or $R^3$ is a moiety (B2) and $R^4$ is —NH$_3$, or $R^3$ and $R^4$ are each —NH$_3$:

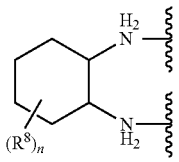

(B1)

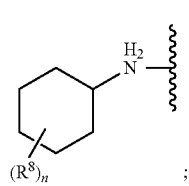

(B2)

$R^5$ is —N(R$^{51}$)— or —CH$_2$—;

$R^{51}$ is hydrogen or C$_{1-8}$ alkyl;

$R^6$ is C$_{1-8}$ alkylene, wherein one or two —CH$_2$— units comprised in said C$_{1-8}$ alkylene are each optionally replaced by a group independently selected from the group consisting of —O—, —CO—, —C(=O)O—, —O—C(=O)—, —N(R$^{61}$)—, —N(R$^{61}$)—CO—, —CO—N(R$^{61}$)—, arylene, and heteroarylene, wherein said arylene and said heteroarylene are each optionally substituted with one or more groups R$^{62}$;

each R$^{61}$ is independently selected from the group consisting of hydrogen and C$_{1-8}$ alkyl;

each R$^{62}$ is independently selected from the group consisting of C$_{1-8}$ alkyl, C$_{2-8}$ alkenyl, C$_{2-8}$ alkynyl, —(C$_{0-3}$ alkylene)-OH, —(C$_{0-3}$ alkylene)-O(C$_{1-8}$ alkyl), —(C$_{0-3}$ alkylene)-SH, —(C$_{0-3}$ alkylene)-S(C$_{1-8}$ alkyl), —(C$_{0-3}$ alkylene)-NH$_2$, —(C$_{0-3}$ alkylene)-NH(C$_{1-8}$ alkyl), —(C$_{0-3}$ alkylene)-N(C$_{1-8}$ alkyl)(C$_{1-8}$ alkyl), —(C$_{0-3}$ alkylene)-halogen, —(C$_{0-3}$ alkylene)-(C$_{1-8}$ haloalkyl), —(C$_{0-3}$ alkylene)-CF$_3$, —(C$_{0-3}$ alkylene)-CN, —(C$_{0-3}$ alkylene)-CHO, —(C$_{0-3}$ alkylene)-CO—(C$_{1-8}$ alkyl), —(C$_{0-3}$ alkylene)-COOH, —(C$_{0-3}$ alkylene)-CO—O—(C$_{1-8}$ alkyl), —(C$_{0-3}$ alkylene)-O—CO—(C$_{1-8}$ alkyl), —(C$_{0-3}$ alkylene)-CO—NH$_2$, —(C$_{0-3}$ alkylene)-CO—NH(C$_{1-8}$ alkyl), —(C$_{0-3}$ alkylene)-CO—N(C$_{1-8}$ alkyl)(C$_{1-8}$ alkyl), —(C$_{0-3}$ alkylene)-NH—CO—(C$_{1-8}$ alkyl), —(C$_{0-3}$ alkylene)-N(C$_{1-8}$ alkyl)-CO—(C$_{1-8}$ alkyl), —(C$_{0-3}$ alkylene)-SO$_2$—NH$_2$, —(C$_{0-3}$ alkylene)-SO$_2$—NH(C$_{1-8}$ alkyl), —(C$_{0-3}$ alkylene)-SO$_2$—N(C$_{1-8}$ alkyl)(C$_{1-8}$ alkyl), —(C$_{0-3}$ alkylene)-NH—SO$_2$—(C$_{1-8}$ alkyl), and —(C$_{0-3}$ alkylene)-N(C$_{1-8}$ alkyl)-SO$_2$—(C$_{1-8}$ alkyl);

$R^7$ is selected from the group consisting of hydrogen, C$_{1-8}$ alkyl, C$_{2-8}$ alkenyl, C$_{2-8}$ alkynyl, cycloalkyl, heterocycloalkyl, aryl, heteroaryl, —O—(C$_{1-8}$ alkyl), —O—(C$_{2-8}$ alkenyl), —O—(C$_{2-8}$ alkynyl), —O-cycloalkyl, —O-heterocycloalkyl, —O-aryl, —O-heteroaryl, —N(R$^{71}$)—(C$_{1-8}$ alkyl), —N(R$^{71}$)—(C$_{2-8}$ alkenyl), —N(R$^{71}$)—(C$_{2-8}$ alkynyl), —N(R$^{71}$)-cycloalkyl, —N(R$^{71}$)-heterocycloalkyl, —N(R$^{71}$)-aryl, and —N(R$^{71}$)-heteroaryl, wherein said C$_{1-8}$ alkyl or the C$_{1-8}$ alkyl moiety comprised in any of the aforementioned groups, said C$_{2-8}$ alkenyl or the C$_{2-8}$ alkenyl moiety comprised in any of the aforementioned groups, and said C$_{2-8}$ alkynyl or the C$_{2-8}$ alkynyl moiety comprised in any of the aforementioned groups are each optionally substituted with one or more groups R$^{72}$, and further wherein said cycloalkyl or the cycloalkyl moiety comprised in any of the aforementioned groups, said heterocycloalkyl or the heterocycloalkyl moiety comprised in any of the aforementioned groups, said aryl or the aryl moiety comprised in any of the aforementioned groups, and said heteroaryl or the heteroaryl moiety comprised in any of the aforementioned groups are each optionally substituted with one or more groups R$^{73}$;

each R$^{71}$ is independently selected from the group consisting of hydrogen and C$_{1-8}$ alkyl;

each R$^{72}$ is independently selected from the group consisting of —OH, —O(C$_{1-8}$ alkyl), —SH, —S(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH(C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl);

each R$^{73}$ is independently selected from the group consisting of C$_{1-8}$ alkyl, C$_{2-8}$ alkenyl, C$_{2-8}$ alkynyl, —(C$_{0-3}$ alkylene)-OH, —(C$_{0-3}$ alkylene)-O(C$_{1-8}$ alkyl), —(C$_{0-3}$ alkylene)-SH, —(C$_{0-3}$ alkylene)-S(C$_{1-8}$ alkyl), —(C$_{0-3}$ alkylene)-NH$_2$, —(C$_{0-3}$ alkylene)-NH(C$_{1-8}$ alkyl), —(C$_{0-3}$ alkylene)-N(C$_{1-8}$ alkyl)(C$_{1-8}$ alkyl), —(C$_{0-3}$ alkylene)-halogen, —(C$_{0-3}$ alkylene)-(C$_{1-8}$ haloalkyl), —(C$_{0-3}$ alkylene)-CF$_3$, —(C$_{0-3}$ alkylene)-CN, —(C$_{0-3}$ alkylene)-CHO, —(C$_{0-3}$ alkylene)-CO—(C$_{1-8}$ alkyl), —(C$_{0-3}$ alkylene)-COOH, —(C$_{0-3}$ alkylene)-CO—O—(C$_{1-8}$ alkyl), —(C$_{0-3}$ alkylene)-O—CO—(C$_{1-8}$ alkyl), —(C$_{0-3}$ alkylene)-CO—NH$_2$, —(C$_{0-3}$ alkylene)-CO—NH(C$_{1-8}$ alkyl), —(C$_{0-3}$ alkylene)-CO—N(C$_{1-8}$ alkyl)(C$_{1-8}$ alkyl), —(C$_{0-3}$ alkylene)-NH—CO—(C$_{1-8}$ alkyl), —(C$_{0-3}$ alkylene)-N(C$_{1-8}$ alkyl)-CO—(C$_{1-8}$ alkyl), —(C$_{0-3}$ alkylene)-SO$_2$—NH$_2$, —(C$_{0-3}$ alkylene)-SO$_2$—NH(C$_{1-8}$ alkyl), —(C$_{0-3}$ alkylene)-SO$_2$—N(C$_{1-8}$ alkyl)(C$_{1-8}$ alkyl), —(C$_{0-3}$ alkylene)-NH—SO$_2$—(C$_{1-8}$ alkyl), and —(C$_{0-3}$ alkylene)-N(C$_{1-8}$ alkyl)-SO$_2$—(C$_{1-8}$ alkyl);

each R$^8$ is independently selected from the group consisting of C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—

(C$_{1-8}$ alkyl), —COOH, —CO—O—(C$_{1-8}$ alkyl), —O—CO—(C$_{1-8}$ alkyl), —CO—NH$_2$, —CO—NH (C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl);

each R$^9$ is independently selected from the group consisting of C$_{1-8}$ alkyl, C$_{2-8}$ alkenyl, C$_{2-8}$ alkynyl, —OH, —O—(C$_{1-8}$ alkyl), —SH, —S—(C$_{1-8}$ alkyl), —NH$_2$, —NH(C$_{1-8}$ alkyl), —N(C$_{1-8}$ alkyl)(C$_{1-8}$ alkyl), halogen, C$_{1-8}$ haloalkyl, —CF$_3$, —CN, —CHO, —CO—(C$_{1-8}$ alkyl), —COOH, —CO—O—(C$_{1-8}$ alkyl), —O—CO—(C$_{1-8}$ alkyl), —CO—NH$_2$, —CO—NH (C$_{1-8}$ alkyl), —CO—N(C$_{1-8}$ alkyl)(C$_{1-8}$ alkyl), —NH—CO—(C$_{1-8}$ alkyl), —N(C$_{1-8}$ alkyl)-CO—(C$_{1-8}$ alkyl), —SO$_2$—NH$_2$, —SO$_2$—NH(C$_{1-8}$ alkyl), —SO$_2$—N(C$_{1-8}$ alkyl)(C$_{1-8}$ alkyl), —NH—SO$_2$—(C$_{1-8}$ alkyl), and —N(C$_{1-8}$ alkyl)-SO$_2$—(C$_{1-8}$ alkyl);

n is an integer of 0 to 8; and m is an integer of 0 to 6.

2. The method of claim 1, wherein R$^5$ is —NH—, —N(—CH$_3$)— or —N(—CH$_2$CH$_3$)—.

3. The method of claim 1, wherein R$^6$ is selected from the group consisting of —CH$_2$—, —(CH$_2$)$_2$—, —(CH$_2$)$_3$—, —(CH$_2$)$_4$—, and —(CH$_2$)$_5$—.

4. The method of claim 1, wherein R$^5$ is —NH—, and R$^6$ is —(CH$_2$)$_2$—.

5. The method of claim 1, wherein R$^7$ is C$_{1-5}$ alkyl.

6. The method of claim 1, wherein R$^7$ is —CH$_3$.

7. The method of claim 1, wherein n and m are each 0.

8. The method of claim 1, wherein R$^3$ and R$^4$ are joined together to form a moiety (B1), wherein n is 1, and wherein R$^8$ is methyl.

9. The method of claim 1, wherein R$^1$ and R$^2$ are joined together to form a moiety (A2), and wherein R$^3$ and R$^4$ are joined together to form a moiety (B1).

10. The method of claim 1, wherein R$^1$ and R$^2$ are joined together to form a moiety (A2), and wherein R$^3$ and R$^4$ are each —NH$_3$.

11. The method of claim 1, wherein R$^1$ and R$^2$ are joined together to form a moiety (A3).

12. The method of claim 1, wherein R$^1$ and R$^2$ are joined together to form a moiety (A2), R$^3$ is a moiety (B2) and R$^4$ is —NH$_3$.

13. The method of claim 1, wherein R$^1$ and R$^2$ are joined together to form a moiety (A2);

R$^5$ is —NH—, —N(—CH$_3$)— or —N(—CH$_2$CH$_3$)—;

R$^6$ is selected from the group consisting of —CH$_2$—, —(CH$_2$)$_2$—, —(CH$_2$)$_3$—, —(CH$_2$)$_4$—, and —(CH$_2$)$_5$—;

R$^7$ is C$_{1-5}$ alkyl; and m is 0.

14. The method of claim 13, wherein R$^3$ and R$^4$ are each —NH$_3$.

15. The method of claim 1, wherein the compound of formula (I) is a compound having any one of the following formulae:

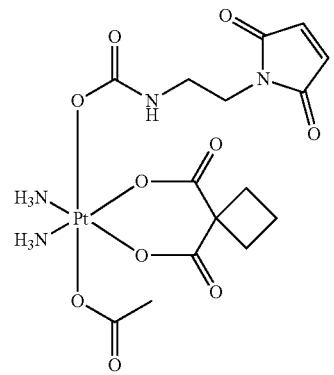

20

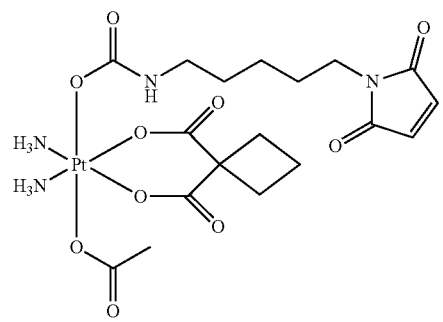

31

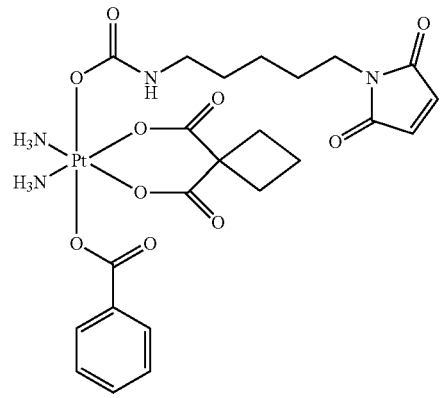

32

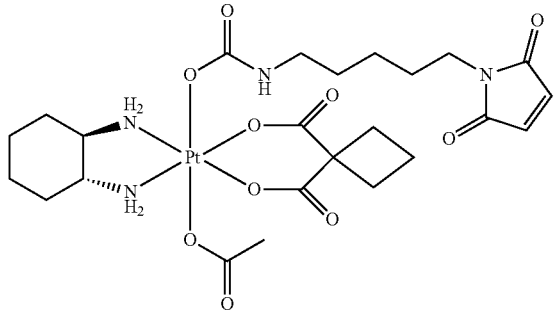

33

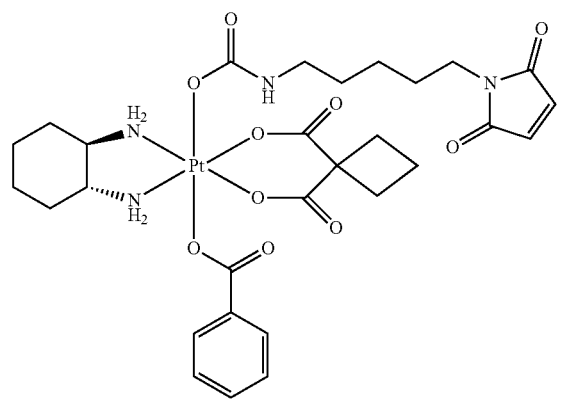
34
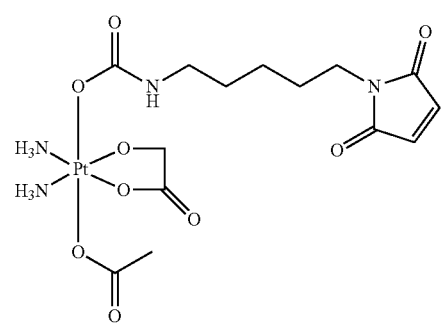
35
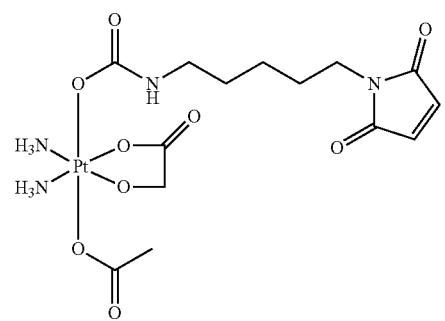
36
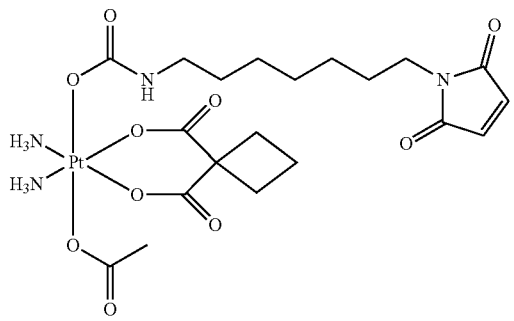
37
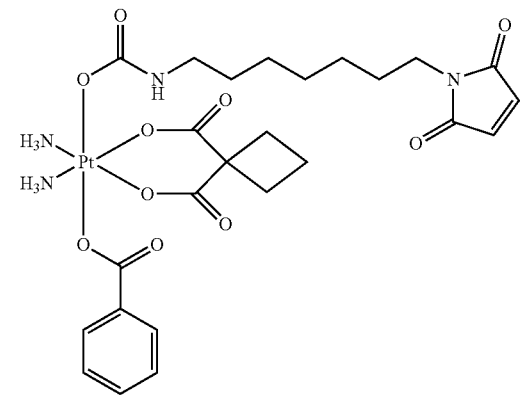
38
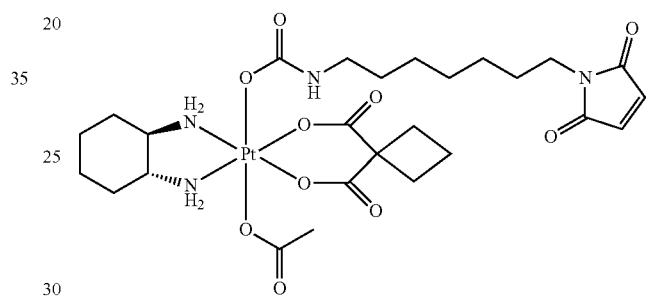
39
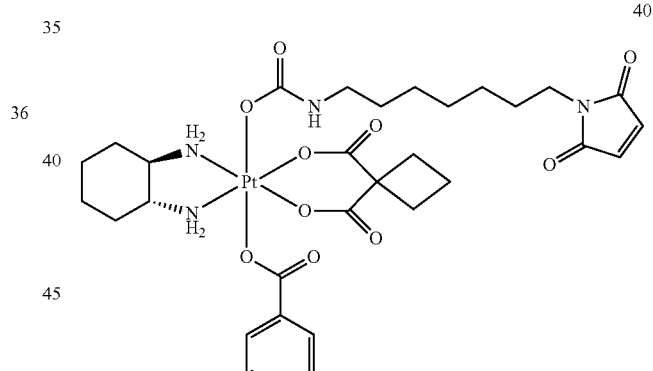
40
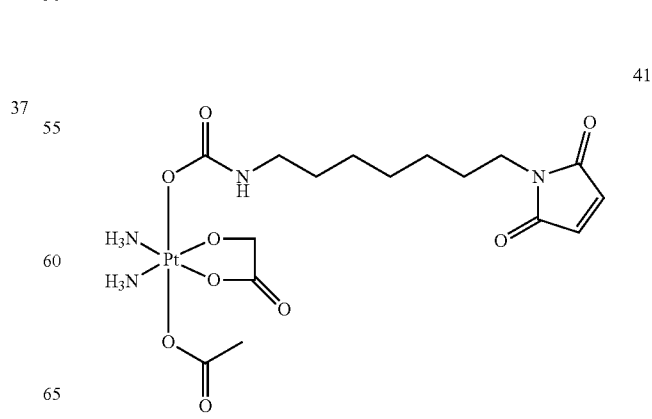
41

-continued

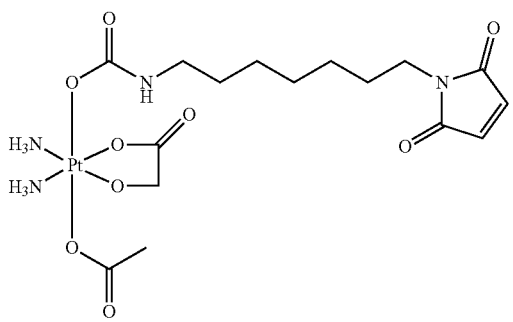

or a pharmaceutically acceptable salt or hydrate thereof.

16. The method of claim 1, wherein the compound of formula (I) is a compound having the following formula:

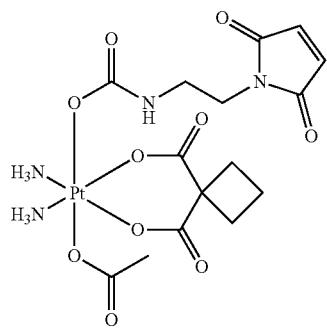

or a pharmaceutically acceptable salt or hydrate thereof.

17. The method of claim 13, wherein the compound of formula (I) or hydrate thereof is not in the form of a salt.

18. The method of claim 14, wherein the compound of formula (I) or hydrate thereof is not in the form of a salt.

19. The method of claim 15, wherein the compound of formula (I) or hydrate thereof is not in the form of a salt.

20. The method of claim 16, wherein the compound of formula (I) or hydrate thereof is not in the form of a salt.

21. A method of treating cancer, wherein the cancer is selected from the group consisting of colon cancer, melanoma, leukemia, ovarian cancer, cervical cancer, lung cancer, small cell lung cancer, non-small cell lung cancer, head and/or neck cancer, head and neck squamous cell carcinoma, breast cancer, and triple-negative breast cancer, the method comprising administering a compound having the following formula:

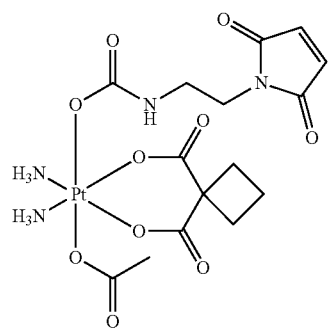

or a hydrate thereof to a subject in need thereof.

22. The method of claim 21, wherein the cancer is colon cancer, melanoma, or leukemia.

23. The method of claim 1, wherein the cancer is colon cancer, melanoma, or leukemia.

24. The method of claim 1, wherein the method comprises administering said compound in combination with an antimitotic agent which is selected from the group consisting of paclitaxel, nab-paclitaxel, docetaxel, larotaxel, ortataxel, and tesetaxel.

25. The method of claim 1, wherein the method comprises administering said compound in combination with folinic acid and 5-fluorouracil.

26. The method of claim 1, wherein the method comprises administering said compound in combination with an immunooncology therapeutic which is an anti-CTLA-4 antibody, an anti-PD-1 antibody, an anti-PD-L1 antibody, an anti-TIM3 antibody, an anti-LAG3 antibody, an anti-OX4 antibody, an anti-CSF1R antibody, an anti-IDO antibody, or an anti-CD40 antibody.

27. The method of claim 1, wherein the subject is a human.

* * * * *